(12) United States Patent
Hammer et al.

(10) Patent No.: US 7,682,603 B2
(45) Date of Patent: Mar. 23, 2010

(54) POLYMERSOMES INCORPORATING HIGHLY EMISSIVE PROBES

(75) Inventors: Daniel A. Hammer, Villanova, PA (US); Michael J. Therien, Philadelphia, PA (US); Paiman Peter Ghoroghchian, Downingtown, PA (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 849 days.

(21) Appl. No.: 10/777,552

(22) Filed: Feb. 12, 2004

(65) Prior Publication Data

US 2005/0019265 A1 Jan. 27, 2005

Related U.S. Application Data

(60) Provisional application No. 60/490,178, filed on Jul. 25, 2003.

(51) Int. Cl.
*A61B 5/00* (2006.01)
*A61B 10/00* (2006.01)
(52) U.S. Cl. ...................... 424/9.61; 424/9.6
(58) Field of Classification Search ............... 424/9.61, 424/9.6
See application file for complete search history.

(56) References Cited

U.S. PATENT DOCUMENTS

| | | | |
|---|---|---|---|
| 3,975,512 A | 8/1976 | Long | 424/5 |
| 4,972,331 A | 11/1990 | Chance | 364/550 |
| 4,987,154 A | 1/1991 | Long, Jr. | 514/772 |
| 5,187,672 A | 2/1993 | Chance et al. | 364/550 |
| 5,371,199 A | 12/1994 | Therien et al. | 534/11 |
| 5,493,018 A | 2/1996 | Liu et al. | 540/302 |
| 5,599,924 A | 2/1997 | Therien et al. | 540/145 |
| 5,707,608 A | 1/1998 | Liu | 424/9.61 |
| 5,756,723 A | 5/1998 | Therien et al. | 540/145 |
| 5,783,306 A | 7/1998 | Therien et al. | 428/411.1 |
| 5,817,830 A | 10/1998 | Therien et al. | 548/400 |
| 5,856,515 A | 1/1999 | Therien et al. | 548/400 |
| 5,955,546 A | 9/1999 | Bates et al. | 525/240 |
| 5,955,603 A | 9/1999 | Therien et al. | 540/145 |
| 5,986,090 A | 11/1999 | Therien et al. | 540/145 |
| 6,060,518 A | 5/2000 | Kabanov et al. | 514/781 |
| 6,100,392 A | 8/2000 | Therien et al. | 540/145 |
| 6,123,923 A * | 9/2000 | Unger et al. | 424/9.52 |
| 6,159,445 A | 12/2000 | Klaveness et al. | 424/9.6 |
| 6,569,528 B2 | 5/2003 | Nam et al. | 428/402 |
| 2002/0044959 A1 | 4/2002 | Goetz et al. | 424/450 |

OTHER PUBLICATIONS

Faustino, M. et al, Photochem. Photobiol., 1997, 66(4), p. 405-412.*
Achilefu, S., et al., "Novel receptor-targeted fluorescent contrast agents for in vivo tumor imaging," *Investigative Radiology*, 2000, 35(8), 479-485.

Ahmed, F., et al., "Block copolymer assemblies with cross-link stabilization: from single-component monolayers to bilayer blends with PEO-PLA," *Langmuir*, 2003, 19, 6505-6511.
Becker, A., et al., "Receptor-targeted optical imaging of tumors with near-infrared fluorescent ligands," *Nature Biotechnol.*, 2001, 19, 327-331.
Berk, D., et al., "Detachment of agglutinin-bonded red blood cells; III. Mechanical analysis for large contact areas," *Biophys. J.*, 1991, 861-872.
Bermudez, H., et al., "Molecular weight dependence of polymersome membrane structure, elasticity, and stability," *Macromolecules*, 2002, 35, 8203-8208.
Bo, L., et al., "Determination of bilayer membrane bending stiffness by tether formation from giant, thin-walled vesicles," *Biophys. J.*, 1989, 55, 509-517.
Božič, B., et al., "Role of lamellar membrane structure in tether formation from bilayuer vesicles," *Biophys. J.*, 1992, 61, 963-973.
Bremer, C., et al., "In vivo molecular target assessment of matrix metalloproteinase inhibition," *Nature Medicine*, 2001, 7(6), 743-748.
Cadiot, P., et al., "Couplings of acetylenes," *Chemistry of Acetylenes*, 1969, Viehe, H.G. (Ed.), 597-647.
Chance, B., et al., "Highly sensitive object location in tissue models with linear in-phase and anti-phase multi-element optical arrays in one or two dimensions," *Proc. Natl. Acad. Sci. USA*, 1993, 90, 3423-3427.
Chance, B., "Near-infrared images using continuous, phase-modulated, and pulsed light with quantitation of blood and blood oxygenation," in *Advances in Optical Biopsy and Optical Mammography*, 1998, 838, 29-45.
Delgado, C., et al., "Coupling of poly(ethylene glycol) to albumin under very mild conditions by activation with tresyl chloride: characterization of the conjugate by patitioning in aqueous two-phase systems," *Biotechnology & Applied Biochemistry*, 1990, 12, 119-128.
Delgado, C., et al., "The uses and properties of PEG-linked proteins," *Critical Reviews in Therapeutic Drug Carrier System*, 1992, 9(3,4), 249-304.
DiMagno, S.G., et al., "Catalytic conversion of simple haloporphyrins into alkyl- aryl-, pyridyl,- and vinyl-substituted porpjyrins," *J. Am. Chem. Soc.*, 1993, 115, 2513-2515.
DiMagno, S.G., et al., "Facile synthesis of meso-tetrakis(perfluoroalkyl)porphyrins: spectroscopic properties and x-ray crystal structure of highly electron-deficient 5,10,15,20-tetrakis(heptafluoropropyl)porphyrin," *J. Org. Chem.*, 1994, 59, 6943-6948.
Discher, B.M., et al., "Cross-linked polymersome membranes: vesicles with broadly adjustable properties," *J. of Phys. Chem. B*, 2002, 106, 2848-2854.

(Continued)

*Primary Examiner*—Michael G Hartley
*Assistant Examiner*—Leah Schlientz
(74) *Attorney, Agent, or Firm*—Woodcock Washburn, LLP

(57) ABSTRACT

The instant invention concerns compositions comprising polymersomes, visible or near infrared emissive agents, and optionally a targeting moiety associated with a surface of the polymersome. The invention also relates to use of these compositions in the treatment of disease and in imaging methodology.

142 Claims, 16 Drawing Sheets

OTHER PUBLICATIONS

Discher, B.M., et al., "Polymersomes: touigh vesicles made from diblock copolymers," *Science*, 1999, 284, 1143-1146.

Eglinton, G., et al., "The coupling of acetylenic compounds," *Adv. Org. Chem.*, 1963, 4, 225-276.

Evans, E., et al., Detachment of agglutinin-bonded red blood cells; I. Forces to rupture molecular-point attachments, *Biophys. J.*, 1991, 59, 838-848.

Evans, E., et al., "Detachment of agglutinin-bonded red blood cells; II. Mechanical energies to separate large contact areas," *Biophys. J.*, 1991, 59, 849-860.

Evans, E., et al., "Adhesivity and rigidity of erythrocyte membrane in relation to wheat germ agglutinin binding," *J. of Cell Biology*, 1984, 98, 1201-1208.

Evans, E., et al., "Physical properties of surfactant bilayer membranes: thermal transitions, elasticity, rigidity, cohesion, and colloidal interactions," *J. Phys. Chem.*, 1987, 91, 4219-4228.

Evans, E., et al., "Interactions between polymer-grafted membranes in concentrated solutions of free polymer," *Langmuir*, 1996, 12, 3031-3037.

Evans, E.A., "Detailed mechanics of membrane-membrane adhesion and separation," *Biophys. J.*, 1985, 48, 175-183.

Evans, E.A., "Detailed mechanics of membrane-membrane adhesion and separation," *Biophys. J.*, 1985, 48, 185-192.

Gordon, et al., The Chemist's Companion, New York, John Wiley & Sons, 1972.

Hajduk, D.A., et al., "Complex phase behavior in aqueous solutions of poly(ethylene oxide)-poly(ethylethylene block copolymers," *J. Phys. Chem. B*, 1998, 102, 4269-4276.

Heinrich, V., et al., "A piconewton force transducer and its application to measurement of the bending stiffness of phospholipids membranes," *Annals of Biomed. Eng.*, 1996, 24, 595-605.

Hermanson, et al., Immobilized Affinity Ligand Techniques, New York, *Academic Press. Inc.*, 1992.

Hillmeyer, M.A., et al., "Synthesis and characterization of model polyalkane-poly(ethylene oxide) block copolymers," *Macromolecules*, 1996, 29, 6994-7002.

Hillmyer, M.A., et al., "Complex phase behavior in solvent-free nonionic surfactants," *Science*, 1996, 271, 976-978.

Hyslop, A.G., et al., "Suzuki porphyrins: new synthons for the fabrication of porphyrin-containing supramolecular assemblies," *J. Am. Chem. Soc.*, 1998, 120, 12676-12677.

Jain, R.J., et al., "Dissecting tumour pathophysiology using intravital microscopy," *Nature, Reviews*, 2002, 2, 266-276.

Kim, D.H., et al., "The influence of tiered layers of surface-grafted poly(ethylene glycol) on receptor—ligand-mediated adhesion between phospholipids monolayer-stabilized microbubbles and coated glass beads," *Langmuir*, 2000, 16, 2808-2817.

Lee, et al., "Preparation, stability, and in vitro performance of vesicles made with diblock copolymers," *Biotechnology and Bioengineering*, 2001, 73(2), 135-145.

Lee, J.C.-M., et al., "From membranes to melts, rouse to reptation: diffusion in polymersome versus lipid bilayers," *Macromolecules*, 2002, 35, 323-326.

Lin, V. S.-Y., et al., "The role of porphyrin-to-porphyrin linkage topology in the extensive modulation of the absorptive and emissive properties of a series of ethynyl-and butadiynyl-bridged bis- and tris(porphinato)zinc chromophores," *Chem. Eur. J.*, 1995, 1(9), 645-651.

Lin, V.S.-Y., et al., "Highly conjugated, acetylenyl bridged porphyrins: new models for light-harvesting antenna systems," *Science*, 1994, 264, 1105-1111.

Meng, F., et al., "Biodegradable polymersomes," *Macromolecules*, 2003, 36, 3004-3096.

Najafi, F., et al., "Biodegradable micelles/polymersomes from fumaric/sebacic acids and poly(ethylene glycol)," *Biomaterials*, 2003, 24, 1175-1182.

New, R.R.C., *Liposomes: A Practical Approach*, Rickwood, D., et al. (Eds.), The Practical Approach Series; Oxford University Press, Oxford, UK, 1997.

Nilsson, K., et al., Tresyl chloride-activated supports for enzyme immobilization, *Methods in Enzymology*, 1984, 135, 65-79.

Noppl-Simson, D.A., et al., "Avidin-biotin interactions at vesicle surfaces: adsorption and binding, cross-bridge formation, and lateral interactions," *Biophys. J.*, 1996, 70, 1391-1401.

Ntziachristos, V., et al., "Conmcurrent MRI and diffuse optical tomography of breast after indocyanine green enhancement," *Proceedings of the National Academy of Sciences of the United States of America*, 2000, 97(6), 2767-2772.

Patai, S., et al., The Chemistry of Functional Groups, *Wiley*, 1983, Supple. C, Part 1, 529-534.

Photos, P.J., et al., "Polymer vesicles in vivo: correlations with PEG molecular weight," *J. of Controlled Release*, 2003, 90, 323-334.

Radzicka, A., et al., "comparing the polarities of the amino acids: side-chain distribution coefficients between the vapor phase, cyclohexane, 1-octanol, and neutral aqueous solution," *Biochemistry*, 1988, 27, 1664-1670.

Rosedale, J.H., et al., "Heterogeneous catalytic hydrogenation of poly(vinylethylene)," *J. Am. Chem. Soc.*, 1988, 110, 3542-3545.

Rosedale, J.H., et al., "Rheology of ordered and disordered symmetric poly(ethylenepropylene)-poly(ethylethylene) diblock copolymers," *Macromolecules*, 1990, 23, 2329-2338.

Rubtsov, I.V., et al., "Ultrafast singlet excited-state polarization in electronically asymmetric ethyne-bridged Bis[(porphinato)zinc(II)] complexes," *J. of the Am. Chem. Soc.*, 2003, 125, 2687-2696.

Streitweiser, A., et al., Introduction to Organic Chemistry, New York, *Macmillan Publishing Co.*, 1992.

Susumu, K., et al., "Decoupling optical and potentiometric band gaps in π-conjugated materials," *J. of the Am. Chem. Soc.*, 2002, 124, 8550-8552.

Warriner, H.E., et al., "Lamellar biogels: fluid-membrane-based hydrogels containing polymer lipids," *Science*, 1996, 271, 969-973.

Waugh, R., et al., "Local and nonlocal curvature elasticity in bilayer membranes by tether formation from lecithin vesicles," *Biophys. J.*, 1992, 61, 974-982.

Weissleder, R., et al., "In vivo imaging of tumors with protease-activated near-infrared fluorescent probes," *Nature Biotechnology*, 1999, 17, 375-378.

Weissleder, R., "A clearer vision for in vivo imaging," *Nature Biotechnology*, 2001, 19,316-317.

Weissleder, R., et al., "Shedding light onto live molecular targets," *Nature Medicine*, 2003, 9(1), 123-128.

Zalteer, A., et al., "In vivo near-infrared fluorescence imaging of osteoblastic activity," *Nature Biotechnology*, 2001, 19, 1148-1154.

\* cited by examiner

*2, 6 substitution –*

*3, 5 substitution –*

- 2,6 substituted oligomers experience blue-shift in fluorescence emission when incorporated in polymersomes as compared to free compound in THF
- 3,5 substituted oligomers experience red-shift in fluorescence emission when incorporated in polymersomes as compared to free compound in THF

Figure 14

| Compound | Emission in THF | R= (ortho-dialkoxy benzyl) in polymersomes | R= (meta-dialkoxy benzyl) in polymersomes |
|---|---|---|---|
| bis-Zn porphyrin (ethyne-linked) | 708 nm | -13 nm | +15 nm |
| bis-Zn porphyrin (butadiyne-linked) | 685 nm | -5 nm | +12 nm |
| tris-Zn porphyrin (ethyne-linked) | 797 nm | -35 nm | +20 nm |
| tris-Zn porphyrin (butadiyne-linked) | 757 | Same | Same |

- Based on nature of R group off of phenyl ring e.g. *3, 5 substituted meso-to-meso ethyne-bridged trimer*

POLYMERSOMES INCORPORATING HIGHLY EMISSIVE PROBES

RELATED APPLICATIONS

This application claims benefit to U.S. Provisional Application No. 60/490,178 filed Jul. 25, 2003.

FIELD OF THE INVENTION

The present invention concerns compositions of polymers, imaging agents and targeting moieties.

BACKGROUND OF THE INVENTION

Liposomes, which are composed of naturally occurring lipids have been used in the delivery of various agents within an organism. Recent research has been directed to synthetic compositions, such as polymersomes, that function similarly in some respects to liposomes. Certain polymer systems, like lipids, spontaneously form closed structures when their building blocks are placed in aqueous medial. Polymersomes, however, are vesicles made using amphiphilic diblock and multiblock copolymers where at least one block is hydrophobic and at least one block is hydrophilic. In particular, these diblock and multiblcok copolymers can form thick-walled vesicles when placed in an aqueous media. Polymersomes can be stably prepared by a number of techniques which are common to liposomes (Lee et al., *Biotechnology and Bioengineering*, vol. 73, no. 2, Apr. 20, 2001). Processes such as film rehydration, sonication, and extrusion can generate many-micron giant vesicles as well as monodisperse vesicles with diameters as small as 100 nanometers.

Certain vesicles of PEO-PEE (polyethyleneoxide-polyethylethylene) or PEO-PBD (polyethyleneoxide-polybutadiene) are known to form thick-walled (e.g., about 100 nm thick) vesicles that exhibit improved stability compared to liposomes. For example, a PEO-PEE diblock introduced by Hillmeyer and Bates (*Macromolecules* 1996; 29:6994-7002), specifically $EO_{40}$-$EE_{37}$ (designated OE7, where EO is ethylene oxide monomer and EE is ethylethylene monomer), has been shown to self-assemble into membranes that are hyper-thick compared to any natural lipid membrane and are also an order of magnitude or more tougher, and thus, show greater mechanical stability (Discher B M, Won Y-Y, Ege D S, Lee JC-M, Bates F S, Discher D E, Hammer D A., *Science* 1999; 284:1143-1146). Augmented chemical stability due to their polyethylene-oxide (PEO) head groups confers biocompatibility, structural integrity in plasma, and "stealth"-like character resulting in long in vivo circulation times (P. J. Photos, L. Bacakova, B. Discher, F. S. Bates, D. E. Discher, *Journal of Controlled Release Jul.* 31, 2003; 90, 323-334;). A novel PEO-PBD diblock, $EO_{26}$-$BD_{46}$ (designated OB2, where EO is ethylene oxide monomer and DB is butadiene monomer)), has also been shown to be capable of making vesicles. Both OE7 and OB2 have mean molecular weights in excess of several kda—much larger than any natural membrane-forming amphiphile.

Optical-based methods constitute new and attractive in vivo imaging modalities due to their impressive potential spatial resolutions, the inherent biological safety of low-energy fluorescent light, and the continuing development of cheap and mobile excitation and detection sources (R. Weissleder, *Nature Biotechnology.* 19, 316-7 (2001)). Although visible probes enable imaging of live animals by intravital microscopy (R. K. Jain, L. L. Munn, D. Fukumura, *Nature Reviews. Cancer.* 2, 266-76 (2002)), their utility is significantly limited at greater than sub-millimeter tissue depths due to excessive light scattering and optical absorption. Because light scattering in the visible spectrum diminishes with the reciprocal of the fourth power of wavelength ($\lambda^{-4}$), and hemoglobin electronic and water vibrational overtone absorptions approach their nadir over the near infrared (NIR) spectral domain (700-950 nm) (B. Chance, in *Advances in Optical Biopsy and Optical Mammography.* (1998), vol. 838, pp. 2945), considerable effort has been spent developing systems that utilize NIR light for in vivo imaging applications (V. Ntziachristos, A. G. Yodh, M. Schnall, B. Chance, *Proceedings of the National Academy of Sciences of the United States of America.* 97, 2767-72 (2000) and R. Weissleder, V. Ntziachristos, *Nature Medicine.* 9, 123-8 (2003)).

Molecules such as porphyrins, chlorophylls, purpurins, tetrapyrroles, macrocycles based on polypyrrole structures and their metalated derivatives, as well as fullerenes can act as imaging agents for target tissues such as tumors. Administration of these agents to an organism results in preferential localization of the agent in any of a variety of pathologies with respect to surrounding tissue. Irradiation of the organism with light of a particular wavelength(s) can lead to absorption of light by the agent, and in some cases, fluorescence or phosphorescence by the agent. This absorption/emission process causes contrast between the target tissue and the surrounding tissue. Detection of this contrast allows imaging of the targeted tissue.

While significant progress has been made in constructing target-specific and locally-active NIR-emissive probes (R. Weissleder, C. H. Tung, U. Mahmood, A. Bogdanov, Jr., *Nature Biotechnology.* 17, 375-8 (1999); S. Achilefu, R. B. Dorshow, J. E. Bugaj, R. Rajagopalan, *Investigative Radiology* 35, 479-485 (August, 2000); A. Becker et al., *Nature Biotechnology.* 19, 327-31 (2001); and A. Zaheer et al., *Nature Biotechnology.* 19, 1148-54 (2001)), the development and delivery of contrast agents of appropriate sensitivity remains a major technological hurdle for the realization of fluorescence-based molecular imaging in deep tissues.

SUMMARY OF THE INVENTION

In some aspects, the invention concerns a polymersome comprising: (i) a plurality of amphiphilic copolymers; and (ii) at least one visible- or near infrared-emissive agent that is dispersed within the polymersome membrane. In some compositions, the emissive agent preferably emits light in the 700-11.00 nm spectral regime. In certain of these compositions, the emissive agent based on a porphyrin-derived structure.

In some embodiments, the invention concerns a polymersome comprising: (i) a plurality of amphiphilic block copolymers, each of the amphiphilic block copolymers comprising at least one hydrophilic polymer bonded to at least one hydrophobic polymer; and (ii) at least one visible- or near infrared-emissive agent that is dispersed within the polymersome membrane. In some compositions, the emissive agent preferably emits light in the 700-1100 nm spectral regime. In certain of these compositions, the emissive agent based on a porphyrin-derived structure.

Certain emissive agents useful in the invention feature a porphycene-, rubyrin-, rosarin-, hexaphyrin-, sapphyrin-, chlorophyll-, chlorin-, phthalocynine-, porphyrazine-, bacteriochlorophyll-, pheophytin-, or texaphyrin-based macrocyclic-based component, or a metalated derivative thereof. In certain other compositions, the emissive agent is a laser dye, fluorophore, lumophore, or phosphor. Preferred laser dyes include p-terphenyl, sulforhodamine B, p-quaterphenyl, Rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HIDC iodide, coumarin 151, PTPC iodide, coumarin 4, cryptocyanine, coumarin 314, DOTC iodide, coumarin 30, HITC iodide, coumarin 500, HITC perchlorate, coumarin 307, PTTC iodide, coumarin 334, DTTC perchlorate, coumarin 7, IR-144, coumarin 343, HDITC perchlorate, coumarin 337, IR-NO, coumarin 6, IR-132, coumarin 152, IR-125, coumarin 153, boron-dipyrromethere, HPTS, flourescein, rhodamine 110, 2,7-dichlorofluorescein, rhodamine 65, and rhodamin 19 perchlorate, rhodamine b, where the laser dye may be modified by addition of a hydrophobic substitutent to render the dye substantially soluble within the polymersome membrane.

In certain compositions, the emissive agent is a near infrared (NIR) emissive species such as di- and tricarbocyanine dyes, croconium dyes, thienylenephenylenevinylene species substituted with electron withdrawing substituents, where the emissive species may be modified by addition of a hydrophobic substitutent to render the dye substantially soluble within the polymersome membrane.

In yet other compositions, the emissive agent is an emissive conjugated compound comprising at least two covalently bound moieties; whereby upon exposing the compound to an energy source for a time and under conditions effective to cause the compound to emit light at a wavelength between 700-1100 nm, and of an intensity that is greater than a sum of light emitted by either of covalently bound moieties individually and/or an integral emission oscillator strength that is greater than the emission oscillator strength manifest by either one of the moieties individually. In certain of these emissive species, the covalently bound moieties are linked by at least one carbon-carbon double bond, carbon-carbon triple bond, or a combination thereof. In some embodiments, the covalently bound moieties that define the emissive species are linked by ethynyl, ethenyl, allenyl, butadiynyl, polyvinyl, thiophenyl, furanyl, pyrrolyl, or p-diethylylarenyl linkers or by a conjugated heterocycle that bears diethynyl, di(polyynynyl), divinyl, di(polyvinvyl), or di(thiophenyl) substituents. In yet other embodiments, the covalently bound moieties that define the emissive species are linked by at least one imine, phenylene, thiophene, or amide, ether, thioether, ester, ketone, sulfone, or carbodiimide group.

In certain compositions, a phorphinato imaging agent may be utilized. These imaging agents include ethynyl- or butadiynyl-bridged multi(porphyrin) compounds that feature a β-to-β, meso-to-β, or meso-to-meso linkage topology, and the porphinato imaging agent being capable of emitting in the 600-to-1100 nm spectral regime. Some porphyrin-based imaging agents are of the formula:

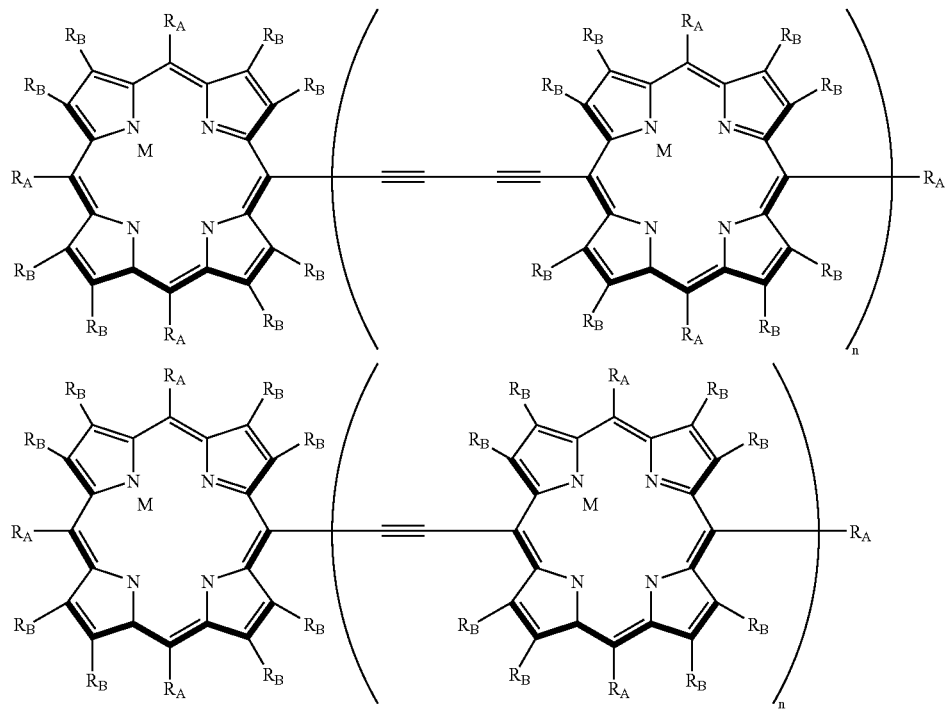

where M is a metal or $H_2$, where $H_2$ denotes the free ligand form of the macrocycle; $R_A$ and $R_B$ are each, independently, H, alkyl or $C_1$-$C_{20}$ heteroalkyl, $C_6$-$C_{20}$ aryl or heteroaryl, $C(R_C)=C(R_D)(R_E)$, $C\equiv C(R_D)$, or a chemical functional group comprising a peptide, nucleoside or saccharide where $R_C$, $R_D$ and $R_E$ are each independently, H, F, Cl, Br, I, $C_1$-$C_{20}$ alkyl or $C_4$-$C_{20}$ heteroalkyl, aryl or heteroaryl, $C_2$-$C_{20}$ alkenyl or heteroalkenyl, alkynyl or $C_2$-$C_{20}$ heteroalkynyl, trialkylsilyl, or porphyrinato; and n is an integer from 1 to 10. In certain compositions, n is an integer from 1 to 8. In other compositions, n is an integer from 1 to 4. In some preferred porphyrin-based imaging agents, M is zinc, magnesium, platinum, palladium, or $H_2$, where $H_2$ denotes the free ligand form of the macrocycle. In other compositions, M is preferably Zn.

In some preferred embodiments, the porphyrin-based imaging agent is emissive. Certain multi(porphyrin) imaging agent features a meso-to-meso ethyne- or butadiyne-bridged linkage topology, that is capable of emitting in the 600-to-1100 nm spectral regime.

In some preferred embodiments, the polymersome is bioresorbable. In certain embodiments, the polymersome contains block polymer components approved by the United States Food and Drug Administration (FDA) for use in vivo.

The polymersome may comprise a single amphiphilic block co-polymer. In other embodiments, more than one amphiphilic block co-polymer may be in the polymersome. In certain embodiments, amphiphilic block co-polymer comprises one hydrophobic polymer and one hydrophilic polymer. In other embodiments, the amphiphilic block co-polymer is a triblock polymer comprising terminal hydrophilic polymers and a hydrophobic polymer internal polymer. Other amphiphilic block co-polymers are tetrablock polymer comprising two hydrophilic polymer blocks and two hydrophobic polymer blocks. Certain tetrablocks have terminal hydrophilic polymer blocks and internal hydrophobic polymer blocks. Other amphiphilic block co-polymers are a pentablock polymer comprising two hydrophilic polymer blocks and three hydrophobic polymer blocks. Other pentablocks have three hydrophilic polymer blocks and two hydrophobic polymer blocks. Yet other pentablocks have four hydrophilic polymer blocks and one hydrophobic polymer block. In yet other embodiments, the amphiphilic block co-polymer comprises at least six blocks, at least two of which are hydrophilic polymer blocks.

In some preferred embodiments, the hydrophilic polymer is substantially soluble in water. Certain preferred hydrophilic polymers are poly(ethylene oxide) or poly(ethylene glycol).

Some polymersomes comprise an amphiphilic co-polymer where the hydrophilic polymer comprises polymerized units selected from ionically polymerizable polar monomers. In certain of these polymersomes, the ionically polymerizable polar monomers comprise an alkyl oxide monomer. In some embodiments, the alkyl oxide monomer is ethylene oxide, propylene oxide, or any combination thereof. In some preferred embodiments, the hydrophilic polymer comprises poly(ethylene oxide). In yet other preferred embodiments, the volume fraction of the hydrophilic polymers in the plurality of amphiphilic block copolymers is less than or equal to 0.40.

Some polymersomes comprise an amphiphilic co-polymer where the hydrophobic polymer is characterized as being substantially insoluble in water. Certain of these hydrophobic polymer comprise polyethylethylene, poly(butadiene), poly(β-benzyl-L-aspartate), poly(lactic acid), poly(propylene oxide), poly(ε-caprolactam), oligo-methacrylate, or polystyrene. In certain preferred embodiments, the hydrophobic polymer comprises polyethylethylene or poly(butadiene). Other compositions comprise hydrophobic polymers of polymerized units selected from ethylenically unsaturated monomers. In some embodiments, the ethylenically unsaturated monomers are hydrocarbons.

In certain embodiments, the polymersome contains a hydrophobic polycaprolactone, polylactide, polyglycolide, or polymethylene carbonate polymer block used in combination with a polyethyleneoxide polymer block. In other compositions, the polymersome contains a hydrophobic polycaprolactone, polylactide, polyglycolide, or polymethylene carbonate polymer block used in combination with a corresponding polyethyleneoxide polymer block.

In some polymersomes, the amphiphilic block copolymer is poly(ethylene oxide)-polyethylethylene, poly(ethylene oxide)-poly(butadiene), poly(ethylene oxide)-poly(ε-caprolactone) or poly(ethylene oxide)-poly(lactic acid).

In some embodiments, the multiblock polymers that comprise the polymersome membrane can be crosslinked, and the emissive fluorophores are embedded therein. In other embodiments, biological entities are incorporated within the interior core of the polymersome, including polymers, cytoskeletal molecules, signaling molecules that can induce phosphorylation, dephosphorylation, amidization, acetylation, enolization, and enzymes that can cause chemical transformations of other biological molecules. In yet other embodiments, the polymersome is engineered, through the composition of its membrane, to fuse or coalesce with another polymersomes, liposome, of cell, thereby transferring its contents to either the interior core of the target fusing object, or to the membrane of target fusing object, affecting a chemical transformation or change in composition with the entity to which it fuses.

Certain polymersomes can comprise an amphiphile that is not a block co-polymer. These include lipids, phospholipids, steroids, cholesterol, single chain alcohols, peptides, nucleotides, saccharides, or surfactants.

Some polymersomes contain an amphiphilic co-polymer is made by attaching two strands comprising different monomers. In some compositions, the amphiphilic co-polymer comprises polymers made by free radical initiation, anionic polymerization, peptide synthesis, or ribosomal synthesis using transfer RNA.

In some aspects, the invention concerns a polymersome comprising: (i) a plurality of amphiphilic block copolymers, each of the amphiphilic block copolymers comprising at least one hydrophilic polymer bonded to at least one hydrophobic polymer; (ii) at least one visible- or near infrared-emissive agent that is segregated within the polymersome membrane; and (iii) at least one targeting moiety associated with a surface of the polymersome. In certain embodiments, the targeting moiety specifically binds with a biological situs. In certain preferred embodiments, the targeting moiety specifically binds with a biological situs under physiological conditions.

In some embodiments, the targeting moiety comprises an antibody, antibody fragment, or substance specific for a given receptor binding site. In other embodiments, the ligand, or targeting moiety comprises a receptor-specific peptide, carbohydrate, protein, lipid, nucleoside, peptide nucleic acid, or combinations thereof. In yet further embodiments the ligand or targeting moiety is an organic compound.

Certain polymersomes additionally comprise a therapeutic agent. Other polymersomes additionally comprising one or more distinct emissive species. In some embodiments, the polymersome additionally comprises a secondary emitter, a cytotoxic agent, a magnetic resonance imaging (MRI) agent, positron emission tomography (PET) agent, radiological imaging agent, ultrasound agent, or a photodynamic therapy (PDT) agent. In some embodiments, the polymersome additionally comprises at least one of a secondary emitter, a cytotoxic agent, a magnetic resonance imaging (MRI) agent, positron emission tomography (PET) agent, photodynamic therapy (PDT) agent, radiological imaging agent, ferromagnetic agent, or ferrimagnetic agent, where the emitter or agent is compartmentalized within the aqueous polymersome interior.

The invention also concerns a method of delivering an agent to a biological situs in a tissue or organism comprising administering to the tissue or organism a polymersome having the agent and comprising (a) a plurality of amphiphilic block copolymers, each of the amphiphilic block copolymers comprising at least one hydrophilic polymer bonded to at least one hydrophobic polymer; (b) at least one visible- or near infrared-emissive agent that is dispersed within the polymersome membrane; and (b) at least one targeting moiety associated with a surface of the polymersome.

In some embodiments, the invention also concerns a method of ascertaining the presence or absence of a disease state in an organism or tissue comprising: administering a polymersome to a patient, the polymersome comprising (a) a plurality of amphiphilic block copolymers, each of the amphiphilic block copolymers comprising at least one hydrophilic polymer bonded to at least one hydrophobic polymer; (b) at least one visible- or near infrared-emissive agent that is dispersed within the polymersome membrane; and (c) at least one targeting moiety associated with a surface of the polymersome; providing an instrument optically coupled to a light source, a light detector, or both, and operating the instrument to monitor the amount or distribution of the phorphinato imaging agent within the organism or tissue.

In yet other embodiments, the invention relates to an in vivo method of diagnostics or imaging comprising: contacting a polymersome with tissue within an organism, the polymersome comprising (a) a plurality of amphiphilic block copolymers, each of the amphiphilic block copolymers comprising at least one hydrophilic polymer bonded to at least one hydrophobic polymer; (b) at least one visible- or near infrared-emissive agent that is dispersed within the polymersome membrane; and (c) at least one targeting moiety associated with a surface of the polymersome; providing an instrument optically coupled to a light source, a light detector, or both, and using the instrument to monitor the amount of the polymersome at a situs within the tissue.

In yet other embodiments, the invention concerns an in vitro diagnostic method comprising: contacting a polymersome with isolated cells, mixtures of cells, or specific cell lines, with the polymersome comprising (a) a plurality of amphiphilic block copolymers, each of the amphiphilic block copolymers comprising at least one hydrophilic polymer bonded to at least one hydrophobic polymer; (b) at least one visible- or near infrared-emissive agent that is dispersed within the polymersome membrane; and (c) at least one targeting moiety associated with a surface of the polymersome; providing an instrument optically coupled to a light source, a light detector, or both, and using the instrument to monitor cell-surface-to-polymersome binding.

The invention also concerns a method of modulating the emission properties of a visible- or near infrared-emissive agent comprising at least two covalently bound moieties, the emissive agent being within a polymeric material, wherein at least one of the bound moieties comprises an ancillary substituent, the size and chemical constitution of said substituent being selected to provide the modulation. In some embodiments, the modulation is of the steady state emission wavelength. In other embodiments, the modulation is of the time-dependent emission dynamics of said emissive conjugated compound.

BRIEF DESCRIPTION OF THE DRAWINGS

FIG. 14 shows the tuning of fluorescence emission by controlling the position of the substituent groups.

DETAILED DESCRIPTION OF ILLUSTRATIVE EMBODIMENTS

Figure 1:
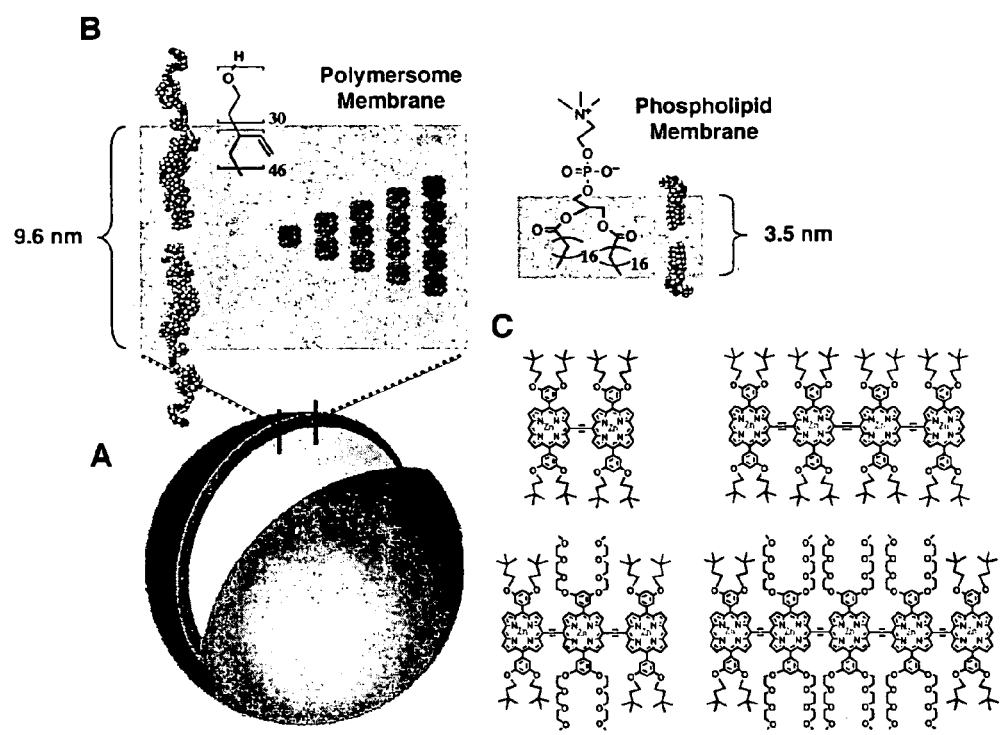
FIG. 1 illustrates the incorporation of some useful porphyrin-based near infrared fluorophores (NIRFs) into polymerosme membranes. Schematic A illustrates the ability of polymersomes to accommodate the loading of a subset of these multimeric porphyrin compounds that possess a meso-to-meso ethyne-bridged linkage topology; these di-, tri-, tetra-, and penta-PZn structures ($PZn_2$-$PZn_5$, see also schematic C) span peak emission wavelengths of 723, 809, 867, and 900 nm, respectively, within the polymersomal matrix. Schematic B, however, illustrates loading problems of large $PZn_3$-$PZn_5$ species in a conventional cell or liposome membrane composed of phospholipids.

In certain aspects, the invention concerns polymersomes composed of amphiphilic block copolymers that include fluorophores in their hydrophobic membranes. Some preferred polymersomes have diameters in the range of from about 50 nm to about 50 μm. In addition, in some preferred embodiments, the polymersome surface is modified with biological moieties to improve selectivity. These polymersomes can be used in vitro and in vivo to probe sample materials from cells, biological fluids, and tumor specimens for altered and novel gene products. Specific interactions between the polymersomes and rare-variants of bio-molecules present in small quantities can be identified and effectively isolated by the unique optical signal arising from the polymersome membrane. Additionally, nanometer sized polymersomes, composed of fully bioresorbable polymers encapsulating near infrared (NIR) fluorophores, and modified to target uniquely expressed/patient-specific bio-markers, can be used in vivo to monitor the function of proteins and genetic pathways, as well as the presence of cells marking pre-clinically active or residual disease.

The magnitude of any fluorescent signal will depend upon the local fluorophore concentration, the emission dipole strength per fluorophore, and the degree of local excitation. Such emissive signals will be attenuated by chromophore-chromophore and chromophore-local environment interactions that introduce additional non-radiative decay pathways or give rise to new low-lying non-emissive electronic states. Hence, optimizing fluorophore photophysics, regulating the average fluorophore-fluorophore interspatial separation, and delivering an appropriately large payload of emitters to a specific site, are all challenges that must be addressed in parallel when designing new photonic beacons for in vivo imaging applications. Further, a biocompatible fluorophore delivery platform must be not only physiologically stable with appropriately long circulation times but also small and deformable in order to pass through highly vascularized tissues. The compositions of the instant invention achieve these requirements and provide a deep-tissue optical imaging platform.

Dependent upon the structure of their component copolymer blocks, polymersome membranes are also significantly thicker (~9-22 nm) than those of liposomes comprised of natural phospholipids (3-4 nm) (see H. Bermudez, A. K. Brannan, D. A. Hammer, F. S. Bates, D. E. Discher, *Macromolecules* 35, Oct. 8, 2002; 8203-8208). These thick membranes of synthetic vesicles not only exhibit enormous mechanical stability, but as we demonstrate here, also provide sufficient size to solubilize and stably incorporate large hydrophobic compounds. Depending on the size of the vesicles composite amphiphilic building blocks, hydrophobic compounds of any size and molecular weight can be easily incorporated in polymersome membranes. Large (greater than 2 nm in size is 1 kD in MW) hydrophobic compounds (like porphyrin dimers, trimers, tetramers, pentamers) are unable to be accommodated in natural sized membranes composed of phospholipids.

Polymersomes

Polymersomes are constructed using block copolymers which are macromolecules that are comprised of two or more polymer blocks differing in composition that are generally covalently bonded. Diblock copolymers typically comprise two covalently bonded polymer blocks differing in composition. In amphiphilic block copolymers, the two blocks have very different interactions with water. Amphiphilic diblock copolymers generally have one block soluble in water, and the other block essentially water insoluble.

A wide variety of biodegradable and biocompatible polymers can potentially be utilized as polymer segments in polymersomes. These include the following where FDA approved biodegradable polymers are indicated with a "*": *polyglycolides (PGA), *polylactides (LPLA and DPLA), *polycaprolactone, *polydioxanone (PDO of PDS), *poly(lactide-co-glycolide) (PGA-LPLA), *polyanhydrides, *polyorthoesters, *poly(amino acids) and "pseudo"-poly (amino acids), *polyhydroxybutyrate(PHB), *polyhydroxyvalerate(PHV); polycyanoacrylates, polyphosphazenes, polyphosphonates, polyiminocarbonates, polyamines, polyolefins, polystyrene, polyoxyethylene, thermoset amino proteins, polysaccharides, polymethylmethacrylate (PMMA), polytetrafluoroethylene (PTFE), polyurethane, polyvinylchloride (PVC), polydimethylsiloxane (PDMS), polyesters, nylons, lignin-based biodegradable polymers, biodegradable polymers from soybeans, soy protein-based plastics, loose fill from corn, polymers based on synthetic genes, and bacterially-produced polymers such as polyhydroxyalkanoates. Biodegradable polymersomes are discussed in several publications (Meng, et. al., *Macromolecules* 36, 2003; 3004. F. Najafi, M. N. Sarbolouki, *Biomaterials* 24, Mar., 2003; 1175-1182).

In some embodiments, the hydrophilic polymer block is characterized as a composition that has a positive free energy change of transfer from water to a non-polar solvent such as hexane, cyclohexane, pentane, or toluene, relative to the free energy change for transferring glycine from water to the same non-polar solvent (see Radzicka, A. & Wolfenden, R., *Biochemistry* 26, 1664 (1988)). Some hydrophilic polymers comprise ionically polymerizable polar units. Ionically polymerizable polymers may be derived from units of one or more alkyl oxide monomers. In certain embodiments, the alkyl oxide monomers can be ethylene oxide, propylene oxide, or combinations thereof. In one particularly preferred embodiments, the hydrophilic polymer block comprises poly(ethylene oxide). In yet other embodiments, the volume fraction of the hydrophilic polymers in the plurality of amphiphilic block copolymers is typically less than about 0.40.

In some embodiments, the hydrophilic polymer block is a polyalkylene glycol. In certain embodiments, the polyalkylene glycol suitable for the hydrophilic component in the block copolymer of the present invention is polyethylene glycol, monoalkoxy polyethylene glycol, monoacyloxy polyethylene glycol, or any combination thereof.

In certain preferred compositions, the number average molecular weight of the hydrophilic polymer block in the range of 200 to about 20,000 Daltons, and, in some embodiments, preferably in the range of about 1,000 to about 15,000 Daltons. For some compositions, the content of the hydrophilic component is within the range of about 40 to about 80 weight percent, and in some embodiments, preferably about 40 to about 70 weight percent, based on the total weight of the block copolymer. In certain embodiments the content of the hydrophilic component may be less than about 40 weight percent of the block copolymer. In some embodiments a hydrophilic homopolymer having a molecular weight about the same as the amphiphilic block can be added to the amphiphilic block copolymer to form the polymersomes. In other embodiments, the weight ratio of the hydrophilic homopolymer to the hydrophilic block can be in the range of from about 20:80 to about 80:20, as long as the overall hydrophilic content of the homopolymer and block is within the range of about 40 to about 80 weight percent, and in some embodiments, preferably about 40 to about 70 weight percent, based on the total weight of the block copolymer and homopolymer.

In certain embodiments, the hydrophobic polymer is characterized as being insoluble in water. In some embodiments, the hydrophobic polymer is characterized as a composition having a negative free energy change of transfer from water to a non-polar solvent such as hexane, cyclohexane, pentane, or toluene, relative to the free energy change for transferring glycine from water to the same non-polar solvent (see Radzicka, A. & Wolfenden, R., *Biochemistry* 26, 1664 (1988)). Some preferred hydrophobic polymers include polyethylethylene, poly(butadiene), poly(β-benzyl-L-aspartate), poly (lactic acid), poly(propylene oxide), poly(ε-caprolactam), oligo-methacrylate, and polystyrene. In yet other embodiments, the hydrophobic polymer comprises polymerized units selected from ethylenically unsaturated monomers, such as poly(isoprene) ("PI") and polyethylenepropylene ("PEP").

In certain of these embodiments, the ethylenically unsaturated monomers are hydrocarbons. In certain preferred embodiments, the hydrophobic polymer comprises polyethylethylene or poly(butadiene).

In yet other embodiments, the hydrophobic polymer component may be a biodegradable block including polylactides, polycaprolactone, copolymers of lactide and glycolide, copolymers of lactide and caprolactone, copolymers of lactide and 1,4-dioxan-2-one, polyorthoesters, polyanhydrides, polyphosphazines, poly(amino acid)s or polycarbonates. In certain embodiments, the molecular weight of the hydrophobic polymer component is preferably within the range of about 500 to about 20,000 Daltons, and, in some preferred embodiments, from about 1,000 to about 10,000 Daltons.

Polymersomes are constructed using block copolymers which are macromolecules that are comprised of two or more polymer blocks differing in composition that are generally covalently bonded. In certain embodiments, the polymer may contain a fluorocarbon block that is characterized as being insoluble in water. In some embodiments, the fluorocarbon polymer is characterized as a composition having a negative free energy change of transfer from a fluorocarbon phase to water as well as a negative free energy change of transfer from a fluorocarbon phase to a non-polar solvent such as hexane, cyclohexane, pentane, or toluene, relative to the free energy change for transferring glycine from water to the same non-polar solvent (see Radzicka, A. & Wolfenden, R., *Biochemistry* 26, 1664 (1988)). Some preferred fkuorocarbon polymers include perfluoinated derivatives of polyethylethylene, poly(butadiene), poly(P-benzyl-L-aspartate), poly(lactic acid), poly(propylene oxide), poly(ε-caprolactam), oligo-methacrylate, and polystyrene. In yet other embodiments, the fluorocarbon polymer comprises polymerized units selected from extensively fluorinated unsaturated monomers, such as poly(fluoroisoprene) ("PI") and poly(fluoroethylenepropylene) ("PEP").

Some preferred polymersomes comprise poly(ethylene oxide)-polyethylethylene, poly(ethylene oxide)-poly(butadiene), or poly(ethylene oxide)-poly(lactic acid) block copolymers. Other polymersomes include block copolymers disclosed in U.S. Pat. No. 6,569,528 which comprising polyethylenimine as a hydrophilic block and aliphatic polyesters as a hydrophobic block and poly(oxyethylene)-poly(oxypropylene) block copolymers disclosed in U.S. Pat. No. 6,060,518.

As used herein, PEO is polyethylene oxide, PEE is polyethylethene, PB or PBD is polybutadiene. PEE is typically provided by catalytic hydrogenation of butadiene polymers that include more than about 50 percent of the butadiene repeat units in the 1,2 configuration. Catalytic hydrogenation of 1,2 polybutadiene is described by J H Rosedale et al., *J. Am. Chem. Soc.* 110, 3542 (1988), and U.S. Pat. No. 5,955,546.

Figure 3:
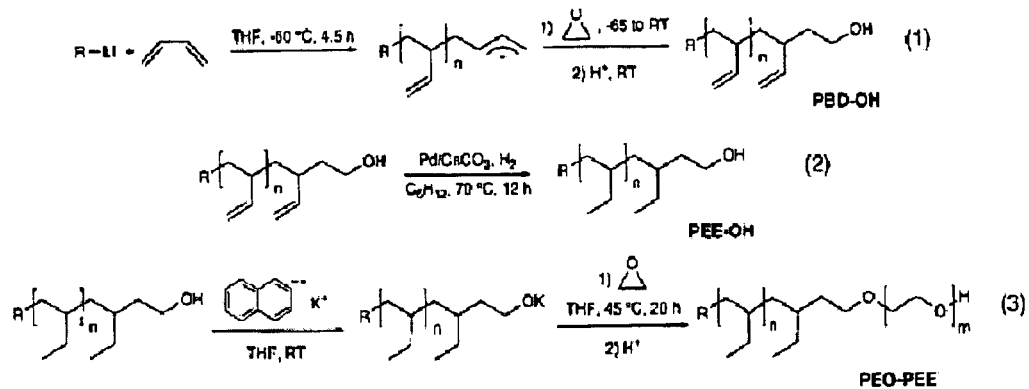
FIG. 3 shows a synthetic route for making PEO-PEE.

The synthesis of a certain PEO-PEE composition is illustrated in FIG. 3. In step 1, butadiene is cross linked. In step 2, PB-OH is catalytically hydrogenated to PEE-OH. In step 3, ethylene oxide is polymerized to the hydroxy terminal end of the polymer. By omitting the hydrogenation step 2, PEO-PB is produced. See, Hillmyer M A, Bates F S, *Macromolecules*, 29, 6994 (1996).

The polymersomes of the instant invention typically self-assemble into unique structures in melts (pure polymer solutions) and in aqueous mixtures. While not wanting to be bound by any particular theory of operation, it is believed that thermodynamics (entropic effects arising from non-covalent forces—ionic, hydrogen bonding, Van der Waals interactions) drives the self assembly of the block copolymers into these unique structures; structures such as lamellar phases (alternating layers of polymer blocks) or aqueous spherical (or rod like or worm-like) micelles, in which all of the molecules are clustered in a sphere in a single layer, with the hydrophilic parts pointed outward and the hydrophobic domains pointed inward, vary, inter alia, with molecular weight, chain conformation, and chemistry of the polymer. The solubility of the block copolymers is characterized generally by the overall interaction parameter $\chi$, which is a relative mixing parameter; higher values of $\chi$ typically lead to more immiscible systems, and a greater tendency of the polymers to strongly segregate into structured phases. The other parameter is the composition of the block copolymer—the volume fraction of each block in the vesicle membrane. The phase of matter formed by the polymers depends in a complex way upon total polymer molecular weight, block composition, polymer conformation, the mixing parameter $\chi$, temperature, and solvent. The phase behavior of polymer systems has been of much interest to synthetic and physical chemists, and is typically probed using techniques that include rheometry, optical microscopy, cryo-transmission electron microscopy (cryo-TEM), X-ray scattering and neutron scattering. See, for example, J H Rosedale and F. Bates, *Macromolecules* 1990 23:2329-2338, Hajduk D A, Kossuth M B, Hillmyer M A, Bates F S, *J. Phys. Chem. B* 1998; 102:4269-4276 and Hillmyer M A, Bates F S, *Macromolecules* 1996; 29:6994-7002.

The structural properties of $C_{18}$ phospholipid and several polymersomes are presented in Table 1.

TABLE 1

| Amphiphile | | Mn (g/mol) | PEG length (Da) | $f_{hydrophioic}$ (v/v) | $D_{core}$ (nm) (±1 nm) |
|---|---|---|---|---|---|
| SOPC | $C_{18}$ phospholipid | 790 | 0 | 0.31 | 3 |
| OB2 | $EO_{26}$-$DB_{46}$ | 3600 | 1200 | 0.28 | 9.6 |
| OE7 | $EO_{40}$-$EE_{37}$ | 3900 | 1840 | 0.39 | 8.0 |
| OB16 | $EO_{50}$-$BD_{54}$ | 5200 | 2300 | 0.37 | 10.6 |

TABLE 1-continued

| Amphiphile | | Mn (g/mol) | PEG length (Da) | $f_{hydrophioic}$ (v/v) | $D_{core}$ (nm) (±1 nm) |
|---|---|---|---|---|---|
| OB18 | $EO_{80}$-$DB_{130}$ | 10,400 | 3680 | 0.29 | 14.8 |
| OE21 | $EO_{40}$-$EE_{37}$ | 3900 | | 0.39 | | where Mn is number-average molecular weight, $f_{hydrophioic}$ is the hydrophilic volume fraction, and $D_{core}$ is the hydrophobic core thickness. See H. Bermudez, A. K. Brannan, D. A. Hammer, F. S. Bates, D. E. Discher, Macromolecules 35, Oct. 8, 2002; 8203–8208 for more detail. Additional polymer blocks utilized in currently available polymersome formulations can be found in Meng, et. al., Macromolecules 36, 2003; 3004.

Biological cells are surrounded by lipid membranes and the material strength of these membranes is enhanced by an underlying cytoskeleton. In live cells, the cytoskeleton generates an underlying cortical tension, which prevents deformation until a minimum applied tension is reached. It is possible to modulate the toughness and stability of polymersomes in further mimicry of cells if the polymer bilayer is subsequently cross-linked to form a robust polymer network. Using unsaturated poly(1,2 butadiene)-b-poly(ethylene oxide (OB) polymers, polymersomes can be crosslinked to form solid networks which, if the concentration of cross linkable polymer is sufficiently high, can greatly increase the critical tension required to cause the vesicle to fail. A vesicle made with 100% cross linkable OB polymer has a 100-fold greater critical tension than an OE-7 fluid vesicle. The strength of the membrane can be tuned by changing the percentage of cross-linkable polymer in the membrane, with the strength increasing monotonically with % cross-linkable polymer beyond 10%. Cross-linked polymersomes may be dried and rehydrated without rupture, as well as withstand large shear forces without breaking. Thus, polymer synthetic chemistry allows us to explore a much wider range of vesicle material properties than can be explored with phospholipids. For further discussion, see, for example, B. M. Discher et al., *Journal of Physical Chemistry B* 106, Mar. 21, 2002; 2848-2854).

$EO_{40}$-$EE_{37}$ (OE7) and $EO_{26}$-$BD_{46}$ (OB2) can synthesized according to Hillmyer M A, Bates F S, *Macromolecules*, 29,6994 (1996). The synthesis of these compositions is illustrative of other diblock compositions. The distribution of polymer molecular weights can be determined by gel permeation chromatography (GPC) in chloroform relative to polystyrene standards and is specified by the number average and weight-to-number average molecular weights. An important feature of these synthetic polymers—in comparison to natural lipids that make up bio-membranes—is the range of their respective molecular weight distributions. Phosphotidylcholines are the predominant phospholipids in this membrane at about 20% by total lipid weight, followed by sphingomyelin, phosphoethanolamine, and others. However, the two fatty acid chains in any given phospholipid can be very different and range from saturated 16-carbon chains to highly unsaturated 24-carbon chains. What results is a finite polydispersity in natural membranes which we calculate here for the measured phosphotidylcholines together with phosphoethanolamine components to be Mw/Mn~1.001.

This Mw/Mn is a lower bound which ignores not only the other uncharacterized phospholipids but also cholesterol (about 20% by weight of the membrane) and embedded integral membrane proteins, neither of which are membrane-forming amphiphiles in themselves. Nonetheless, a standard measure of width w=(Mw/Mn–1)½ indicates that the OE7 molecular weight distribution normalized by its mean is about 10 times that of the illustrated natural phospholipid distributions. OE7 has a robust tendency to self-organize into vesicles despite the disparity in w.

Polymersomes can encapsulate macromolecules just as liposomes, but unlike many pure liposome systems, however, polymersomes exhibit little or no in-surface thermal transitions. Notably, a subpopulation of polymersomes even survives autoclaving. Suspension in blood plasma has no immediate adverse effects on vesicle stability, and neither adhesion nor stimulation of phagocytes is apparent when giant polymersomes are held in direct, protracted contact. Proliferating cells, in addition, are unaffected when cultured for an extended time with an excess of polymersomes.

Without being bound by a particular theory of operation, it is believed that the stability of polymersomes increases with increased values of the product of the interaction parameter, $\chi$ and the statistical segment length scaled value of degree of polymerization, N, as described in U.S. Pat. No. 5,955,546. Typically, the value of $\chi N$ is kept greater than about 15, typically greater than about 20, and even more typically greater than about 25. Likewise, as the value of $\chi N$ of the diblock copolymers decreases, the polymersomes decrease in stability. Because $\chi N$ typically varies inversely with temperature, polymersomes can be designed to become unstable, thereby releasing their agent contents at a particular temperature.

In certain preferred embodiments, the hydrophobic component in the polymersome membranes is especially large (greater than 2 nm in size and 1 kD in MW) and is able to accomidate hydrophobic compounds (like porphyrin dimers, trimers, tetramers, pentamers) that are not suitable for liposome membranes.

Preparation of Polymersomes

Polymersomes can be prepared and processed by a number of methods known to one skilled in the art. These processes are analogous to techniques commonly practiced in the preparation of liposomes and include film rehydration, sonication, extrusion, mechanical shaking, freeze drying, freeze thawing, micro-emulsification, solvent dispersion, pH-induced vesiculation, ion/enzyme/ligand induced fusion, water-in-organic phase, double emulsion, reverse-phase evaporation and detergent solubilization techniques (see R. R. C. New, *Liposomes: A Practical Approach*. D. Rickwood, B. D. Hames, Eds., The Practical Approach Series; Oxford University Press, Oxford, UK, 1997). Giant vesicles of OE7 and OB2 spontaneously bud off of either rehydrated films or bulk copolymer. Electroformation of OE7, in which thin films are formed on two parallel platinum wires by chloroform evaporation, requires an oscillating voltage of somewhat higher amplitude (10 V, 10 Hz) than typically used for phospholipids such as SOPC (3 V, 1-10 Hz) to drive the budding process. The necessity of a higher driving voltage in electroformation likely reveals a higher lamellar viscosity. This is also manifested in relatively slow dynamics of osmotically induced vesicle shape changes of the sort described by in Discher, B. M.; Won, Y. Y.; Ege, D. S.; Lee, J. C.; Bates, F. S.; Discher, D. E.; Hammer, D. A., *Science* 284, 1143-1146 (1999).

Solutions of block copolymers used for vesicle formation, depending on the process used, can range from pure water to 250 mM sucrose or physiological PBS. Although unilamellar vesicles predominate in electroformed preparations, multilamellar vesicles that exhibit an enhanced edge contrast also have a tendency to form in the various methods. The passage of vesicles through a filter with pores of 0.1 mm diameter can be used, with or without sonication and freeze-thaw, to generate a very narrow distribution of vesicle sizes with retained contents. Multi-generational polymersomes, i.e., smaller polymersomes within larger polymersomes, are also prepared by these methods.

Because of certain similarities in mechanical properties between polymersomes prepared by various methods, no further process distinction has been made in characterizations such as long-term stability. In formal studies as well as more casual observation, it has been observed that polymersomes in dilute suspension maintain their contents and a stable size distribution for a month or longer. In contrast, it has been found that SOPC vesicles suspended under the same conditions lose their phase contrast within a day: nominally, $t_{1/2} \sim 10$-$20$ hours. Because the stability of a copolymer structure such as the lamellar phase is well appreciated as depending on the product of the Flory interaction energy, $\chi$, and chain length, N, one would expect that the polymersomes are not only more stable mechanically but also that they have a much lower critical micellization concentration (CMC) than lipids, given the same $\chi$.

In certain embodiments, the block co-polymer assemblies of the instant invention can have cross-linking. Cross-linking can stabilize to polymersome structure. For example, Ahmed, et al, Langmuir 19, 6505 (2003) have studied amphiphilic diblocks comprising hydrophilic poly(ethylene oxide) and cross-linkable hydrophobic polybutadiene. Cross-linkable compositions can be blended with non-cross-linkable compositions in certain embodiments. Vesicles constructed of cross-linked bock copolymers can be dehydrated and rehydrated without compromising the polymersome structure. See Discher, et. al, *J. Phys. Chem. B*, 106, 2848 (2002). This feature is advantageous in producing, storing, and later using polymersome compositions in end uses such as imaging, diagnostics, and therapeutics.

Targeting Moieties

By utilizing a targeting moiety that can direct the polymersome to a particular cell type, tissue, or location, the polymersomes of the invention become more effective, discriminatory and selective. The term "targeting moiety" is defined herein as a functional group which serves to target or direct the polymersome to a particular location, cell type, organ, diseased tissue, or other targeted cell sites. In some preferred embodiments, the targeting moiety is an antibody, cell surface receptor ligand, hormone, lipid, sugar, dextran, alcohol, bile acid, fatty acid, amino acid, peptide or nucleic acid. The targeting moiety can be attached to the amphiphilic block copolymer using linking chemistry techniques known to those skilled in the art. In some embodiments, the targeting moiety is covalently bound to the block copolymer. In some embodiments, the targeting moiety is bound to the hydrophilic polymer. In other embodiments, the targeting moiety is associated with the polymersome by non-covalent bonding interactions such as ionic or by van der Waals forces. In certain preferred embodiments, the targeting moiety is comprises an antibody, antibody fragment, or a receptor binding site or substance. In yet other embodiments, the receptor binding site or substance comprises a receptor-specific peptide, carbohydrate, or protein. The terminal hydroxyl of a hydrophilic block, for example, can be modified with biotin-Lysine (biocytin), a biologically derived group that imparts specific adhesiveness to a polymer colloid coated with avidin. This functionalized polymer forms vesicles, either on its own, or when mixed with unmodified block copolymers that also form vesicles.

Figure 4:
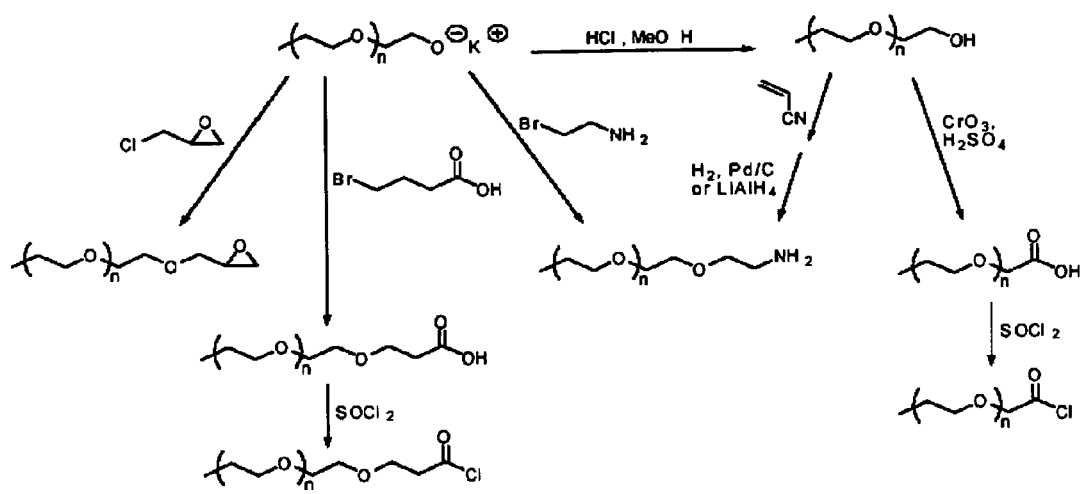
FIG. 4 illustrates a synthetic strategy for functionalizing polymersomes.

One strategy to modify the surface of the block copolymersome is shown in FIG. 4. In some embodiments, the terminal end of a water-soluble polyethylene oxide is the most attractive location for substitution, due to the specificity of the location for chemical modification and the subsequent availability of the substituted ligand for physical interaction with a surface. Numerous chemical transformations are possible beginning with the terminal alcohol (see, for example, Streitweiser A, Heathcock C H, Kosower E M. *Introduction to Organic Chemistry*, New York: Macmillan Publishing Co. (1992)). For example, reaction of PEO-OH with acrylonitrile and subsequent protonation converts the terminal group to a primary amine. The reaction conditions are typically compatible with the overall polymer chemistry, and several such reactions will be optimized for application to the block copolymers described below. Techniques for attaching biological molecules to a wide variety of chemical functionalities have been catalogued by Hermanson, et al., Immobilized Affinity Ligand Techniques, New York, N.Y.: Academic Press, Inc. (1992).

The targeting moiety is optionally attached to the polymersome by a linking group. Suitable linking groups are those that provide a desired degree of flexibility without any detrimental effects to the polymersome/imaging agent system.

Imaging Agents

The polymersome compositions of the instant invention comprise at least one visible- or near infrared-emissive agent that is dispersed within the polymersome membrane. In certain embodiments, the emissive agent emits light in the 700-1100 nm spectral regime. In other embodiments, at least one emissive agent comprises a porphyrin moiety. Other emissive agents include a porphycene-, rubyrin-, rosarin-, hexaphyrin-, sapphyrin-, chlorophyll-, chlorin-, phthalocynine-, porphyrazine-, bacteriochlorophyll-, pheophytin-, or texaphyrin-macrocyclic-based component, or a metalated derivative thereof.

The emissive agent may be a laser dye, fluorophore, lumophore, or phosphor in certain embodiments. A laser dye according to the invention is any organic, inorganic, or coordination compound that has the ability to lase. Suitable laser dyes include those found in Birge, R R, Duarte, F J, Kodak Optical Products, Kodak Publication JJ-169B (Kodak Laboratory Chemicals, Rochester, N.Y. (1990). Representative laser dyes include p-terphenyl, sulforhodamine B, p-quaterphenyl, Rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HIDC iodide, coumarin 151, PTPC iodide, coumarin 4, cryptocyanine, coumarin 314, DOTC iodide, coumarin 30, HITC iodide, coumarin 500, HITC perchlorate, coumarin 307, PTTC iodide, coumarin 334, DTTC perchlorate, coumarin 7, IR-144, coumarin 343, HDITC perchlorate, coumarin 337, IR-NO, coumarin 6, IR-132, coumarin 152, IR-125, coumarin 153, boron-dipyrromethere, HPTS, flourescein, rhodamine 110, 2,7-dichlorofluorescein, rhodamine 65, and rhodamin 19 perchlorate, rhodamine b, where the laser dye is modified by addition of a hydrophobic substitutent, and the laser dye being substantially dispersed within the polymersome membrane.

In some embodiments, The emissive agent is a near infrared (NIR) emissive species that such as a di- and tricarbocyanine dye, a croconium dye, or a thienylenephenylenevinylene species substituted with electron withdrawing substituents, where the emissive species is modified by addition of a hydrophobic substituent, the NIR dye being substantially dispersed within the polymersome membrane.

Hydrophobic moieties and means for attaching them to various chemical structures are well known to those skilled in the art. In some embodiments, the hydrophobic substitutent is a lipophilic group. Lipophilic groups include alkyl groups, fatty acids, fatty alcohols, steroids, waxes, fat-soluble vitamins, and the like. Other lipophilic substitutents include glycerides, glyceryl ethers, phospholipids, and terpenes.

Numerous examples of electron-donating and electron-withdrawing groups are well-known to those skilled in the art. (See, e.g., Gordon, et al., *The Chemist's Companion*, New York, John Wiley & Sons, 1972). Representative electron-withdrawing groups include appropriately-substituted alkyl and aryl groups (such as haloalkyl groups), $N$-(alkyl)$_3^+$, $S$-(alkyl)$_2^+$, $NH_3^+$, $NO_2$, $SO_2$-(alkyl), $CN$, $SO_2$-(aryl), $C(O)OH$, F, Cl, Br, I, cyclopentadienyl, $C(O)O$-alkyl, $C(O)$-(alkyl), CHO, and heterocycles such as N,N'-diethylthiobarbituric acid, 3-phenyl-5-isoxazolone, quinone, 4-pyridyl, and 3-pyridyl groups.

In certain preferred embodiments, the imaging agent is dispersed within the polymersome membrane. For some imaging agents, attachment of a hydrophobic substituent to the agent improves the dispersion within the membrane. Identification and attachment of such groups is well within the ability of those skilled in the art.

Those skilled in the art will recognize the wide variety of dimers, trimers, oligomers or polymers that can be prepared from the porphyrin-containing compounds of the invention. For instance, somewhat linear polymer chains can be formed wherein a portion of the polymer has general formula $(PN)_r$, where PN is a porphyrin unit and r is at least 2. In further embodiments, linear polymer chains have general formula:

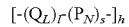

where $Q_L$ is a linking group, $P_N$ is a porphyrin unit, and h, l, and s are independently selected to be at least 1. For example, a portion of such polymers can have formula:

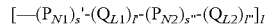

wherein $P_{N1}$ and $P_{N2}$ are independently selected porphyrin units, $Q_{L1}$ and $Q_{L2}$ are independently selected linking groups, and l', l'', s', and s'' are at least 1. These essentially linear polymer chains can be cross-linked such that a portion of the polymer has general formula:

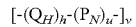

wherein $Q_H$ is a linking group, and h, u, and v are independently selected to be at least 1. A portion of these cross-linked polymers can have formula:

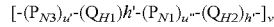

wherein $P_{N3}$ is a porphyrin unit, $Q_{H1}$ and $Q_{H2}$ are independently selected linking groups, and h', h'', u', and u'' are at least 1.

The porphyrin oligomers of the invention are generally formed by contacting a substituted porphyrin with a second compound containing functionality that is reactive with the functionality contained within the porphyrin. In some embodiments, the porphyrin preferably contains an olefinic carbon-carbon double bond, a carbon-carbon triple bond or some other reactive functionality. The contacting should be performed under conditions effective to form a covalent bond between the respective reactive functionalities. In some embodiments, porphyrin-containing polymers are preferably formed by metal-mediated cross-coupling of, for example, dibrominated porphyrin units. Also, porphyrin-containing polymers can be synthesized using known terminal alkyne coupling chemistry. (see, e.g., Patai, et al., The Chemistry of Functional Groups, Supplement C, Part 1, pp. 529-534, Wiley, 1983; Cadiot, et al., Acetylenes, pp. 597-647, Marcel Dekker, 1964; and Eglinton, et al., Adv. Org. Chem., 1963, 4, 225) As will be recognized, the second compound noted above can be a substituted porphyrin of the invention or some other moiety such as an acrylate monomer. Thus, a wide variety of copolymeric structures can be synthesized with the porphyrins of the invention. Through careful substituent selection the porphyrins of the invention can be incorporated into virtually any polymeric matrix known in the art, including but not limited to polyacetylenes, polyacrylates, polyolefins, pohyethers, polyurethanes, polycarbonates, polyanilines, polypyrroles, and polythiophenes. For example, fluorescent porphyrins can be incorporated into such polymers as end-capping groups or as a component of a hydrophobic, hydrophilic, or fluorinated polymer block noted above.

In some embodiments, the polymersomal emissive components derive from an oligo(porphyrin) structural motif that features cylindrically π symmetric bridging units that directly link juxtapose (phorphinato)zinc(II) (PZn) macrocycle frameworks. This mode of PZn-to-PZn connectivity modulates substantially ground- and excited-state interchromophore electronic interactions, enabling predictable tuning of the fluorescence emission energy of these chromophores over a large window of the visible and near infrared (NIR) spectral domains (600-950 nm).

Ethyne-elaborated porphyrins (porphyrins with one, two, and multiple acetylene units appended directly to the porphyrin periphery) represent one such class of chromophores. These species provide synthetic entry into arrays of conjugated macrocycles linked via ethynyl and butadiynyl bridges; these species exhibit unusually large ground-state electronic interactions, show record excitonic couplings, and possess optoelectronic properties in common with biological light-harvesting antenna systems that are composed of large numbers of chromophores. Increasing the conjugation length of the PZn-to-PZn moiety augments the low energy visible/NIR absorption oscillator strength and shifts both the absorption and corresponding emission maxima progressively toward the red end of the spectrum. For further detail, see V. S.-Y. Lin, S. G. DiMagno, M. J. Therien, *Science* 264, 1105-1111 (May 20, 1994); V. S.-Y. Lin, M. J. Therien, *Chemistry-a European Journal* 1, 645-651 (December, 1995); K. Susumu, M. J. Therien, Journal of the American Chemical Society 124, 8550-8552 (Jul. 24, 2002); and I. V. Rubtsov, K. Susumu, G. I. Rubtsov, M. J. Therien, *Journal of the American Chemical Society* 125, 2687-2696 (MAR 5, 2003).

FIG. 1 highlights a subset of these multimeric porphyrin compounds that possess a meso-to-meso ethyne-bridged linkage topology. These di-, tri-, tetra-, and penta-PZn structures ($PZn_2$ to $PZn_5$ structures respectivley) span peak emission wavelengths of 723, 809, 867, and 900 nm, respectively, within the polymersomal matrix. With respect to key NIR fluorophore (NIRF) requirements for optical imaging, note that $PZn_2$ to $PZn_5$ not only possess large NIR emission dipole strengths and substantial radiative rate constants (kr); but, they also exhibit low energy, high oscillator strength absorptive transitions that are ideally suited for facile NIR excitation (K. Susumu, M. J. Therien, *Journal of the American Chemical Society* 124, 8550-8552 (Jul. 24, 2002)). The thick polymersomes discussed herein are able to accommodate the large conjugated NIR fluorophore moieties.

Figure 2:
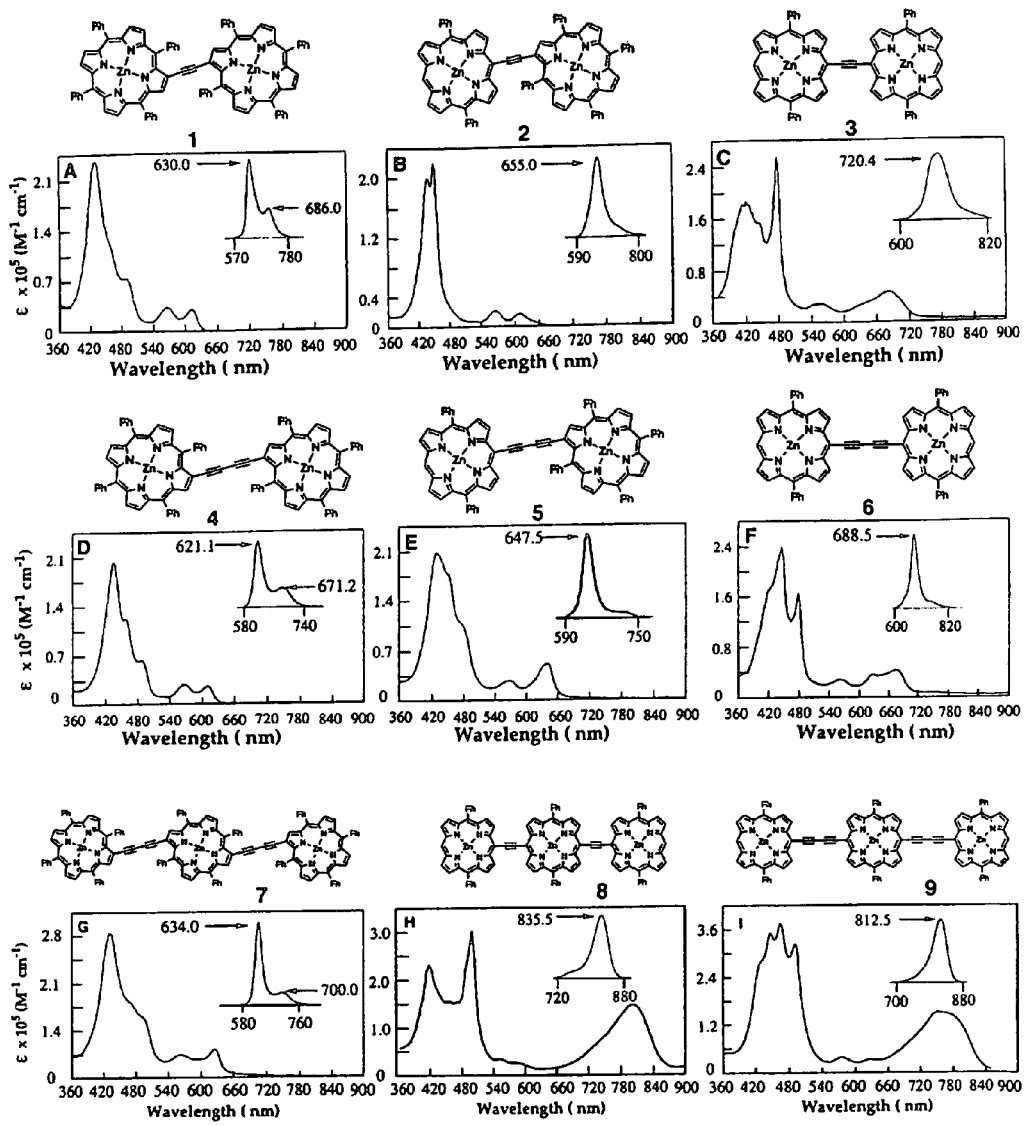
FIG. 2 shows the electronic absorption spectra of a number of conjugated porphyrin arrays. Various modes of PZn-to-PZn connectivity modulate substantially ground- and excited-state interchromophore electronic interactions, enabling predictable tuning of the fluorescence emission energy of these chromophores over a large window of the visible and NIR spectral domains (600-950 μm).

In certain embodiments, the phorphinato imaging agent is an ethynyl- or butadiynyl bridged bis or tris(phorphinato)zinc compound with a β to β, meso to β, or meso to meso linkage. In some preferred embodiments, the phorphinato imaging agent is capable of emitting in the 600 to 950 nm spectral regime. Some useful phorphinato imaging agents are shown in FIG. 2. The agents depicted in FIG. 2 show a "Ph" or phenyl group attached at various locations on the porphyrin ring. In some compositions useful in the instant invention, one or more phenyl groups are substituted. In some embodiments, substitutents can be $C_1$-$C_{12}$ alkyl, $C_1$-$C_{12}$ perfluoroalkyl $C_2$-$C_7$ alkenyl, halogen, polyethers, hydroxyl, $C_1$-$C_6$ alkoxy, CN, —$NO_2$, amino, $C_1$-$C_6$ alkylamino, dialkylamino of 1-6 carbon atoms per alkyl group, thio, $C_1$-$C_6$ alkylthio, $C_1$-$C_6$ alkylsulfinyl, $C_1$-$C_6$ alkylsulfonyl, $C_2$-$C_7$ alkoxycarbonyl, alkylcarbonyl, trifluoroalkoxy, benzylnitrile or benzoyl. In certain particularly preferred embodiments, the substitutent is a $C_1$-$C_{12}$ linear or branched alkyl. In other preferred embodiments, the substitutent is a $C_1$-$C_{12}$ branched alkyl. Suitable polyether substitutents include those of the formula:

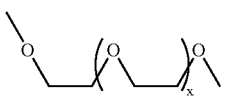

where x is 1 to about 10. In some embodiments, x is 1 or 2.

In some embodiments, the emissive agent is an emissive conjugated compound comprising at least two covalently bound moieties; whereby upon exposing the compound to an energy source for a time and under conditions effective to cause the compound to emit light at a wavelength between 700-1100 nm, is of an intensity that is greater than a sum of light emitted by either of covalently bound moieties individually. In other embodiments, the emissive agent is an emissive conjugated compound comprising at least two covalently bound moieties; whereby upon exposing the compound to an energy source for a time and under conditions effective to cause the compound to emit light that at a wavelength between 700-1100 nm, and exhibits an integral emission oscillator strength that is greater than the emission oscillator strength manifest by either one of the the moieties individually.

Certain useful imaging agents are found in V. S.-Y. Lin, S. G. DiMagno, M. J. Therien, *Science* 264, 1105-1111 (MAY 20, 1994); V. S.-Y. Lin, M. J. Therien, *Chemistry-a European Journal* 1, 645-651 (DEC, 1995); K. Susumu, M. J. Therien, *Journal of the American Chemical Society* 124, 8550-8552 (JUL 24, 2002); and I. V. Rubtsov, K. Susumu, G. I. Rubtsov, M. J. Therien, *Journal of the American Chemical Society* 125, 2687-2696 (MAR 5, 2003).

The invention also concerns a method of modulating the emission properties of a visible- or near infrared-emissive agent comprising at least two covalently bound moieties, the emissive agent being within a polymeric material, wherein at least one of the bound moieties comprises an ancillary substituent, the size and chemical constitution of said substituent being selected to provide the modulation. In some embodiments, the modulation is of the steady state emission wavelength. In other embodiments, the modulation is of the time-dependent emission dynamics of said emissive conjugated compound. This adjustment can be made in a predictable way. While not wanting to be bound by theory, it is believed that the electronic conjugation determines the precise wavelength of emission from linear porphyrin-oligomers. If the individual monomer units of a given oligomer are co-planar (i.e. the dihedral angle between the monomers is either 0 or 180 degrees), there is full delocalization of the 1-electron cloud across the monomer units such that the band-gap (energy difference) between the ground and excited states is decreased. The result is that both the lowest-energy absorbance and emission states of the porphyrin oligomer are less than the sum of its individual monomer units and its corresponding fluorescence emission is of lower energy (the wavelength is red-shifted compared to the emission of the porphyrin monomer). If porphyrin monomers are combined in linear series (such as a porphyrin dimers, trimers, tetramers or pentamers), the band-gap of successively longer oligomers is further decreased with the addition of each co-planar monomer unit; and, the emission wavelengths of the oligomer are correspondingly further red-shifted. The emission and absorbance wavelengths of a series of ethynyl- and butadiynyl-bridged bis-, tris-, and penta(porphinato) zinc chromophores have previously been shown to be rationally controlled by such manner in organic solution (see Lin and Therien, *Chem Eur. J.* 1995, 1, No. 9). The oligomer backbone were modified by altering the bridging-alkynes as well as the linkage-positions between various porphyrin monomers in order to control the extent of electronic-conjugation and specific absorption/emission properties of a given fluorophore in solution (see FIG. 2).

Figure 13:
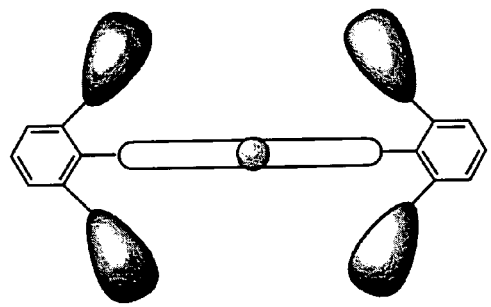
FIG. 13 shows the emission wave-length tuning of emissive polymersomes.
Figure 13:
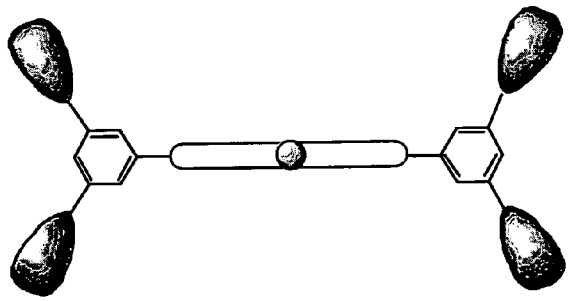
Figure 15:
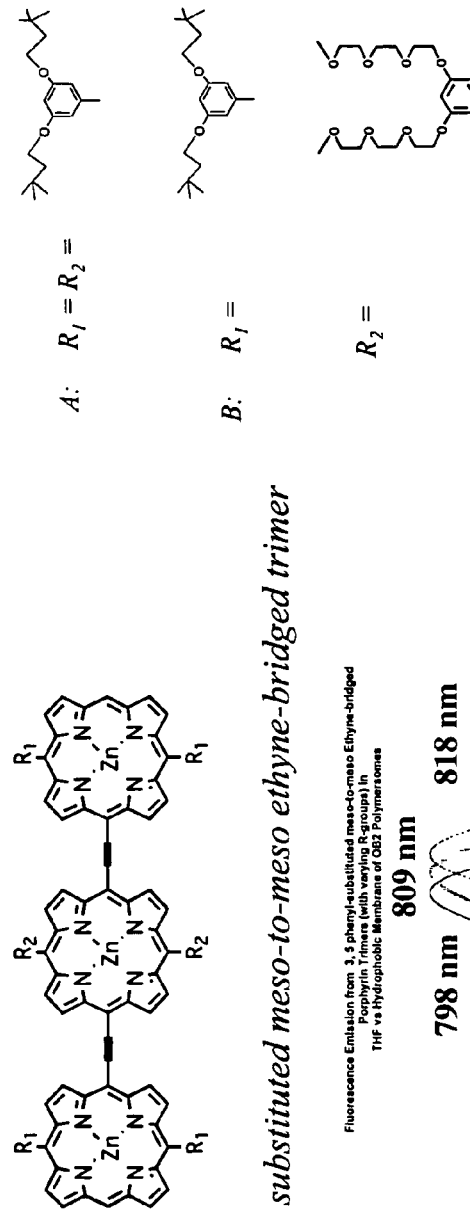
FIG. 15 shows the tuning of fluorescence emission by controlling the nature of the substituent groups.
Figure 16:
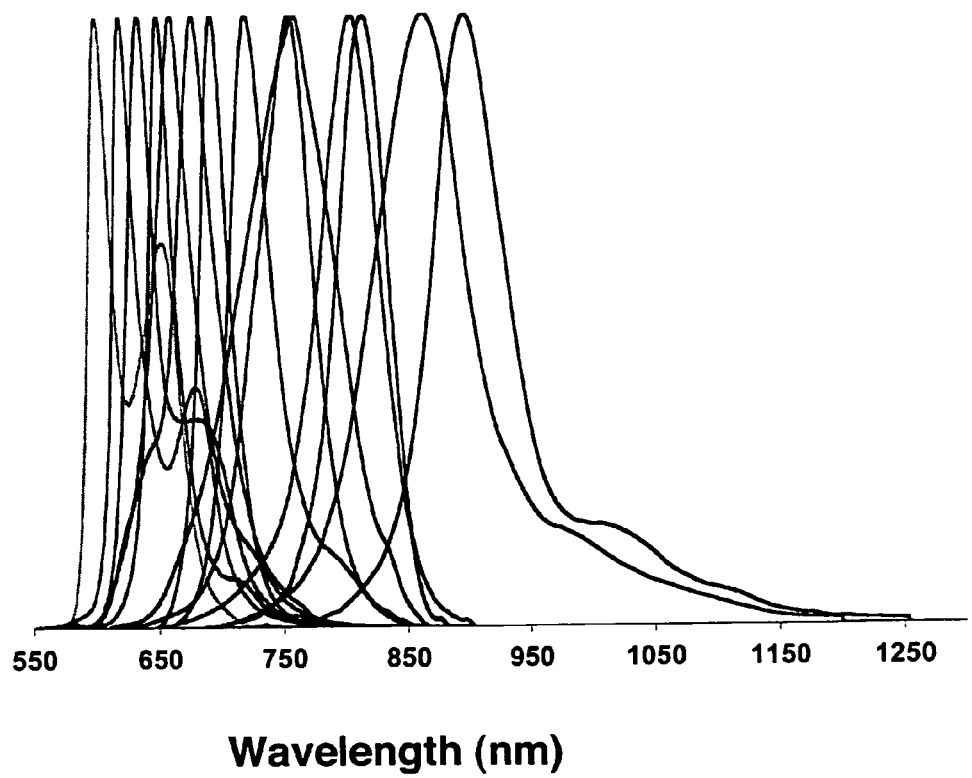
FIG. 16 shows the fluorescence wavelength tuning in NIR-emissive polymersomes.

Another level of control in the precise wavelength-tuning of fluorescence-emission based on the interaction of a polymersome-incorporated porphyrin-oligomer with polymer chains in its local membrane environment. As discussed herein, near-IR-emitting porphyrin-oligomers can be successfully inserted in the hydrophobic membranes of polymer bi-layered vesicles. Emission data from various polymersome-incorporated oligomers shows that not only the conjugation length and substituent stereoelectronic effects determine the wavelength of emission (as previously determined in organic-solution-based data), but also the nature of the interactions of the ancillary substituents of the emissive material with the polymeric matrix that define the polymersome membrane. Depending if the phenyl is substituted at the 2, 6 or at the 3, 5 positions, for example, a different local-interaction with polymer chains surrounding the fluorophore arises. Structurally, the 2, 6 substitution results in the substitutent groups being located above and below the plane of the porphyrin while the 3, 5 substitution has groups that are pointing away from the porphyrin oligomer's axis of conjugation (see FIG. 13).

In some embodiments, the substitution made in at least one of the 2, 3, 4, 5, or 6 positions of the fluorophore-pendant aryl ring ancillary substituents. In others, the substitution at the aryl ring ancillary substituents is at both the 3 and 5 positions. In certain other compositions, the substitution is at both the 2 and 6 positions.

In certain embodiments, such substitutions are made on each unit of the porphyrin-oligomer. In other embodiments, only some of the units comprise the substitution. For some compositions, the substituents are all the same. In other compositions, the substituents may vary from one subunit to another within the oligomer.

It is observed that 2, 6 substitution, with the resultant cylindrical-like geometry of the oligomer-species in the polymer membrane, results in twisting of the oligomer about its conjugation axis in the polymersome membrane due to the nature of the interactions of its ancillary substituents with the polymer chains such that electronic interactions between individual monomers are reduced. The outcome of this twisting is an increase in the band gap between the oligomer's ground and excited states and an overall increase in the energy of emission (blue-shift of the emission wavelength). The 3, 5 substitution, on the other-hand, appears to drive a different ancillary substituents-polymer chains interaction, and results in a flattening of the porphyrin-oligomer by interacting with the polymer chains in the membrane such that each monomer unit of the oligomer is in a more co-planar arrangement, and better electronically conjugated (lower band-gap), than is observed for the same compound in free organic solution. The result of this interaction is such that each 3,5-substituted oligomer has a red-shifted emission in polymersomes as compared for the same fluorophore in free organic solution.

Precise tuning of the absorbance and emissive state of a polymersome-incorporated fluorophore can be accomplished by designing an oligomer with different R-groups off the same locations of the phenyl rings of individual monomer units. In general, one can choose the R-groups (and their locations off the phenyl rings), in a rational manner, to twist the chromophore conjugation axis and thus statically control the optical properties of the assembly. It follows, however, that one can also, in a rational manner, dynamically alter the electronic conjugation between individual monomers in a given polymersome-incorporated porphyrin-oligomer by manipulating the polymer chains so as to vary the exact nature of their interaction with the fluorophore in a local environment.

Based on molecular structures of various linear oligomers, and the dihedral angle measurements between individual monomers (see Lin and Therien, *Chem Eur. J.* 1995, 1, No. 9), it is evident that the ethyne-linkage effectively locks two porphyrin monomers in a given orientation while the butadiyne linkage allows for a larger degree of reorientation. Additionally, a meso-to-meso linked oligomer has more potentially redundant individual monomeric arrangements as compared to a meso-to-beta linkage (greater degree of variability) or beta-to-beta linked porphyrins (greatest number of unique electronically-conjugated arrangements for the oligomer).

In some embodiments, a preferred structure is a beta-to-beta butadiyne-linked oligomer: for example, the tris(porphinato) zinc conjugated chromophore (see FIG. 2 structure number 7). For this oligomer in solution (at room temperature), each porphyrin monomer is oriented at a 90-degree angle with respect to another and is thus completely electronically un-conjugated: this state corresponds to the higher energy (634 nm) emission band seen in solution. Due to the butadiyne-linkage, however, the movement of individual monomer units is not hindered such that the monomers can come to lie in more co-planar, electronically-conjugated, orientations where the emission band of the oligomer is subsequently red-shifted: corresponding, for example, to the 700 nm emission band seen in the beta-to-beta linked butadiyne trimer in solution. This potential rearrangement of monomer units is ideally suited for manipulation by local polymer-chains around the fluorophore in the hydrophobic membrane of a polymersome.

In some embodiments, the substituents are independently $C_1$-$C_{20}$ alkyl, $C_1$-$C_{20}$ alkoxy, —O—$(CH_2)_m CO_2 R'$, —O$(CH_2)$—$(O(CH_2))_x$, or —O—$(CH_2)_p COH$, m and p are independently an integer from 1 to 10, x is an integer from 1 to 12, and R' is $C_1$-$C_{20}$ alkyl. In certain embodiments, the substituents are one of the moieties shown below.

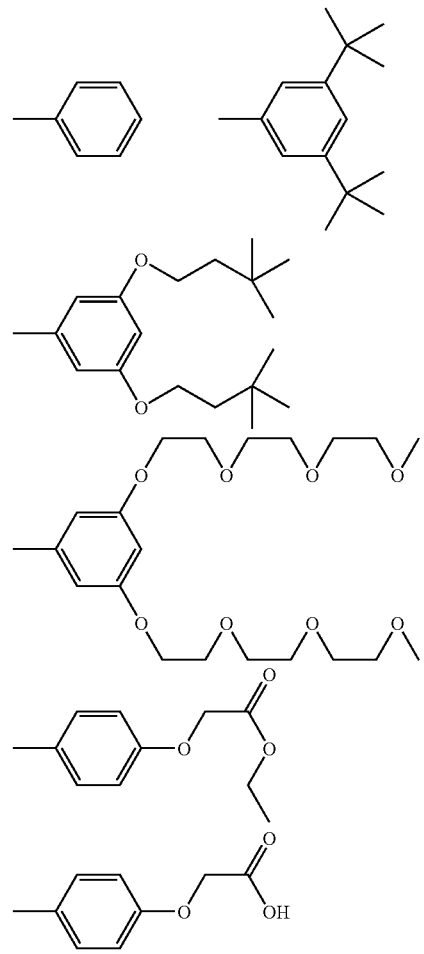

The shift in emission spectra for a variety of 3,5-substituted and 2,6-substituted porphyrin-oligomers are shown in FIGS. 12-16. In each case, emission data of the depicted porphyrin-oligomer is shown in THF solution and within the membrane of an OB2 polymersome.

DEFINITIONS

The term "alkyl", as used herein, whether used alone or as part of another group, refers to a substituted or unsubstituted aliphatic hydrocarbon chain and includes, but is not limited to, straight and branched chains containing from 1 to 20, in some embodiments, 1 to 12 carbon atoms, and in some preferred embodiments 1 to 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to 20 carbon atoms, and in some embodiments 2 to 8 carbon atoms, and containing at least one double bond. Preferably, the alkenyl moiety has 1 or 2 double bonds. Such alkenyl moieties may exist in the E or Z conformations and the compounds of this invention include both conformations. Specifically included within the definition of "alkenyl" are those aliphatic hydrocarbon chains that are optionally substituted. Heteroatoms, such as O, S or N—$R_1$, attached to an alkenyl should not be attached to a carbon atom that is bonded to a double bond.

"Aryl," as used herein, refers to an aromatic 5- to 13-membered mono- or bi-carbocyclic ring such as phenyl or naphthyl. Preferably, groups containing aryl moieties are monocyclic having 5 to 7 carbon atoms in the ring. Phenyl is one preferred aryl. In some embodiments, phenyl moieties are optionally substituted with $C_1$-$C_6$ alkyl, $C_2$-$C_7$ alkenyl, halogen, hydroxyl, $C_1$-$C_6$ alkoxy, —CN, —$NO_2$, amino, $C_1$-$C_6$ alkylamino, dialkylamino of 1-6 carbon atoms per alkyl group, thio, $C_1$-$C_6$ alkylthio, $C_1$-$C_6$ alkylsulfinyl, $C_1$-$C_6$ alkylsulfonyl, $C_2$-$C_7$ alkoxycarbonyl, of 2-7 carbon atoms alkylcarbonyl, trifluoroalkxoy, benzylnitrile or benzoyl.

"Heteroaryl", as used herein, means an aromatic 5- to 13-membered carbon containing mono- or bi-cyclic ring having one to five heteroatoms that independently may be nitrogen, oxygen or sulfur. Preferably, groups containing heteroaryl moieties are monocyclic having 5 to 7 members in the ring where one to two of the ring members are selected independently from nitrogen, oxygen or sulfur. Groups containing aryl or heteroaryl moieties may optionally be substituted as defined below or unsubstituted. Examples of heteroaryls include, but are not limited to, thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, or quinazolinyl.

The term "halogen" includes bromine, chlorine, fluorine, and iodine.

The term "alkoxy," as used herein, refers to the group R—O— where R is an alkyl group as is defined herein.

The term "perfluoroalkyl" refers to an alkyl group, as defined herein, that has each hydrogen atom replaced by a fluorine atom.

The term "peptide" as used herein means a linear compound that consists of two or more amino acids (as defined herein) that are linked by means of a peptide bond.

The term "lipid" as used herein is defined as an organic compounds substantially soluble in organic and not aqueous solvents. Examples include fats, waxes, steroids, phospholipids, carotenoids, and xanthophylls.

As used herein, "phospholipid" refers to amphipathic lipids with either a glycerol or a sphingosine backbone, fatty acid side chains and a phosphorylated alcohol terminal group. Phospholipids include glycerolipids, phosphatidylcholine, phosphatidylethanolamine, phosphatidylinositol, phosphatidylserine, and the sphingolipid sphingomyelin.

The term "steroid" as used herein refers to large class of organic compounds with a characteristic multicyclic structure containing three six-membered and one five rings of carbon atoms. Steroids include many hormones, alkaloids and vitamins.

"Surfactant" as used herein refers to compositions that lower the surface tension of a liquid in which it is dissolved. Surfactants contain both hydrophobic and hydrophilic components rendering them somewhat soluble in both organic and aqueous solvents. Soaps are but one example of a surfactant.

The term "bioresorbable" refers to a molecule, when degraded by chemical reactions, leads to substituents which can be used by biological cells as building blocks for the synthesis of other chemical species, or can be excreted as waste.

"Single chain alcohols" are used herein to describe an optional material added to the liposome refers to a molecule which terminates in a hydroxyl group (OH), the remainder of which is a hydrocarbon tail of any number of carbon and hydrogen atoms.

Methods

The utilization of near infra-red (NIR) probes in cancer prevention/detection strategies is attractive because: (i) light scattering decreases in the visible region with the reciprocal of the fourth power of wavelength ($\lambda$-4) to approach a minimum scattering based on $\lambda$-1 in the NIR spectral region; and (ii) the NIR spectral domain features a substantial optical window where hemoglobin and water absorption are minimal. The imaging agents of the invention are highly emissive NIR probes that permit an all-optical method for the detection, not only, of surface cancers, but small subsurface tumors as well. This is possible because the instant phorphinato agents are large emission dipole strength fluorophores capable of providing high contrast imaging and ultra-sensitive detection in vivo.

In addition, large numbers of porphyrin fluorophores can be loaded in the polymersomes of the instant invention. Loading dependence correlates with polymersome size such that a 100 nm polymersome holds about 1500 copies of the fluorophore. A 500 nm polymersome holds about 40,000 copies of the fluorophore while a 1 µm polymersome holds about 150,000 copies of the fluorophore. Thus the compositions of the instant invention provide high loading ability coupled with the strong fluorescence signal. Furthermore, the incorporation of large (>2.2 nm/2 KD), hydrophobic fluorophores at these large copy numbers in vesicles is only achievable for thick polymersome membranes and not possible in natural membranes composed of phospholipids.

Synthetic methodology relevant to the synthesis of porphyrins and related macrocycles enables facile elaboration of the porphyrin periphery through catalytic metal-mediated cross-coupling reactions. See, for example, DiMagno S G, Lin VS-Y, Therien M J, *J. Am. Chem. Soc.*, 115, 2513 (1993); DiMagno S G, Williams R A, Therien M J, *J. Org. Chem.*, 59, 6943 (1994); and Hyslop A G, Kellett M A, Iovine P M, Therien M J. Suzuki, *J. Am. Chem. Soc.*, 120, 12676 (1998).

In some aspects, one or more additional imaging agents may be used in the instant invention. Some of these agents are, for example, a secondary emitter, a cytotoxic agent, a magnetic resonance imaging (MRI) agent, positron emission tomography (PET) agent, or a photodynamic therapy (PDT) agent. These agent are well known to one skilled in the art. These compounds can be either hydrophilic (present in the aqueous interior) or hydrophobic (present in the thick membranes) for incorporation into polymersomes. The present invention is not limited to the aforementioned secondary emitters. Compounds that can absorb or emit energy anywhere in the electromagnetic spectrum (from super high energy X-rays to very low energy microwaves, and to even lower energy radiofrequency sound waves) are compatible with the instant inventions.

Magnetic resonance imaging (NRI) agents are typically metal ions that are paramagnetic. In some embodiments, the agent may be useful for T1 weighted imaging and may be an ion of an element having the atomic number of 26 or lanthanide ions having the atomic number of 57-70. In some embodiments, it is preferable that the metal be Gd, Dy, Tb, Ho, Er or Fe ion. These metals can be associated with a chelating moiety. These chelators include ethylenediaminetetraacetic acid (EDTA) and diethylenetriaminepentaacetic acid (DTPA). These chelating groups are well known to those skilled in the art. For example, these chelators have been covalently bound molecules by a variety of methods, some involving attachment to functional groups such as amine, carboxyl, sulfhydryl, or phenyl groups. In other applications, the agents may be useful for T2-weighted imaging such as superparamagnetic iron oxide. All of the considered compounds can be either hydrophilic (present in the aqueous interior) or hydrophobic (present in the thick membranes) for incorporation into polymersomes.

Positron emitting moieties are also well-known in the art. These include $^{11}$C- and $^{18}$F-labeled moieties. Photodynamic therapy agents are also well-know in the art. These agents are photosensitive compositions such as porphyrins.

Other polymersomes additionally comprising one or more distinct emissive species. In some embodiments, the polymersome additionally comprises a radiological imaging agent. In some embodiments, the polymersome additionally comprises at least one of a secondary emitter, a cytotoxic agent, a magnetic resonance imaging (MRI) agent, positron emission tomography (PET) agent, photodynamic therapy (PDT) agent, ultrasound agent, radiological imaging agent, ferromagnetic agent, or ferrimagnetic agent, where the emitter or agent is compartmentalized within the aqueous polymersome interior.

Ultrasound agents include perflurocarbons or anything with heavy phase that causes echogenicity.

Ferro- or ferrimagnetic compounds include iron, magnetic iron oxide, such as magnetite, gamma-$Fe_2O_3$, $Fe_3O_4$, manganese ferrite, cobalt ferrite and nickel ferrite.

A number of radionucleosides are know to those skilled in the art. Often, an iodine-based compound which is physiologically acceptable, such as organically-bound iodine, is utilized. In addition, fluorocarbons have also been used as radiological imaging agents. See, for example, U.S. Pat. Nos. 3,975,512 and 4,987,154. Some other preferred metal radionuclides include $^{90}$Y, $^{99m}$Tc, $^{111}$In, $^{47}$Sc, $^{67}$Ga, $^{51}$Cr, $^{177m}$Sn, $^{67}$C, $^{179}$Tm, $^{97}$Ru, $^{188}$Re, $^{177}$Lu, $^{199}$Au, $^{203}$Pb and $^{141}$Ce.

In some embodiments, the invention concerns a method of delivering an agent to a biological situs in a tissue or organism comprising administering to the tissue or organism a polymersome having the agent and comprising (a) a plurality of amphiphilic block copolymers, each of the amphiphilic block copolymers comprising at least one hydrophilic polymer bonded to at least one hydrophobic polymer; (b) at least one phorphinato imaging agent; and (c) at least one targeting moiety associated with a surface of the polymersome. In certain embodiments, the agent is a therapeutic agent. Therapeutic agents are compositions that assist in the treatment of disease. The assistance can be by direct action of the agent or by indirect action where the agent assists another administered agent or a mechanism within the organism to act to treat the disease state. In some preferred embodiments, the agent is a pharmaceutical composition. In other embodiments, the agent is a chemotherapeutic agent. In still other embodiments the agent is a radiopharmaceutical. In yet further embodiments, the agent is biological entity such as a virus, organelle, bacterium, or cellular component.

Compositions and methods of the invention may be used to improve the bioavailability of the agent. In some cases, the agents that may be toxic, ineffective, poorly tolerated, poorly absorbed, or contraindicated when administered through conventional means. Compositions and methods of the invention may also be used to administer dosage amounts to a specific site that would be unsuitable for systemic therapy. For example, many agents administered systemically to treat one body or organ system, cause adverse effects in other body or organ systems. Such adverse effects may limit the dosage amount, length of time, effectivity, and so forth.

An energy source can be utilized to distort or disrupt the emissive polymersome, resulting in the release of at least a portion of the agent. In some embodiments, it is desirable that essentially the entirety of the agents be released. In certain embodiments, the therapeutic agent can be liberated using ultrasonic energy to disrupt the structure of the polymersome. In yet other embodiments, the therapeutic agent is liberated using light energy to disrupt the structure of the polymersome. Polymersomes can also be disrupted by heating. Preferably, the heating is a localized to the polymersome. In yet other embodiments, the polymersome can be disrupted through chemical reactions that involve for example, enzymatic degradation of polymeric components. Enzymes involved in such process may be located exterior the emissive polymersome, or packaged within its aqueous interior.

In some aspects, the invention relates to a method of ascertaining the presence or absence of a disease state in an organism or tissue comprising:

administering a polymersome to a patient, the polymersome comprising (a) a plurality of amphiphilic block copolymers, each of the amphiphilic block copolymers comprising at least one hydrophilic polymer bonded to at least one hydrophobic polymer; (b) at least one phorphinato imaging agent; and (c) at least one targeting moiety associated with a surface of the polymersome;

providing an instrument optically coupled to a light source, a light detector, or both, and operating the instrument to monitor the amount or distribution of the phorphinato imaging agent within the organism or tissue.

An light source may be used for illuminating an area of interest to determine the presence of an emissive probe in a location. The light source may illuminate an area of interest directly, as when in vitro cell cultures maintained in optically transparent containers are illuminated or when tissue is exposed, such as in connection with surgery, or it may be utilized to illuminate an area of interest indirectly through adjacent or overlying tissue such as bone, dura, skin, organ, muscle and the like. The light source employed in the present invention may be a high or low intensity source. The emitted light can be continuous wave (CW) light, time-resolved (TR) light, or both CW and TR light.

Suitable illumination sources include high intensity sources, broad spectrum and non-chromatic sources, tungsten-halogen lamps, lasers, light emitting diodes, and the like. Cutoff filters for selectively passing all wavelengths above or below a selected wavelength may be employed. For example, a cutoff filter that excludes all wavelengths below about 695 nm may be used.

In some embodiments, preferred wavelengths for acquiring data relating to intrinsic optical signals include, for example, wavelengths of from about 450 nm to about 2500 nm, and most preferably, wavelengths of the near infrared spectrum of from about 700 nm to about 2500 nm, and even more preferably, from about 600 nm to about 900 nm. Generally, longer wavelengths are employed to detect cellular or tissue condition of locations beneath the surface of cells or tissue, or beneath other materials such as skin, bone, dura, and the like cortical activity. The light source may be directed to the area of interest by any appropriate means. For some applications, the use of optical fibers is preferred. One preferred arrangement provides an light source through strands of fiber optic using a beam splitter controlled by a D.C. regulated power supply (such as one marketed by Lambda, Inc.).

The optical detection methods of the present invention may also usefully employ non-continuous illumination and detection techniques. For example, short pulse (time domain), pulsed time, and amplitude modulated (frequency domain) illumination sources may be used in conjunction with suitable detectors (see, for example, Yodh, A. and Chance, B., *Physics Today* (March 1995). Frequency domain illumination sources typically comprise an array of multiple source elements, such as laser diodes, with each element modulated at 180° out of phase with respect to adjacent elements (see, Chance, B. et al., *Proc. Natl. Acad. Sci. USA*, 90:3423-3427 (1993)). Two-dimensional arrays, comprising four or more elements in two orthogonal planes, can be employed to obtain two-dimensional localization information. Such techniques are described in U.S. Pat. Nos. 4,972,331 and 5,187,672.

In other aspects, the invention concerns a method of ascertaining the presence or absence of a disease state in an organism or tissue comprising:

administering a polymersome to a patient, the polymersome comprising (a) a plurality of amphiphilic block copolymers, each of the amphiphilic block copolymers comprising at least one hydrophilic polymer bonded to at least one hydrophobic polymer; (b) at least one phorphinato imaging agent; and (c) at least one targeting moiety associated with a surface of the polymersome;

providing an instrument optically coupled to a light source, a light detector, or both, and operating the instrument to monitor the amount or distribution of the phorphinato imaging agent within the organism or tissue.

The instant invention also concerns an in vivo method of diagnostics or imaging comprising:

contacting a polymersome with tissue within an organism, the polymersome comprising (a) a plurality of amphiphilic block copolymers, each of the amphiphilic block copolymers comprising at least one hydrophilic polymer bonded to at least one hydrophobic polymer; (b) at least one phorphinato imaging agent; and (c) at least one targeting moiety associated with a surface of the polymersome;

providing an instrument optically coupled to a light source, a light detector, or both, and using the instrument to monitor the amount of the polymersome at a situs within the tissue.

The present invention is exemplified by the following examples which are not intended to be limiting.

Example 1

OE7 Synthesis

OE7, polyethylene oxide-polyethylethylene ($EO_{40}$-$EE_{37}$, number average molecular weight, $M_n$, of about 3900 g/mol, volume fraction of EO=0.398, a polydispersity measure is given by Mw/Mn~1.10) is synthesized and characterized by the methods of Hajduk D A, Kossuth M B, Hillmyer M A, Bates F S, *J. Phys. Chem. B* 102, 4269 (1998), H. E. Warriner, S. H. J. Idziak, N. L. Slack, P. Davidson, C. R. Safinya, *Science* 271, 969 (1996), M. A. Hillmyer and F. S. Bates, *Macromolecules* 29, 6994 (1996); and M. A. Hillmyer et al, *Science* 271: 976 (1996).

Example 2

OB2 Synthesis

OB2, polyethylene oxide-polybutadiene ($EO_{26}$-$BD_{46}$, number average molecular weight, $M_n$, of about 3600 g/mol, volume fraction of EO=0.28) was synthesized by the methods of M. A. Hillmyer and F. S. Bates, *Macromolecules* 29, 6994 (1996).

Example 3

OB18 Synthesis

OB18, polyethylene oxide-polybutadiene ($EO_{80}$-$BD_{125}$, number average molecular weight, $M_n$, of about 10,400 g/mol, volume fraction of EO=0.29) was synthesized by the methods of M. A. Hillmyer and F. S. Bates, *Macromolecules* 29, 6994 (1996).

Example 4

OB21 Synthesis

OB8, polyethylene oxide-polyethylethylene ($EO_{40}$-$EE_{37}$, Mn of about 3900, and volume fraction of EO is 0.39) was synthesized and characterized by the methods of M. A. Hillmyer and F. S. Bates, *Macromolecules* 29, 6994 (1996).

Example 5

A. General Vesicle Preparation

Preparation of polymersomes can be accomplished by one of several techniques: electroformation (see Discher B M, Won Y-Y, Ege D S, Lee JC-M, Bates F S, Discher D E, Hammer D A, *Science*, 284, 1143 (1999)), film rehydration, or bulk rehydration.

B. NIRF Incorporation in Polymersome Membranes by Thin-Film Rehydration

Polymersomes that possess dispersed porphyrin-based NIRFS within their polymer membranes can be prepared by thin-film rehydration. 100 µL of 1 mM $PEO_{30}$-$PBD_{46}$ diblock copolymer (P2903-BdEO, Polymer Source Inc, Dorval, Quebec Canada) and 5 µL of 1 mM solutions of NIRF species ($PZn_2$-$PZn_5$) in methylene chloride are uniformly coated on the inside wall of a glass vial or on the surface of roughened Teflon, followed by evaporation of the solvent under vacuum for >12 h. Addition of sucrose solution (250-300 mOsM) and heating at 60° C. for 24 h leads to spontaneous budding of giant (5-20 µm) NIR-emissive polymerosmes off of the glass (or Teflon) into solution.

Example 6

NIRF Incorporation in Polymersome Membranes by Bulk Rehydration

For bulk rehydration, a few milligrams of solid polymer and porphyrin can be placed in 1 ml of sucrose solution with overnight stirring.

Example 7

Reduction of Vesicle Size

Small vesicles that posses appropriately narrow size distributions (within the 100-200 nm diameter range) can be prepared via procedures analogous to those used to formulate small unilamellar liposomes (sonication, freeze-thaw extraction, and extrusion).

Example 8

Reduction of Vesicle Size by Sonication and Freeze Thaw (FTS Method)

The sonication procedure involves placing a sample vial containing the aqueous-based solution and a dried thin-film formulation (of polymer and NIRF species uniformly deposited on Teflon®) into a bath sonicator (Fischer Scientific, Fair Lawn, N.J.; Model FS20) with constant agitation for 30 minutes. Several (×3-5) cycles of freeze-thaw extraction follow by placing the sample vials (containing solutions of medium-sized, 300 nm, NIR-emissive polymersomes) in liquid $N_2$. Once the bubbling from the liquid $N_2$ subsides, the vials are subsequently transferred to a 56° C. water bath.

Example 9

Reduction of Vesicle Size by Extrusion

Extrusion to a mono-dispersed suspension of small (100 nm diameter) vesicles proceeds by the introduction of the aqueous solution into a thermally controlled, stainless steel, cylinder connected to pressurized nitrogen gas. The vesicle solution is pushed through a 0.1 μm polycarbonate filter (Osmonics, Livermore, Calif.) supported by a circular steel sieve at the bottom of the cylinder, where the vesicle solution is collected after extrusion. This procedure can be repeated multiple times, and the size distribution of vesicles is measured by dynamic light scattering (DynaPro, Protein Solutions, Charlottesville, Va.).

Example 10

Confocal Microscopy of NIR-Emissive Polymersomes

Giant (5-20 μm) NIR-emissive polymersomes are fabricated by the methods described above (vesicle's external and internal aq solutions are identical ~290 mOsM sucrose). The vesicle solution is diluted 30:70 in osmotically matched PBS. 200 μL of the resultant solution is placed in a custom fitted sample chamber. The chamber is constructed with a 75×25×1 mm plain microscope slide (Corning Glass Works Scientific Glassware Dept, Corning, N.Y.; Model 2947), two parallel 5×25×2 mm Teflon spacers and a 18×18 mm microscope cover slip (Fisherbrand, Fisher Scientific, Pittsburgh, Pa.) adherent by high vacuum grease. The chamber containing the vesicle solution is then placed on the stage of an inverted confocal microscope and 20 minutes is allotted for the NIR-emissive polymersomes to settle on the coverslip before imaging.

Fluorescence scanning confocal microscope images of 5-20 μm NIR-emissive polymersomes were obtained using a Radiance 2000 Multi-photon Confocal System (Bio-Rad Laboratories, Hercules, Calif.) equipped with a 650 nm long-pass emission filter (excitation via argon laser, $\lambda_{ex}$=488 nm).

Figure 9:
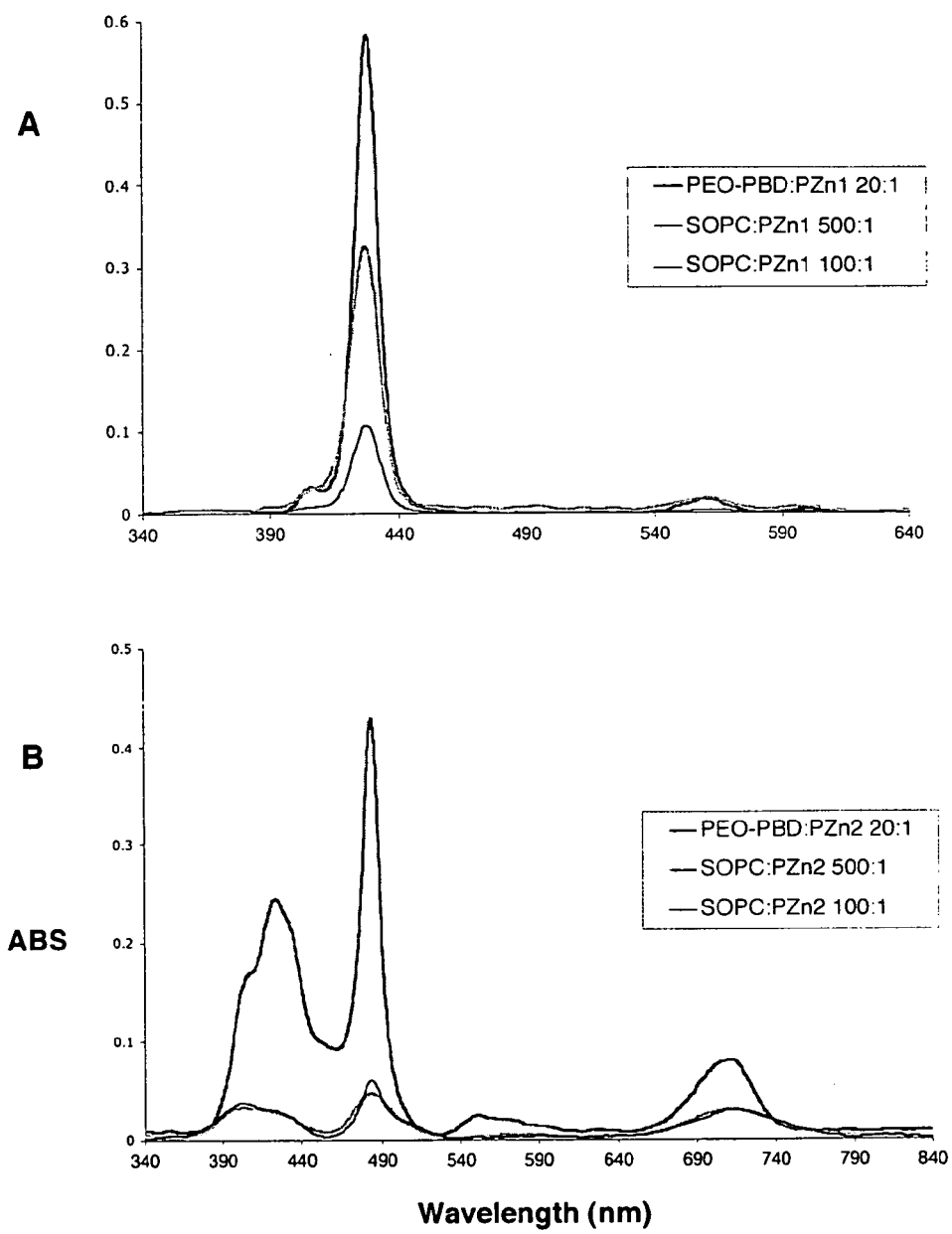
FIG. 9 illustrates a comparative study of membrane loading of hydrophobic NIRFs in polymersomes vs. liposomes. For a constant amount of NIRF species, polymersomes are able to incorporate the smaller NIRFs $PZn_1$ and $PZn_2$ in their bilayered membranes at a significantly higher mole fraction than SOPC liposomes. Additionally, they are uniquely able to incorporate the larger conjugated NIRFs $PZn_3$-$PZn_5$. (A) SOPC vs. polymer membrane loading of a benchmark porphyrin monomer $PZn_1$. (B) SOPC vs. polymer membrane loading of NIRF $PZn_2$.

FIG. 9 demonstrats fluorescence emission from NIRF $PZn_3$-based NIR-emissive polymersomes that were modified for contrast and brightness using Adobe Photoshop software.

Example 11

Photophysical Studies of Porphyrin-Based Near Infrared Flurophores (NIRFS) in Polymersome Membranes Medium-sized (300 nm) NIRF-incorporated emissive vesicles were generated by thin-film rehydration and sonication; electronic absorption and fluorescence spectrophotometric studies of the aqueous vesicle solutions were conducted to obtain data on incorporation efficiencies and fluorescence properties. Calculation of absorption extinction coefficients ($\epsilon$, $M^{-1}cm^{-1}$) for $PZn_2$-$PZn_5$ dispersed in polymersome membranes followed a Beer's law determination.

First, the emissive vesicle solutions were placed in 10 mm quartz optical cells and electronic spectra for each of the membrane-incorporated NIRF species were recorded on an OLIS UV/Vis/NIR spectrophotometery system that is based on the optics of a Cary 14 spectrophotometer (On-line Instrument Systems Inc, Bogart, Ga.). 2 mL of each vesicle solution was then transferred to a glass vial and frozen in liquid $N_2$. Next, the frozen solutions were lyophilized (FreeZone 4.5 L Benchtop Freeze Dry System, Labconco Corporation, Kansas City, Mo.; Model 77500) for 24 hours to destroy the vesicles and dry the polymer and NIRF species.

The dry samples were then taken up in THF and their absorption spectra were recorded. Concentrations of polymer and NIRF species in the original aqueous NIR-emissive polymersome solutions were calculated by comparison of the NIRF absorption spectra in THF to previously determined absorption $\epsilon$ in this organic solvent. These data were used to determine absorption $\epsilon$ for the NIRF species incorporated in polymersome membranes. This procedure was repeated ten times for each $PZn_2$-$PZn_5$ based polymersome formulation; absorption E values reported represent the average for these extinction coefficient determinations. Individual values varied typically by less than 10% of the reported numbers.

Example 12

Fluorescence Spectroscopy of Porphyrin-Based NIRFs in Polymersome Membranes

Fluorescence spectra of NIR-emissive polymersomes were obtained with a Spex Fluorolog-3 spectrophotometer (Jobin Yvon Inc, Edison, N.J.) that utilized a dual S- and T-channel configuration and PMT/InGaAs/Extended-InGaAs detectors; an excitation wavelength of 510 nm was used for each sample. Emission spectra were corrected using the spectral output of a calibrated light source supplied by the National Bureau of Standards. The fluorescence spectra were displayed to highlight relative peak emission wavelengths and spectral breadth. Examining the emission from aged (3-5 days) solutions showed that these structures are extremely stable and evince no evidence of NIRF leakage or destruction as evidenced by constant and stable fluorescence.

Example 13

Determination of the Optimal Extent of Membrane Loading of Porphyrin-Based NIRFs in Polymersomes Thin-film formulations deposited on Teflon at various ratios of polymer:porphyrin-based NIRF species ($PZn_1$-$PZn_3$ and $PZn_5$) were created from various amounts of stock solutions (1 mM in $CH_2Cl_2$) of an OB-2-like polymer modified with a terminal 4-hydroxy-benzoate (to give the polymer a UV signal; obtained from Polymer Source Inc, Dorval, Quebec Canada) and individual solutions of the conjugated porphyrin-based NIRF species (1 mM in $CH_2Cl_2$). Thin-films were created and deposited on Teflon® by combining the block copolymer and the porphyrin-based NIRF species in the following ratios:

1. 1:1 polymer to NIRF (20 μL polymer solution and 20 μL porphyrin solution)

2. 5:1 polymer to NIRF (100 μL polymer solution and 20 μL porphyrin solution)

3. 10:1 polymer to NIRF (200 μL polymer solution and 20 μL porphyrin solution)

4. 15:1 polymer to NIRF (300 μL polymer solution and 20 μL porphyrin solution)

5. 20:1 polymer to NIRF (400 μL polymer solution and 20 μL porphyrin solution)

6. 25:1 polymer to NIRF (500 μL polymer solution and 20 μL porphyrin solution)

7. 30:1 polymer to NIRF (600 μL polymer solution and 20 μL porphyrin solution)

8. 40:1 polymer to NIRF (800 μL polymer solution and 20 μL porphyrin solution)

9. 50:1 polymer to NIRF (1000 μL polymer solution and 20 μL porphyrin solution)

Vesicles were generated from each of these formulations by rehydration of the thin-films in 4 mL water (resulting in approximately 5 μM concentrations of NIRF in aqueous polymersome solutions). Absorption and fluorescence spectrophotometric studies of the membrane-incorporated NIRFs were conducted to obtained data on the yield of polymersomes from polymer starting material, incorporation efficiencies of NIRFs in polymersome membranes, and relative fluorescence intensities of polymersomes loaded with different sized porphyrin-based NIRFs, all as a function of the ratio of polymer:NIRF species deposited as a thin film on Teflon®. Experiments were conducted with n=5 samples for each unique formulation.

Absorption spectra were obtained for each aqueous sample of polymersomes formed by rehydration of the various thin-formulations of polymer:NIRF. Monitoring the UV absorbance of the modified polymer ($\lambda$=255 nm) and visible/NIR absorbances of the porphyrin allowed for the determination of the solution concentrations of these species from a Beers law calculation (A=εcd where A is absorbance, c is the concentration, ε is the absorption extinction coefficients, and d is the light path distance) where ε for both the polymer (24,400 at $\lambda$=255 nm) and fluorophore (see V. S.-Y. Lin, S. G. DiMagno, M. J. Therien, *Science* 264, 1105-1111 (MAY 20, 1994); V. S.-Y. Lin, M. J. Therien, *Chemistry-a European Journal* 1, 645-651 (DEC, 1995); K. Susumu, M. J. Therien, *Journal of the American Chemical Society* 124, 8550-8552 (Jul. 24, 2002); and I. V. Rubtsov, K. Susumu, G. I. Rubtsov, M. J. Therien, *Journal of the American Chemical Society* 125, 2687-2696 (MAR 5, 2003)) were already known. This data gave information on the yield of polymersomes in solution as a function of the ratio of polymer:NIRF deposited on Teflon® by comparing this calculated amount of polymer in solution to the known amount of starting polymer material deposited on the films. Additionally, the incorporation of the NIRF species in polymersome membranes as a function of the ratio of polymer:NIRF deposited on Teflon® was similarly calculated from known amounts of starting NIRF material. Finally, having determined the concentrations of both polymer and NIRF species in solution as a function of the ratio of polymer:NIRF deposited on Teflon® readily gives the extent of polymersome membrane loading as a molar ratio of polymer:NIRF.

Fluorescence spectra were obtained for aqueous sample of polymersomes formed by rehydration of the various thin-film formulations of polymer:NIRF. For each of the unique NIRF species, comparing the fluorescence intensity of its membrane-incorporated polymersome solutions to the extent of NIRF membrane-loading calculated above, gives the optimal ratio of polymer:dye that should be used for thin-film rehydation to yield maximally emissive polymersomes. This value is expressed as a normalized relative fluorescence by measuring the number of counts from aqueous samples of NIRF incorporated polymersomes and dividing this value by that of the most fluorescent formulation of polymer:flurophore for a given NIRF species.

Example 14

Comparative Membrane Loading of NIRFs in Polymersomes vs. Liposomes

A benchmark porphyrin monomer $PZn_1$ can be loaded in the SOPC liposomes at approximately 0.5-1% molar concentrations, by thin-film rehydration plus sonication, as long as the deposited film on Teflon contains in excess of 100:1 molar ratio of lipid:NIRF (FIG. 12A). Absorption spectra of aqueous liposome solutions formed similarly from thin films of SOPC and $PZn_2$ demonstrated limited incorporation of this larger NIRF in liposome membranes (FIG. 12B). Although these results indicate uptake of $PZn_2$ from Teflon films when the molar ratio of lipid:NIRF exceeds 100:1, the absorption spectra did not increase for solutions of liposomes fabricated from thin-film formulations where the lipid:NIRF molar ratio is higher (500:1). Notably, in contrast to analogous experiments involving $PZn_2$ incorporation in polymersomes, electronic absorption spectra of aqueous solutions of SOPC liposomes (formed from thin-film formulations of lipid and $PZn_2$) do no resemble the spectra of this NRF in organic solvents; they are more likely consistent with aggregate formation rather than uniform membrane dispersion of this NIRF.

Figure 12:
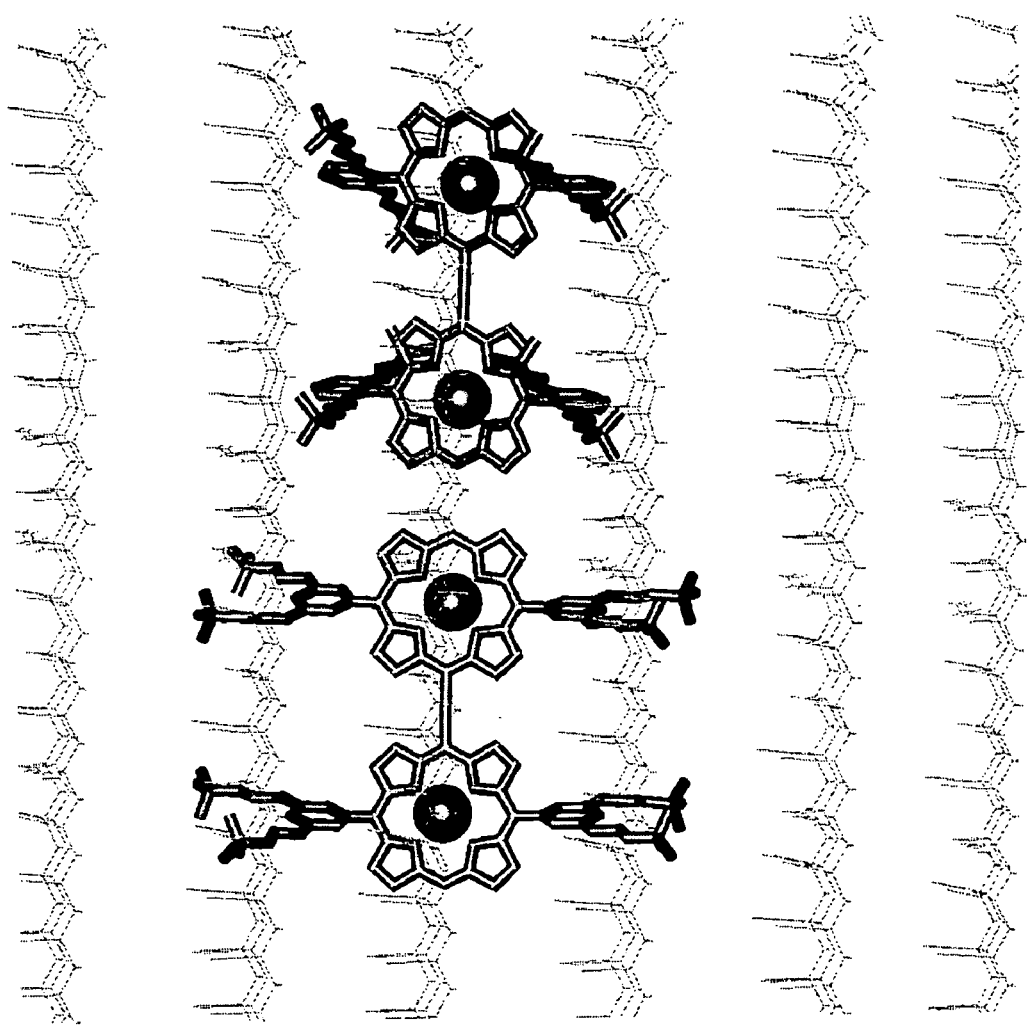
FIG. 12 illustrates an emissive porphyrin moiety with ancillary substituents that can be used in modulating emission.

Analogous experiments involving $PZn_3$-$PZn_5$ indicated no uptake of the larger NIRFs into SOPC liposomes (prepared by rehydration of thin-film formulations deposited at even 500:1 molar ratios of lipid:NIRF). In contrast, each NIRF species ($PZn_1$-$PZn_5$) was effectively and nearly equally incorporated in NIR-emissive polymersomes from thin-films of polymer and NIRF deposited at a 20:1 molar ratio (approximately 5% membrane loading) (FIG. 12). For all liposome and polymersome formulations, dynamic light scattering and phase contrast microscopy demonstrated the presence of vesicles.

Figure 5:
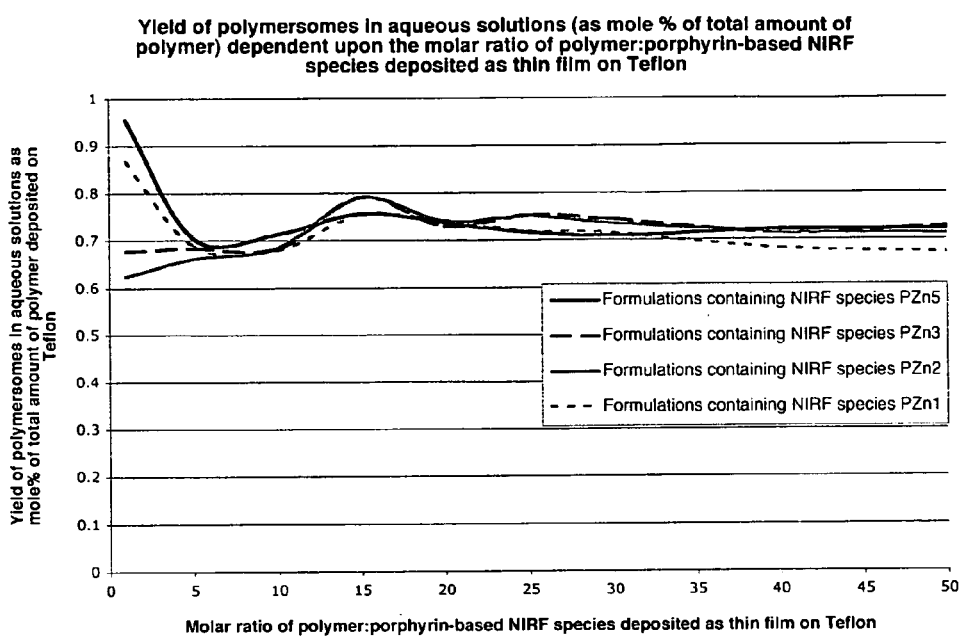
FIG. 5 illustrates the yield of polymersomes in aqueous solutions (as mole % of total amount of polymer used) dependent upon the molar ratio of polymer:porphyrin-based NIRF species deposited as thin film on Teflon®.

In FIG. 5, the loading of polymersomes with porphyrin-based fluorophores (depicted as molar ratios of polymer:dye in aqueous polymersome solutions) as a function of the molar ratio of polymer:flurophore originally deposited as a thin-film on Teflon is presented.

Figure 6:
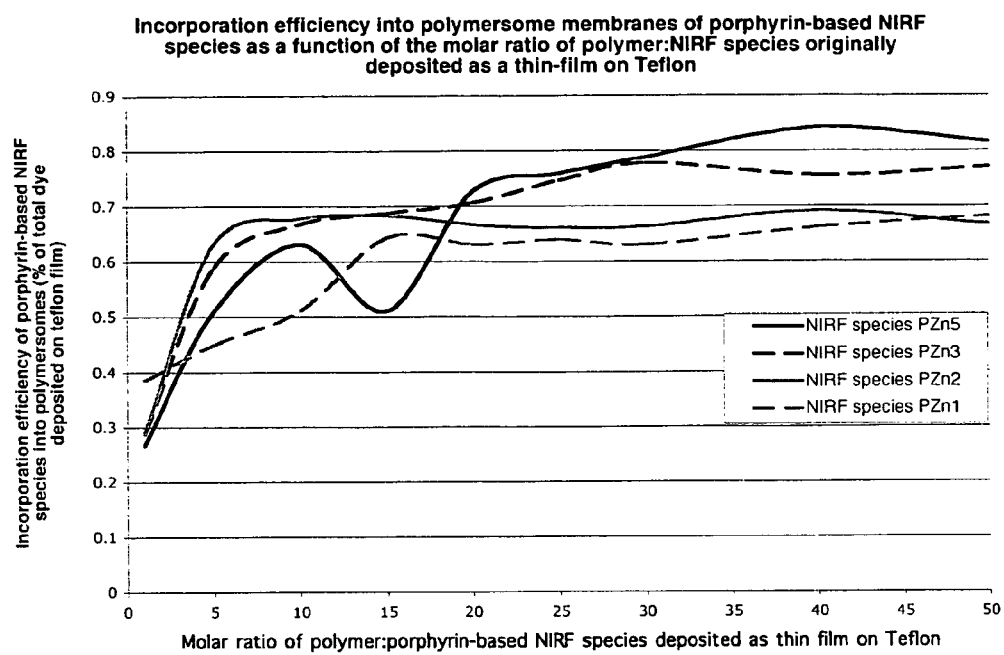
FIG. 6 illustrates the incorporation efficiency into polymersome membranes of porphyrin-based NIRFs as the molar ratio of polymer:porphyrin-based NIRF species deposited as a thin-film formulation on Teflon

In FIG. 6, the incorporation efficiency into polymersome membranes of porphyrin-based NIRFs as a function of the molar ratio of polymer:NIRF species deposited as a thin-film on Teflon is presented.

Figure 7:
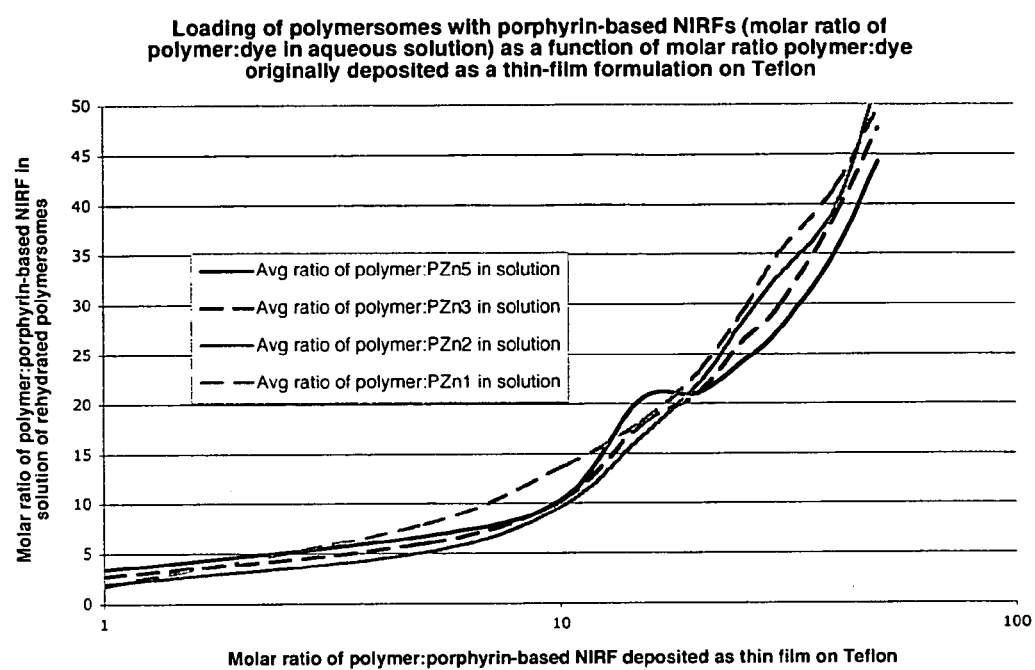
FIG. 7 illustrates loading of polymersomes with porphyrin-based NIRFS (molar ratio of polymer:dye in aqueous polymersome solutions) as a function of the molar ratio polymer:dye originally deposited as a thin-film formulation on Teflon.

In FIG. 7, the yield of polymersomes in aqueous solutions (as mole % of total amount of polymer used) as a function of the molar ratio of polymer:porphyrin-based NIRF species deposited as thin film on Teflon is presented.

Figure 8:
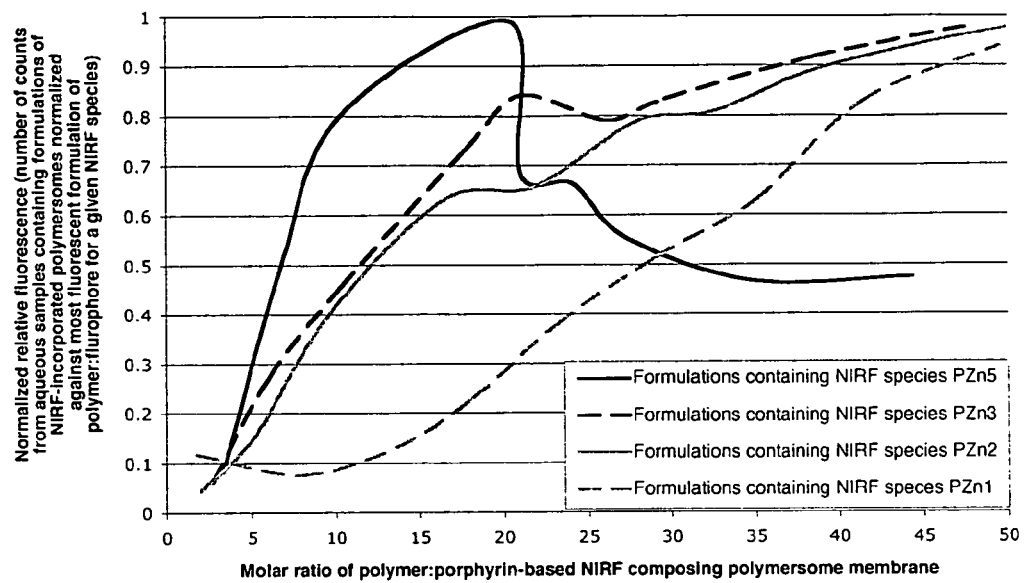
FIG. 8 shows the relative fluorescence of NIRF-incorporated polymersomes as a function of membrane loading (molar ratio of polymer:porphyrin-based NIRF species composing the polymersome membrane)

In FIG. 8, the relative fluorescence of NIRF-incorporated polymersomes as a function of membrane loading (molar ratio of polymer:porphyrin-based NIRF species composing the polymersome membrane) is presented.

In FIG. 9, results from a comparative study of membrane loading of NIRFs in polymersomes vs. liposome membranes is presented.

Example 15

Synthesis of Tresylated Block Copolymers

The protocol used to tresylate the ethylene oxide block was adopted from Nilsson, K. & Mosbach, K. *Methods in Enzymology* 104, 56-69 (1984); Delgado, C.; Patel, J. N.; Francis, G. E.& Fisher, D. *Biotechnology and Applied Biochemistry* 12, 119-128 (1990); and Delgado, C.; Francis, G. E.& Fisher, D. *Critical Reviews in Therapeutic Drug Carrier System* 9, 249-304 (1992). OE-21 was dissolved in dichloromethane at 0° C. A mixture of pyridine and tresyl chloride was added drop-wise and allowed to react at room temperature for 90 minutes. The organic solvent was evaporated and the product was precipitated using anhydrous methanol and hydrochloric acid until no pyridine was detected under UV spectrophotometry. NMR (chloroform-d as solvent) was used to verify the tresylation of block copolymers. The NMR spectra of OE-21 is documented in M. A. Hillmyer and F. S. Bates, *Macromolecules* 29, 6994 (1996). The NMR spectra of pure OE-21 has peaks at 0.8 ppm (singlet), 1.1 ppm (singlet), 1.3 ppm (doublet), and 3.65-3.80 ppm (multiple peaks); Pure tresyl chloride has peaks at 4.4 ppm (triplet). The NMR spectra of tresylated OE-21 polymer had peaks at the locations of pure OE-21 and pure tresyl chloride.

Example 16

Functionalization and Formation of Polymersomes

Biotinylated polymersomes for adhesion experiments were formed by reacting 50 μg the tresylated polymer with a 2:1 excess of biocytin in anhydrous methanol overnight at 4° C. A thin film of polymer was deposited on the bottom of a vial by evaporation and polymersomes were formed by rehydration with 1 mL (300 mOsm) sucrose solution (Osmometer Model 3300, Advance Instruments, Norwood, Mass.). Excess biocytin molecules in the external solution were removed by dialysis, using 10K MW cutoff Slide-a-Lyzer dialysis cassettes purchased from Pierce (Rockford, Ill.). Vesicle solution was injected into the dialysis cassette with a syringe and the cassette was immersed in a beaker filled with iso-osmotic PBS solution with soluble neutravidin to reduce the concentration of free biocytin to less than one thousandth of the dissociation equilibrium constant (KD=10-14M) of biotin and avidin. Vesicles were subsequently removed from dialysis and used immediately for adhesion or bulk avidin adsorption measurements.

Biotinylated vesicles to measure the adsorption of avidin from solution were incubated with an excess of avidin-rhodamine isothiocynanate in PBS overnight. Excess avidin was removed by dialysis in 100K MW cutoff membranes against clean PBS. The resulting samples were imaged with confocal microscopy.

Alexa-Biotin polymersomes for confocal experiments were formed by reacting tresylated polymer with a 2:1 excess of Alexa-biocytin in anhydrous methanol overnight at 4° C. The polymer was dried and redissolved in chloroform, followed by three successive washes with PBS to remove excess Alexabiocytin. The Alexa-biotin polymer was mixed in varying ratios with unmodified polymer in chloroform and dried to a uniform film. The film was rehydrated with 300 mOsm sucrose to form vesicles. This solution was subsequently diluted with iso-osmotic PBS to provide contrast for imaging.

Example 17

Synthesis of Porphyrinic Imaging Agents

Porphyrinic imaging agents are synthesized generally by methods taught in U.S. Pat. Nos. 5,371,199; 5,493,018; 5,599,924; 5,756,723; 5,783,306; 5,817,830; 5,856,515; 5,955,603; 5,986,090; and 6,100,392.

Example 18

Confocal and In Situ Fluorescence Imaging of NIR-Emissive Polymersomes

Scanning confocal microscope images of 5-20 μm polymer vesicles featuring membrane-dispersed NIRF PZn$_3$ are presented in FIG. 10A. Fluorescence ($\lambda_{em}^{max}$=809 nm) images were obtained with a BioRAD Radiance 2000-MP Confocal Microscope System, equipped with a 650 nm long-pass emission filter, and demonstrate that fluorescence arises exclusively from the vesicle membranes. Note that the vesicular internal aqueous core and external solution were identical (290 mOsM sucrose). FIG. 10B shows in situ fluorescence image of a 10 mL sample tube containing 5 mL a PZn$_3$-based aqueous NIR-emissive polymersome solution. Solutions were prepared by thin-film rehydration of PEO-PBD copolymer and PZn$_3$ followed by standard processing (sonication/freeze-thaw extraction/extrustion) to yield mono-dispersed, 100 nm diameter vesicles as determined by dynamic light scattering. Fluorescent images of the solutions were obtained with a Xenogen Ivis Imaging System equipped with a CCD camera and appropriate filters for specific NIR excitation and fluorescence detection.

Example 19

Micropipette Aspiration

Micropipette aspiration is described in detail in Evans, E.; Needham, D. *J. Phys. Chem.* 91, 4219-4228 (1987); Bo, L.; Waugh, R. E. *Biophys. J.* 55, 509-517 (1989); Bozic, B.; Svetina, S.; Zeks, B.; Waugh, R. E. *Biophys. J.* 61, 963-973 (1992); Waugh, R. E.; Song, J.; Svetina, S.; Zeks, B. *Biophys. J.* 61, 974-982 (1992); Heinrich, V.; Waugh, R. E. *Annals of Biomed. Eng.* 24, 595-605 (1996); Evans, E. A. *Biophys. J.* 48, 175-183 (1985); Evans, E. A. *Biophys. J.* 48, 184-192 (1985); Evans, E.; Berk, D.; Leung, A. *Biophys. J.* 59, 838-848 (1991); Evans, E.; Berk, D.; Leung, A.; Mohandas, N. *Biophys. J.* 59, 849-860 (1991); Berk, D.; Evans, E. *Biophys. J.* 59, 861-872 (1991); Evans, E.; Leung, A. *J. Cell Biology*

1984 98, 1201-1208 (1984); Noppl-Simson D. A.; Needham, D. *Biophys. J.* 70, 1391-1401 (1996); Kim, D. H Klibanov, A. L.; Needham, D. *Langmuir* 16, 2808-2817 (2000); Evans, E.; Klingenberg D. J.; Rawicz, W.; Szoka, F. *Langmuir* 12, 3031-3037 (1996); Bermudez H; Brannan A. K.; Hammer D. A.; Bates F. S.; Discher D. E. *Macromolecules* 35 8203-8208 (2002); and Lee J. C.-M.; Santore M.; Bates F. S.; Discher D. E. *Macromolecules* 35 323-326 (2002). Concisely, micropipettes, borosilicate glass tubing (Friedrich and Dimmock, Milville, N.J.), were made using a needle/pipette puller (model 730, David Kopf Instruments, Tujunga, Calif.) and micro-forged using a glass bead to give the tip a smooth and flat edge. The inner diameters of the micropipettes used ranged from 1 μm up to 6 μm. The inner diameter of micropipettes was measured using computer imaging software. Micropipettes were used to pick up both polymersomes and microspheres (Superavidin coated microspheres, Bangs Laboratories, Inc., Fishers, Ind.) and apply tension to polymersome membranes. Micropipettes were filled with PBS solution and connected to two aspiration stations. Each aspiration station was mounted on a side of a Nikon Diaphot inverted microscope and each station was equipped with a monometer, two Validyne pressure transducers (Model DP 15-32 and DP 103-14, Validyne Engineering Corp., Northridge, Calif.), two digital pressure read-outs, a micromanipulators (Model WR-6, Narishige, Tokyo, Japan), and MellesGriot millimanipulators (course x,y,z, control). Suction pressure was applied by syringes connected to the monometers. Experiments were performed in PBS solutions that had osmolalities of 350 mOsm in order to make the polymersomes flaccid. The osmolalities of the solutions were measured using an Osmometer. Because the sucrose and PBS solutions have different densities and refractive indices, the polymersomes sediment are visible with phase-contrast or Hoffman optics.

Example 20

Adhesion Experiment

Adhesion experiments were performed inside a chamber (FIG. 3) made from microscope cover glasses, 18 mm (width)×18 mm (length), from Fisher Scientific (Pittsburgh, Pa.) and Micro Slides from Corning Glass Work (Corning, N.Y.). A reusable chamber frame was made by using a metal paper clip to connect two Micro Slides (25×32 mm) together. A clean chamber was prepared for each experiment by cutting cover glasses into narrow strips (5×18 mm) and fixing them in place with small amount of vacuum grease. The cover glasses form the ceiling and the floor of the chamber. The volume of the chamber is approximately 40 μl. The side of the chamber was open so that micropipettes could assay the interior compartment of the chamber. The tip of each micropipette was immersed in 0.5 wt % BSA solution (0.005 g of BSA in 1 ml of distilled water) for about 30 seconds to prevent non-specific adhesion of the aspirated object to the tip of micropipette. The surfaces of the chamber were coated with 0.5% BSA solution before introducing the microsphere/polymersome solution, preventing vesicles from non-specifically adhering to the glass walls. A polymersome and a microsphere were picked up using two micropipettes that were mounted coaxially and facing each other. After the polymersome and microsphere pair was brought into contact, the tension on the polymersome was decreased gradually to allow the contact zone to form. The surfaces were left undisturbed for 15 minutes to allow the polymersome surface ligands, biocytin, to bind to the complementary surface groups on the microspheres, superavidin. After 15 minutes, the tension on the polymersome was increased gradually, and the events recorded using optical video microscopy. The tension at which the polymersome and microsphere no longer adhered was labeled as the critical tension. Experiments were recorded using a video CCD camera (Model 4915, Cohu Inc., San Diego, Calif.) and a SONY SVO-9500MD VTR (Sony Medical System, Montvale, N.J.). Images for analysis were retrieved afterwards from the recorded tapes using the IMAQ software from National Instruments for subsequent analysis. Image analyses were done via computer software, Scion Image, from Scion Corporation (Frederick, Md.).

Example 21

Formation of Functional Vesicles and Controlling the Surface Concentration of Biocytin The incorporation of the functionalized polymer into the final vesicular structures was verified in a series of experiments using polymer functionalized with fluorescent biotin. In order to systematically vary the surface concentration of biotin, the functionalized polymer is mixed with unfunctionalized polymer in chloroform before drying to form a uniform polymer film. Alexa Fluor 488 biocytin functionalized OB-18 (OB-18b) polymer is mixed with either OB-2 or OB-18 at concentrations of 0%, 10%, 20%, 50%, 80% and 100% OB-18b (by mass). The resulting polymersomes were imaged using confocal microscopy to assess the relative incorporation of functionalized polymer into the polymersomes. Each series was analyzed sequentially with the same instrumental settings to minimize the effect of laser intensity or detector sensitivity fluctuations. The amount of fluorescence was quantified by measuring the peak intensity of each polymersome above any fluorescence detected in its aqueous core. The edge brightness increased proportionally to the amount of modified OB18 polymer added, indicating the surface concentration of biotin may be effectively varied by changing the concentration of polymer in the film used to make the vesicles. The ability of the block copolymers to self-assemble into polymersomes did not appear to be affected by modification with either biocytin, tresyl chloride or rhodamine.

Example 22

Adsorption of Avidin onto Functionalized Polymersomes from Bulk Solution

To verify the availability of biotin on the polymersome surface to bind to avidin, biotin-labeled polymersomes were incubated with soluble Alexa Fluor 488 conjugated streptavidin and then imaged with confocal microscopy. A negative control sample using untresylated polymer indicates that there is no non-specific adhesion of Alexa Fluor 488 conjugated streptavidin to an unmodified polymersome surface. The amount of fluorescence at the surface of OB-18 and OB-2 polymersomes was quantified as the amount of biotinylated OB-18 is increased. The two series were normalized with respect to one another by the intensity of 100% OB-18b samples. There was little change in the average amount of fluorescent intensity for either series above 10 mole %. There is no discernible difference in the amount of fluorescence obtained by adsorption of avidin from the bulk solution onto vesicles made with OB-18b in either OB-18 or OB-2 polymersomes.

Example 23

Classification of Adhesion

To measure the adhesion between biotinylated polymersomes and superavidin coated microspheres, it is necessary to identify the regime of adhesiveness. Biotin-labeled polymersomes bind to superavidin-coated microspheres as a kinetically trapped system because the contact area forms spontaneously, and the tension required to peel a contact increases as the contact area decreases. The contact distance was measured as the linear distance between the two edge points of where the polymersome was in contact with the microsphere. Prior to the peeling experiment, the biocytin-coated polymersome was brought into contact with the superavidin-coated microsphere. The tension on the polymersome is decreased gradually to allow the polymersome to adhere to the microsphere; the micropipette was retracted from contacting the polymersome and the polymersome is allowed to bind to steady state for 15 minutes. While one micropipette holds the superavidin-coated microsphere statically, the other micropipette is moved to just touch the polymersome. As the suction pressure increases, the polymersome is aspirated into the micropipette with increasing projected length. As the polymersome is initially aspirated, a small portion of the adhering membrane is peeled from contact with the microsphere with a small tension. After this initial decrease in the contact distance, the contact distance decreases slowly as the tension applied on the vesicle membrane increases, until the critical tension is reached. At the critical tension, all the biotin-avidin bonds connecting the polymersome and the microsphere are broken, and the contact distance decreases to a single contact point and breaks. This system behaves fundamentally different from an equilibrium system, where the force needed to form the contact is essentially equal to the force required to separate the contact. Thus, the appropriate metric of adhesion is the critical tension, rather than the adhesion energy. In the current experiment, even though the polymersome initially adheres to the superavidin-coated microsphere through spreading, it is the bonds between biocytin and avidin formed within the contact area that are responsible for holding the polymersome to the microsphere. A similar experiment with an unmodified polymersome results in a contact area between the polymersome and microsphere that decreases rapidly with a negligible applied tension. A similar result is observed if the adhesion experiment is repeated with an excess of soluble biotin, which demonstrates the adhesion is specifically due to avidin-biotin binding.

Example 24

Measurement of Critical Tensions

Various compositions of biotinylated polymersomes were made by mixing OB-18b with OB-2 or OB-18 in different percentages. Since OB-2 is much shorter than OB-18, it was hypothesized that the two different membranes would result in different molecular surface topographies that would affect the subsequent adhesion between the polymersome and microsphere. With functionalized OB-18 (OB-18b) in pure OB-18: there is no advantageous presentation of biotin away from the base membrane. With functionalized OB-18 in OB-2: the difference in the chain length of OB-2 and OB-18 polymers favors a surface topography in which the adhesion molecules on OB-18 are extended beyond the shorter OB-2 surface brushes. The critical tensions needed to separate the polymersomes and microspheres were plotted against the molar percentage of biotinylated OB-18 polymer in the polymer mixture. The critical tensions of polymersomes made from an OB-18 membrane increase with biotinylated polymer concentration up to 10 mole % of OB-18b. The critical tension does not increase as OB-18b is increased beyond 10 mole %, suggesting that the avidin binding is saturated. When biotinylated OB-18 is mixed with OB-2 (closed symbols), the critical tension increases as the percentage of biotinylated OB-18 increases until a maximum is reached near 55 mole % OB-18b. Further increases in biotinylated OB-18 result in lower critical tensions, until the membrane is purely OB-18b. A plateau of adhesion is not observed in this system, and the critical tensions measured when OB-18b is mixed with OB-2 are larger than those when OB-18b is mixed with OB-18. Several negative control experiments were performed to ensure the measured critical tensions are unique and reproducible. The critical tension of polymersomes modified with Alexa Fluor 488 biocytin were indistinguishable from the results reported above. No adhesion was observed between polymersomes made from tresylated polymers and avidin coated microspheres. To exclude the possibility that unreacted tresyl groups participate in or complement the adhesion of the biotinylated vesicles, biotinylated polymersomes were reacted with ethanolamine to cap any remaining tresyl groups.

The critical tensions measured from ethanolamine capped vesicles are within a standard deviation of samples at the same concentration without ethanolamine capping. It is believed that the surface topology, membrane composition, or presentation of biotin plays an important role in the adhesion of polymersomes to a surface.

Example 25

Tether Formation of Functionalized Polymersomes

Tether formation from the membrane of functionalized polymer vesicles was observed when attempting to measure the critical tension of vesicles with low concentration of OB-18b in OB-2; however, no tether formation were observed from the vesicles with the same concentration of OB-18b in pure OB-18 or from vesicles with higher concentrations of OB-18b polymers regardless of the polymer used as the base membrane. Stable tether formation is highly reproducible at 4 mole % of OB-18b in OB-2. Suction pressure was originally being applied on the polymersome membrane through a micropipette; the suction pressure was subsequently decreased and the polymersome was released from the micropipette. The polymersome was drawn back to the avidin coated microsphere by the tether formed between the biotinylated polymersome and the superavidin-coated microsphere. The tether diameter increases as the polymersome is drawn closer to the superavidin-coated microsphere due to conservation of total volume.

Example 26

Functionalized Polymersomes Containing NIRFs

Polymersomes are formed generally as described in Example 5 except that at least a portion of the block copolymer is functionalized as in Example 16.

Example 27

Detection of NIR-Emissive Polymersomes within a Tumor

Fluorescence images of NIR-emissive polymersomes, generating a signal from deep within the tumor of the live animal, were obtained using an Ivis Imaging System (Xenogen Corporation, Alameda, Calif.; 100 series) equipped with white-light excitation, CCD camera-based fluorescence detection (Ivis 77 SI620EEV), and a filter set appropriate for NIR-emitting indocyanine green (band-pass excitation 705-765 nm and emission 805-880 nm). Images were taken at 30, 35, 45, 60, 120 minutes following direct tumor injection of the NIR-emissive polymersome solution.

Figure 10:
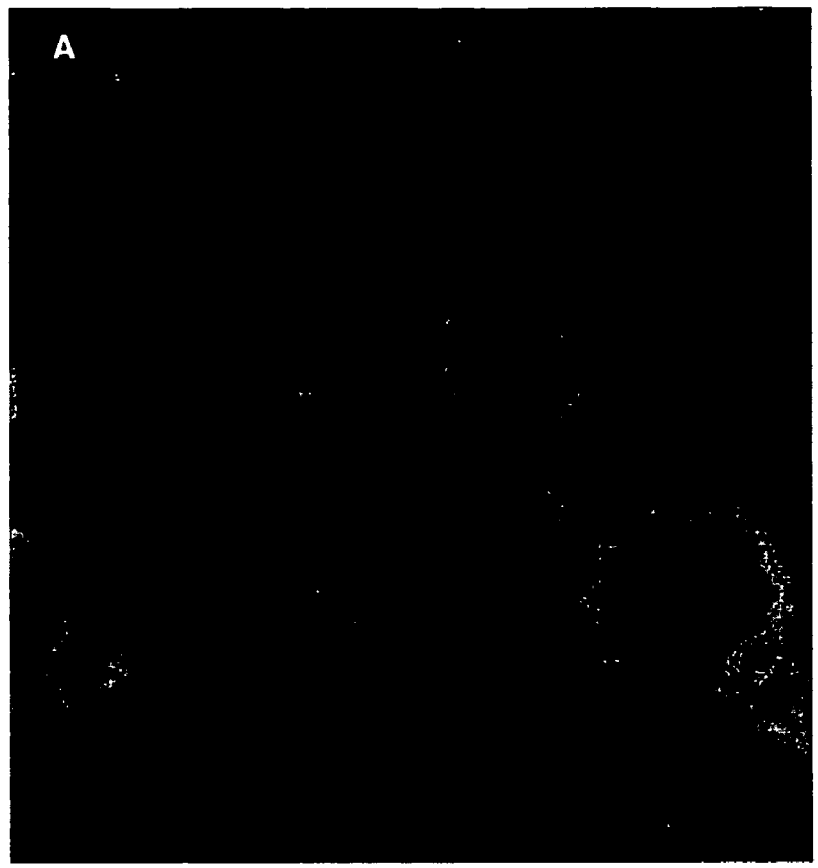
FIG. 10A shows a scanning confocal microscope images of 5-20 μm polymer vesicles featuring membrane-dispersed NIRF $PZn_3$.
FIG. 10B shows in situ fluorescence image of a 10 mL sample tube containing 5 mL a $PZn_3$-based aqueous NIR-emissive polymersome solution.
Figure 10:
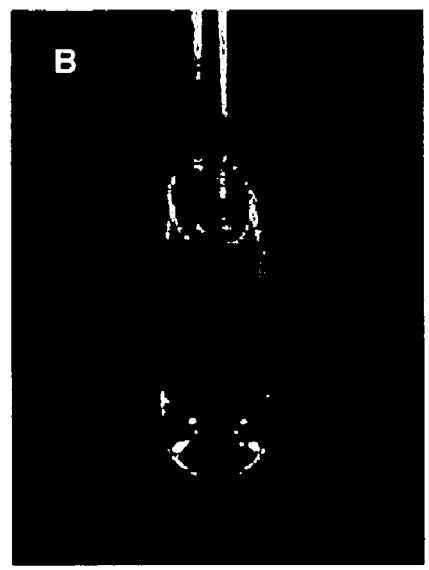
Figure 11:
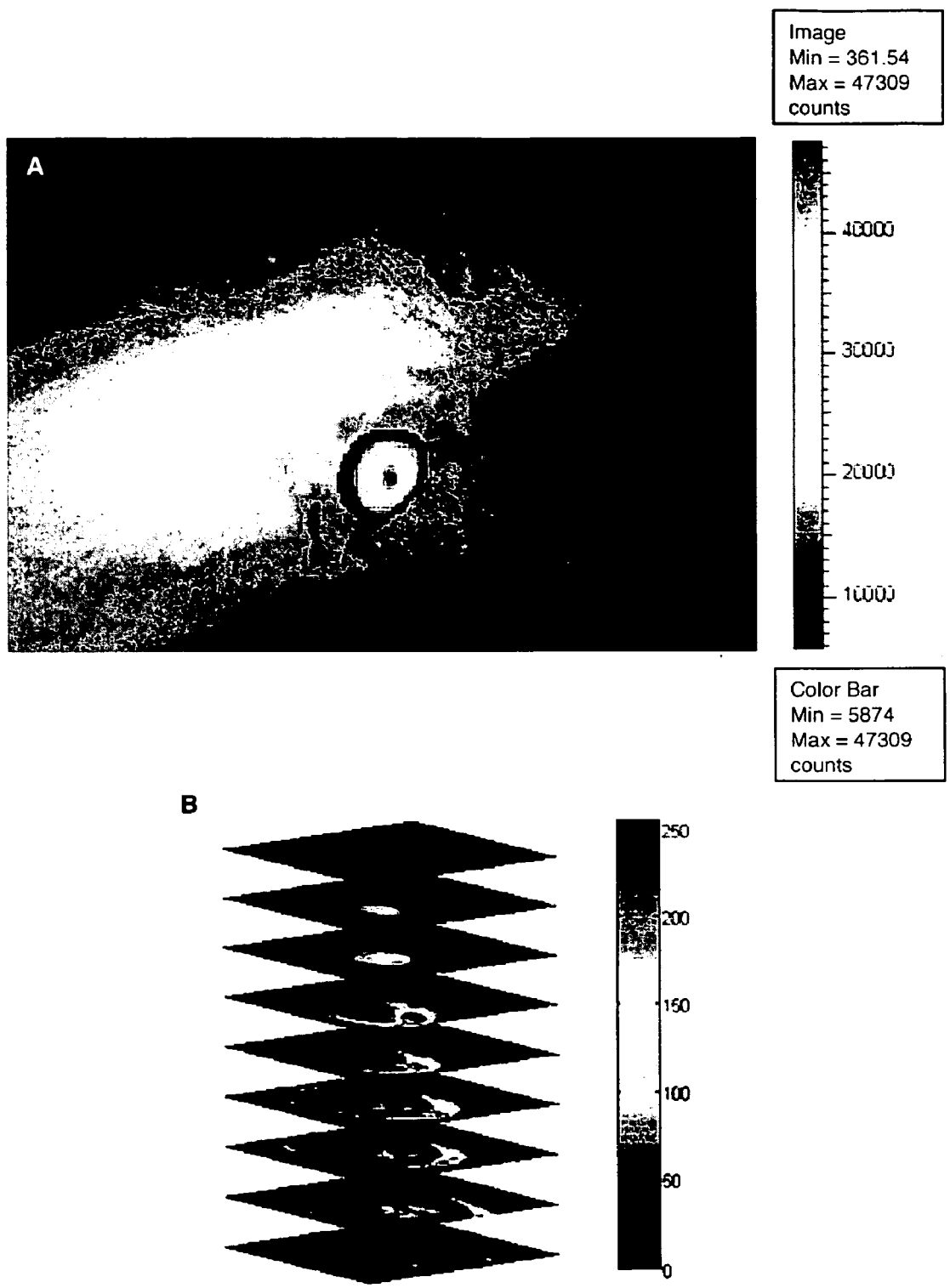
FIG. 11A shows an in vivo image of fluorescence arising from NIR-emissive polymersomes located within the tumor of a 9 L glioma-bearing Fisher rat as obtained using a Xenogen Ivis Imaging System.
FIG. 11B shows a high resolution 3D fluorescence scanning image of the same tumor obtained via a low-temperature optical imaging system.

~20 μg of NIR-emissive polymersomes (loaded with 5 mol % $PZn_3$) were introduced into the center of a 2 cm diameter subcutaneous tumor of a 9 L glioma-bearing Fisher rat. Both band-pass excitation (705-765 nm) and emission filters (805-880 nm) were not optimal for NIRF $PZn_3$; nevertheless, a high ratio of fluorescence signal-to-background was obtained, corresponding to only half the integrated emission from the vesicles. The fluorescence image of live animal is depicted in FIG. 10. The signal intensity remained constant during successive images taken over the next 1.5 h.

Example 28

High Resolution 3D Fluorescence Scanning of Injected Tumor via Low-Temperature Optical Imaging System Low temperature 3D fluorometric scanning was utilized in order to provide greater spatial resolution of the NIR-emissive polymersome signal emanating from deep within the tumor (as described in Example 23). A snap freeze-clamping technique was used to control the metabolic state of the tissue and to keep it constant for subsequent fluorescence measurements; it is necessary to freeze the tissue in order to preserve its metabolic state as well as to improve the signal-to-nose ratio so as to provide maximal spatial resolution. The animal was immersed in precooled isopentane (−150° C.) for 5 minutes and subsequently transferred to liquid nitrogen (−196° C.). The tumors was then surgically excised, embedded in a mixture of ethanol-glycerol-water (freeze point: −30° C.), and mounted at low temperature for high resolution fluorescence imaging via a 3D surface scanning optical system.

The optical scanning system utilizes a specialized cold mirror (650DRXRU, R:300/600 nm T:700-900 nm, Chroma Technology Corp), a 780 nm laser diode NIR excitation source (30 MW, Sharp Corp.), and a PMT detector (R928, Hamamatsu Inc) equipped with filters for specific NIR excitation (820+/−5 nm, Omega Optical Inc) and emission (830+/−10 nm, o.d.>5.5, Omega Optical Inc). The frozen tumor sample was milled flat and imaged every 100-200 μm from the top surface of the tumor parenchyma through the sample area containing the population of injected NIR-emissive polymersomes. Two step-motors drive optical fiber bundles to scan over the tissue surface (70 μm from the fused end of the fiber bundle to the surface) in the X, Y plane for projection of a 2D image. The resolution of each pixel is 80×80 μm2. The scanning was performed at 128×128 steps that covered 1.024×1.024 μm2 of tumor area. Two other step-motors control movement of the sample chamber in the X, Z plane, delivering the tissue sample to its designated position for milling and for measurements. The resolution in the Z direction is 10 μm corresponding to the thickness of the tissue sample. The fluorescence signal was automatically digitized and recorded on a PC and the 3D tumor image was generated with MATLAB software.

During the 2 h time interval following injection, diffusion of these 300 nm-sized polymersomes through the dense tumor parenchyma is limited.

All patents, publications, and other documents cited herein are hereby incorporated by reference in their entirety.

What is claimed:

1. A polymersome comprising:
   (i) a plurality of amphiphilic copolymers comprising amphiphilic block copolymers that comprise at least one hydrophilic polymer bonded to at least one hydrophobic polymer; and
   (ii) at least one visible- or near infrared-emissive agent that is dispersed within the polymersome membrane, where said emissive agent emits light in the 700-1100 nm spectral regime and where said emissive agent is an emissive conjugated compound comprising at least two covalently bound moieties; whereby upon exposing said compound to an energy source for a time and under conditions effective to cause said compound to emit light that at a wavelength between 700-1100 nm, said compound exhibits an integral emission oscillator strength that is greater than the emission oscillator strength manifest by either one of the said moieties individually; wherein said emissive agent comprises at least two porphyrin moieties, said porphyrin moieties being linked by a hydrocarbon bridge comprising at least one unsaturated moiety.

2. The polymersome of claim 1 where at least one of the emissive agent is an emissive conjugated compound comprising at least two covalently bound moieties; whereby upon exposing said compound to an energy source for a time and under conditions effective to cause said compound to emit light at a wavelength between 700-1100 nm, is of an intensity that is greater than a sum of light emitted by either of covalently bound moieties individually.

3. A polymersome as in claim 2 where the covalently bound moieties that define the emissive species are linked by at least one carbon-carbon double bond, carbon-carbon triple bond, or a combination thereof.

4. A polymersome as in claim 2 where the covalently bound moieties that define the emissive species are linked by ethynyl, ethenyl, allenyl, butadiynyl, polyvinyl, thiophenyl, furanyl, pyrrolyl, or p-diethylylarenyl linkers or by a conjugated heterocycle that bears diethynyl, di(polyynynyl), divinyl, di(polyvinyl), or di(thiophenyl) substituents.

5. The polymersome of claim 1 where said polymersome is bioresorbable.

6. The polymersome of claim 1 wherein the said emissive agent is an ethynyl- or butadiynyl-bridged multi(porphyrin) compound that features a β-to-β, meso-to-β, or meso-to-meso linkage topology, and the porphinato imaging agent being capable of emitting in the 700-to-1100 nm spectral regime.

7. The polymersome of claim 6 wherein the emissive agent is of the formula:

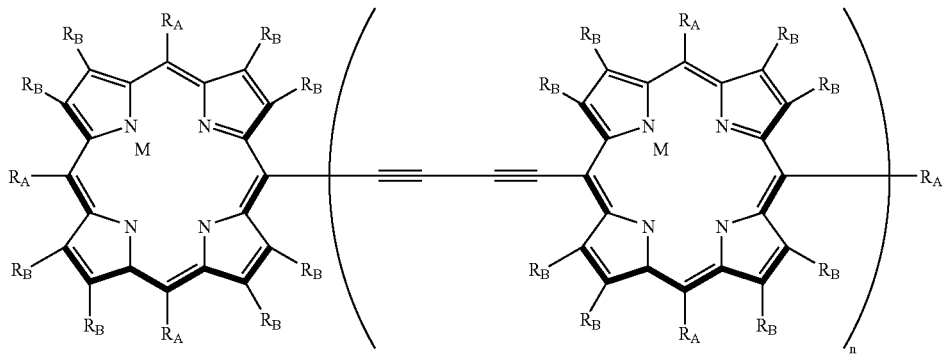

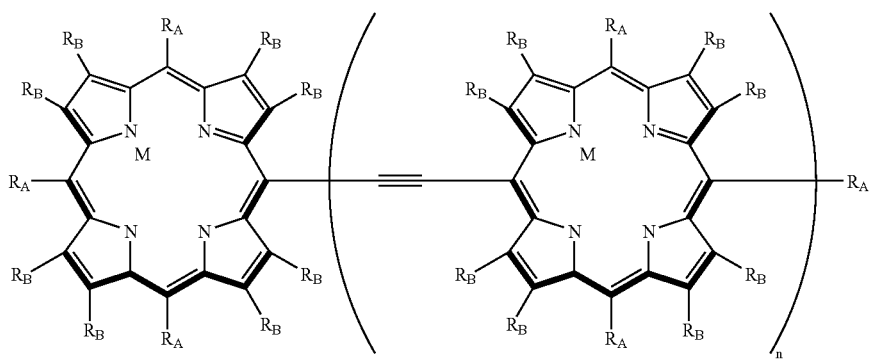

where M is a metal or $H_2$, where $H_2$ denotes the free ligand form of the macrocycle;

$R_A$ and $R_B$ are each, independently, H, $C_1$-$C_{20}$ alkyl or $C_1$-$C_{20}$ heteroalkyl, $C_6$-$C_{20}$ aryl or heteroaryl, $C(R_C)=C(R_D)(R_E)$, $C\equiv C(R_D)$, or a chemical functional group comprising a peptide, nucleoside or saccharide where $R_C$, $R_D$ and $R_E$ are each independently, H, F, Cl, Br, I, $C_1$-$C_{20}$ alkyl or $C_4$-$C_{20}$ heteroalkyl, aryl or heteroaryl, $C_2$-$C_{20}$ alkenyl or heteroalkenyl, alkynyl or $C_2$-$C_{20}$ heteroalkynyl, trialkylsilyl, or porphyrinato;

and n is an integer from 1 to 10.

8. The polymersome of claim 7 where n is an integer from 1 to 8.

9. The polymersome of claim 7 where M of the emissive agent is zinc, magnesium, platinum, palladium, or $H_2$, where $H_2$ denotes the free ligand form of the macrocycle.

10. The polymersome of claim 7 where said polymersome porphyrin-based imaging agent is emissive.

11. The polymersome of 7, wherein the said emissive agent comprises a meso-to-meso ethyne- or butadiyne-bridged linkage topology, said imaging agent being capable of emitting in the 700-to-1100 nm spectral regime.

12. The polymersome of claim 1 wherein said polymersome comprises one amphiphilic block co-polymer.

13. The polymersome of claim 1 wherein said amphiphilic block co-polymer comprises one hydrophobic polymer and one hydrophilic polymer.

14. The polymersome of claim 1 wherein said amphiphilic block co-polymer is a triblock polymer comprising terminal hydrophilic polymers and a hydrophobic internal polymer.

15. The polymersome of claim 1 wherein said amphiphilic block co-polymer is a tetrablock polymer comprising two hydrophilic polymer blocks and two hydrophobic polymer blocks.

16. The polymersome of claim 15 comprising terminal hydrophilic polymer blocks and internal hydrophobic polymer blocks.

17. The polymersome of claim 1 wherein said amphiphilic block co-polymer is a pentablock polymer comprising two hydrophilic polymer blocks and three hydrophobic polymer blocks.

18. The polymersome of claim 1 wherein said amphiphilic block co-polymer is a pentablock polymer comprising three hydrophilic polymer blocks and two hydrophobic polymer blocks.

19. The polymersome of claim 1 wherein said amphiphilic block co-polymer is a pentablock polymer comprising four hydrophilic polymer blocks and one hydrophobic polymer block.

20. The polymersome of claim 1 wherein said amphiphilic block co-polymer comprises at least six block, at least two of which are hydrophilic polymer blocks.

21. The polymersome of claim 1 further comprising at least one lipid, phospholipid, steroid, cholesterol, single chain alcohol, peptide, or surfactant.

22. The polymersome of claim 1 wherein the amphiphilic co-polymer is made by attaching two strands comprising different monomers.

23. The polymersome of claim 1 wherein the amphiphilic co-polymer comprises polymers made by free radical initiation, anionic polymerization, peptide synthesis, or ribosomal synthesis using transfer RNA.

24. The polymersome of claim 1 wherein the hydrophilic polymer comprises poly(ethylene oxide) or poly(ethylene glycol).

25. The polymersome of claim 1 wherein the hydrophilic polymer is soluble in water.

26. The polymersome of claim 1 wherein the hydrophilic polymer comprises polymerized units selected from ionically polymerizable polar monomers.

27. The polymersome of claim 26 wherein the ionically polymerizable polar monomers comprise an alkyl oxide monomer.

28. The polymersome of claim 27 wherein the alkyl oxide monomer is ethylene oxide, propylene oxide, or any combination thereof.

29. The polymersome of claim 1 wherein the hydrophilic polymer comprises poly(ethylene oxide).

30. The polymersome of claim 1 wherein the volume fraction of the hydrophilic polymers in the plurality of amphiphilic block copolymers is less than or equal to 0.40.

31. The polymersome of claim 1 wherein the hydrophobic polymer comprises polyethylethylene, poly(butadiene), poly($\beta$-benzyl-L-aspartate), poly(lactic acid), poly(propylene oxide), poly($\epsilon$-caprolactam), oligo-methacrylate, or polystyrene.

32. The polymersome of claim 1 wherein the hydrophobic polymer comprises polyethylethylene or poly(butadiene).

33. The polymersome of claim 1 wherein the hydrophobic polymer comprises polymerized units selected from unsaturated monomers.

34. The polymersome of claim 33 wherein the unsaturated monomers are hydrocarbons.

35. The polymersome of claim 1 where said polymersome contains a hydrophobic polycaprolactone, polylacticde, polyglycolide, or polymethylene carbonate polymer block used in combination with a corresponding polyethyleneoxide polymer block.

36. The polymersome of claim 1 wherein the amphiphilic block copolymer is poly(ethylene oxide)-polyethylethylene, poly(ethylene oxide)-poly(butadiene), poly(ethylene oxide)-poly($\epsilon$-caprolactone) or poly(ethylene oxide)-poly(lactic acid).

37. The polymersome of claim 1 additionally comprising a therapeutic agent.

38. The polymersome of claim 1 additionally comprising one or more distinct emissive species.

39. The polymersome of claim 1 additionally comprising at least one of a secondary emitter, a cytotoxic agent, a magnetic resonance imaging (MRI) agent, positron emission tomography (PET) agent, radiological imaging agent or a photodynamic therapy (PDT) agent.

40. The polymersome of claim 1 additionally comprising at least one of a secondary emitter, a cytotoxic agent, a magnetic resonance imaging (MRI) agent, positron emission tomography (PET) agent, photodynamic therapy (PDT) agent, radiological imaging agent, ferromagnetic agent, or ferrimagnetic agent, where said emitter or agent is compartmentalized within the aqueous polymersome interior.

41. The polymersome of claim 1 additionally comprising a protein, peptide, saccharide, nucleoside, inorganic compound, biological entity such as a virus, organelle, bacterium, or cellular component, or organic compound compartmentalized within the aqueous polymersome interior.

42. A polymersome comprising:
   (i) a membrane comprising a plurality of amphiphilic copolymers comprising amphiphilic block copolymers that comprise at least one hydrophilic polymer bonded to at least one hydrophobic polymer;
   (ii) at least one emissive agent that emits light at a wavelength between 700-1100 where said emissive agent is an emissive conjugated compound comprising at least two covalently bound moieties; whereby upon exposing said compound to an energy source for a time and under conditions effective to cause said compound to emit light that at a wavelength between 700-1100 nm, said compound exhibits an integral emission oscillator strength that is greater than the emission oscillator strength manifest by either one of the said moieties individually; wherein said emissive agent comprises at least two porphyrin moieties, said porphyrin moieties being linked by a hydrocarbon bridge comprising at least one unsaturated moiety; and
   (iii) at least one targeting moiety associated with a surface of the polymersome.

43. The polymersome of claim 42 where at least one of the emissive agent is an emissive conjugated compound comprising at least two covalently bound moieties; whereby upon exposing said compound to an energy source for a time and under conditions effective to cause said compound to emit light at a wavelength between 700-1100 nm, is of an intensity that is greater than a sum of light emitted by either of covalently bound moieties individually.

44. A polymersome as in claim 43 where the covalently bound moieties that define the emissive species are linked by at least one carbon-carbon double bond, carbon-carbon triple bond, or a combination thereof.

45. A polymersome as in claim 43 where the covalently bound moieties that define the emissive species are linked by ethynyl, ethenyl, allenyl, butadiynyl, polyvinyl, thiophenyl, furanyl, pyrrolyl, p-diethylylarenyl or any conjugated heterocycle that bears diethynyl, di(polyynynyl), divinyl, di(polyvinvyl), or di(thiophenyl) substituents.

46. The polymersome of claim 42 where said polymersome is bioresorbable.

47. The polymersome of claim 46 where said polymersome contains a hydrophobic polycaprolactone, polylacticde, polyglycolide, or polymethylene carbonate polymer block used in combination with a corresponding polyethyleneoxide polymer block.

48. The polymersome of claim 42 where said polymersome contains block polymer components approved by the United States Food and Drug Administration (FDA) for use in vivo.

49. The polymersome of claim 42 wherein the targeting moiety specifically binds with a biological situs.

50. The polymersome of claim 42 wherein the targeting moiety specifically binds with a biological situs under physiological conditions.

51. The polymersome of claim 42 wherein the said emissive agent is an ethynyl- or butadiynyl-bridged multi(porphyrin) compound that features a $\beta$-to-$\beta$, meso-to-$\beta$, or meso-to-meso linkage topology, and the porphinato imaging agent being capable of emitting in the 700-to-1100 nm spectral regime.

52. The polymersome of claim 51 wherein the emissive agent is of the formula:

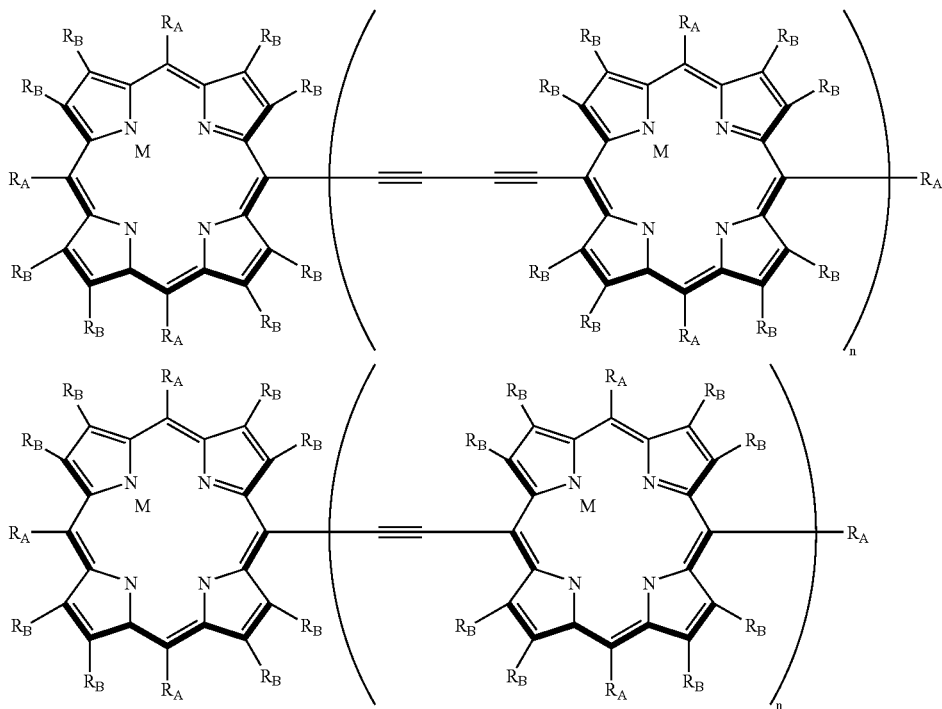

where M is a metal or $H_2$, where $H_2$ denotes the free ligand form of the macrocycle;

$R_A$ and $R_B$ are each, independently, H, alkyl or $C_1$-$C_{20}$ heteroalkyl, $C_6$-$C_{20}$ aryl or heteroaryl, $C(R_C)\!=\!C(R_D)(R_E)$, $C\!\equiv\!C(R_D)$, or a chemical functional group comprising a peptide, nucleoside or saccharide where $R_C$, $R_D$ and $R_E$ are each independently, H, F, Cl, Br, I, $C_1$-$C_{20}$ alkyl or $C_4$-$C_{20}$ heteroalkyl, aryl or heteroaryl, $C_2$-$C_{20}$ alkenyl or heteroalkenyl, alkynyl or $C_2$-$C_{20}$ heteroalkynyl, trialkylsilyl, or porphyrinato;

and n is an integer from 1 to 10.

53. The polymersome of claim 52 where n is an integer from 1 to 8.

54. The polymersome of claim 53 where M of the emissive agent is zinc, magnesium, platinum, palladium, or $H_2$, where $H_2$ denotes the free ligand form of the macrocycle.

55. The polymersome of claim 42 where said polymersome porphyrin-based imaging agent is emissive.

56. The polymersome of claim 42, wherein the said emissive agent comprises a meso-to-meso ethyne- or butadiyne-bridged linkage topology, said imaging agent being capable of emitting in the 700-to-1100 spectral regime.

57. The polymersome of claim 42 wherein the targeting moiety comprises an antibody, antibody fragment, or substance specific for a given receptor binding site.

58. The polymersome of claim 57 wherein the receptor binding site, or targeting moiety comprises a receptor-specific peptide, carbohydrate, protein, lipid, nucleoside, peptide nucleic acid, organic compound, or combinations thereof.

59. The polymersome of claim 42 wherein said polymersome comprises one amphiphilic block co-polymer.

60. The polymersome of claim 42 wherein said amphiphilic block co-polymer comprises one hydrophobic polymer and one hydrophilic polymer.

61. The polymersome of claim 42 wherein said amphiphilic block co-polymer is a triblock polymer comprising terminal hydrophilic polymers and a hydrophobic internal polymer.

62. The polymersome of claim 42 wherein said amphiphilic block co-polymer is a tetrablock polymer comprising two hydrophilic polymer blocks and two hydrophobic polymer blocks.

63. The polymersome of claim 62 comprising terminal hydrophilic polymer blocks and internal hydrophobic polymer blocks.

64. The polymersome of claim 42 wherein said amphiphilic block co-polymer is a pentablock polymer comprising two hydrophilic polymer blocks and three hydrophobic polymer blocks.

65. The polymersome of claim 42 wherein said amphiphilic block co-polymer is a pentablock polymer comprising three hydrophilic polymer blocks and two hydrophobic polymer blocks.

66. The polymersome of claim 42 wherein said amphiphilic block co-polymer is a pentablock polymer comprising four hydrophilic polymer blocks and one hydrophobic polymer block.

67. The polymersome of claim 42 wherein said amphiphilic block co-polymer comprises at least six block, at least two of which are hydrophilic polymer blocks.

68. The polymersome of claim 42 further comprising at least one lipid, phospholipid, steroid, cholesterol, single chain alcohol, peptide, or surfactant.

69. The polymersome of claim 42 wherein the amphiphilic co-polymer is made by attaching two strands comprising different monomers.

70. The polymersome of claim 42 wherein the amphiphilic co-polymer comprises polymers made by free radical initiation, anionic polymerization, peptide synthesis, or ribosomal synthesis using transfer RNA.

71. The polymersome of claim 42 wherein the hydrophilic polymer comprises poly(ethylene oxide) or poly(ethylene glycol).

72. The polymersome of claim 42 wherein the hydrophilic polymer is soluble in water.

73. The polymersome of claim 42 wherein the hydrophilic polymer comprises polymerized units selected from ionically polymerizable polar monomers.

74. The polymersome of claim 73 wherein the ionically polymerizable polar monomers comprise an alkyl oxide monomer.

75. The polymersome of claim 74 wherein the alkyl oxide monomer is ethylene oxide, propylene oxide, or any combination thereof.

76. The polymersome of claim 71 wherein the hydrophilic polymer comprises poly(ethylene oxide).

77. The polymersome of claim 76 wherein the volume fraction of the hydrophilic polymers in the plurality of amphiphilic block copolymers is less than or equal to 0.40.

78. The polymersome of claim 42 wherein the hydrophobic polymer comprises polyethylethylene, poly(butadiene), poly(β-benzyl-L-aspartate), poly(lactic acid), poly(propylene oxide), poly(ε-caprolactam), oligo-methacrylate, or polystyrene.

79. The polymersome of claim 78 wherein the hydrophobic polymer comprises polyethylethylene or poly(butadiene).

80. The polymersome of claim 78 wherein the hydrophobic polymer comprises polymerized units selected from ethylenically unsaturated monomers.

81. The polymersome of claim 79 wherein the ethylenically unsaturated monomers are hydrocarbons.

82. The polymersome of claim 42 wherein the amphiphilic block copolymer is poly(ethylene oxide)-polyethylethylene, poly(ethylene oxide)-poly(butadiene), poly(ethylene oxide)-poly(ε-caprolactone) or poly(ethylene oxide)-poly(lactic acid).

83. The polymersome of claim 42 additionally comprising a therapeutic agent.

84. The polymersome of claim 42 additionally comprising one or more distinct emissive species.

85. The polymersome of claim 42 additionally comprising at least one of a secondary emitter, a cytotoxic agent, a magnetic resonance imaging (MRI) agent, positron emission tomography (PET) agent, radiological imaging agent or a photodynamic therapy (PDT) agent.

86. The polymersome of claim 42 additionally comprising at least one of a secondary emitter, a cytotoxic agent, a magnetic resonance imaging (MRI) agent, positron emission tomography (PET) agent, photodynamic therapy (PDT) agent, radiological imaging agent, ferromagnetic agent, or ferrimagnetic agent, where said emitter or agent is compartmentalized within the aqueous polymersome interior.

87. The polymersome of claim 42 additionally comprising a protein, peptide, saccharide, nucleoside, inorganic compound, biological entity such as a virus, organelle, bacterium, or cellular component, or organic compound compartmentalized within the aqueous polymersome interior.

88. A method of delivering an agent to a biological situs in a tissue or organism comprising administering to the tissue or organism a polymersome having the agent and comprising (a) a membrane comprising a plurality of amphiphilic copolymers comprising amphiphilic block copolymers that comprise at least one hydrophilic polymer bonded to at least one hydrophobic polymer; (b) at least one emissive agent which emits light at a wavelength between 700-1100 nm where said emissive agent is an emissive conjugated compound comprising at least two covalently bound moieties; whereby upon exposing said compound to an energy source for a time and under conditions effective to cause said compound to emit light that at a wavelength between 700-1100 nm, said compound exhibits an integral emission oscillator strength that is greater than the emission oscillator strength manifest by either one of the said moieties individually; wherein said emissive agent comprises at least two porphyrin moieties, said porphyrin moieties being linked by a hydrocarbon bridge comprising at least one unsaturated moiety; and (c) at least one targeting moiety associated with a surface of the polymersome.

89. The method of claim 88 further comprising determining when a selected amount of the polymersome is at the situs; and liberating at least a portion of the agent.

90. The method of claim 88 wherein said phorphinato imaging agent is an ethynyl- or butadiynyl-bridged multi (porphyrin) compound that features a β-to-β, meso-to-β, or meso-to-meso linkage topology, and the porphinato imaging agent being capable of emitting in the 700-to-1100 nm spectral regime.

91. The method of claim 88 where at least one of the emissive agent is an emissive conjugated compound comprising at least two covalently bound moieties; whereby upon exposing said compound to an energy source for a time and under conditions effective to cause said compound to emit light at a wavelength between 700-1100 nm, is of an intensity that is greater than a sum of light emitted by either of covalently bound moieties individually.

92. The method of claim 88 wherein the emissive agent is of the formula:

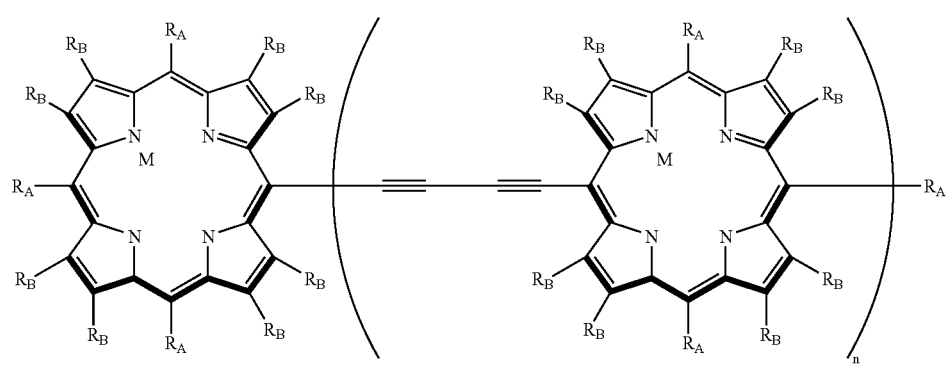

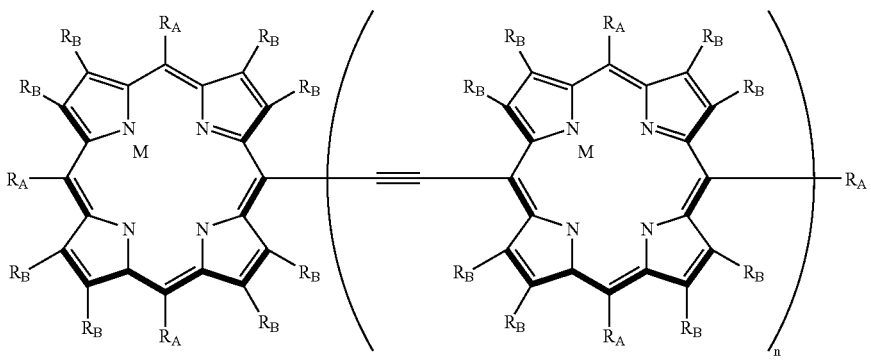

where M is a metal or $H_2$, where $H_2$ denotes the free ligand form of the macrocycle;

$R_A$ and $R_B$ are each, independently, H, alkyl or $C_1$-$C_{20}$ heteroalkyl, $C_6$-$C_{20}$ aryl or heteroaryl, $C(R_C)\!\!=\!\!C(R_D)(R_E)$, $C\!\!\equiv\!\!C(R_D)$, or a chemical functional group comprising a peptide, nucleoside or saccharide where $R_C$, $R_D$ and $R_E$ are each independently, H, F, Cl, Br, I, $C_1$-$C_{20}$ alkyl or $C_4$-$C_{20}$ heteroalkyl, aryl or heteroaryl, $C_2$-$C_{20}$ alkenyl or heteroalkenyl, alkynyl or $C_2$-$C_{20}$ heteroalkynyl, trialkylsilyl, or porphyrinato;

and n is an integer from 1 to 10.

93. The method of claim 90 wherein the targeting moiety comprises an antibody, antibody fragment, or substance specific for a given receptor binding site.

94. The method of claim 93 wherein the receptor binding site, or substance, comprises a receptor-specific peptide, carbohydrate, protein, lipid, nucleoside, peptide nucleic acid, or combinations thereof.

95. The method of claim 90 wherein the hydrophilic polymer comprises poly(ethylene oxide) or poly(ethylene glycol).

96. The method of claim 95 wherein the hydrophilic polymer comprises poly(ethylene oxide).

97. The method of claim 96 wherein the volume fraction of hydrophilic polymers in the plurality of amphiphilic block copolymers is less than or equal to 0.40.

98. The method of claim 95 wherein the hydrophobic polymer comprises polyethylethylene, poly(1,2-butadiene), poly(β-benzyl-L-aspartate), poly(lactic acid), poly(propylene oxide), poly(ε-caprolactam), oligo-methacrylate, or polystyrene.

99. The method of claim 98 wherein the hydrophobic polymer comprises polyethylethylene or poly(1,2-butadiene).

100. The method of claim 88 wherein the amphiphilic block copolymer comprises poly(ethylene oxide)-polyethylethylene, poly(ethylene oxide)-poly(butadiene), poly(ethylene oxide)-poly(ε-caprolactone) or poly(ethylene oxide)-poly(lactic acid).

101. The method of claim 89 wherein the therapeutic agent is liberated using ultrasonic energy to disrupt the structure of the polymersome.

102. The method of claim 89 wherein the therapeutic agent is liberated using light energy to disrupt the structure of the polymersome.

103. The method of claim 89 wherein the therapeutic agent is liberated using enzymatic degradation of polymeric components of the polymersome.

104. A method of ascertaining the presence or absence of a disease state in an organism or tissue comprising:

administering a polymersome to a patient, the polymersome comprising (a) a membrane comprising a plurality of amphiphilic copolymers comprising amphiphilic block copolymers that comprise at least one hydrophilic polymer bonded to at least one hydrophobic polymer; (b) at least one emissive agent that emits light at a wavelength between 700-1100 nm where said emissive agent is an emissive conjugated compound comprising at least two covalently bound moieties; whereby upon exposing said compound to an energy source for a time and under conditions effective to cause said compound to emit light that at a wavelength between 700-1100 nm, said compound exhibits an integral emission oscillator strength that is greater than the emission oscillator strength manifest by either one of the said moieties individually; wherein said emissive agent comprises at least two porphyrin moieties, said porphyrin moieties being linked by a hydrocarbon bridge comprising at least one unsaturated moiety; and (c) at least one targeting moiety associated with a surface of the polymersome;

providing an instrument optically coupled to a light source, a light detector, or both, and operating the instrument to monitor the amount or distribution of the phorphinato imaging agent within the organism or tissue.

105. The method of claim 104 wherein the phorphinato imaging agent is an ethynyl- or butadiynyl-bridged multi (porphyrin) compound that features a β-to-β, meso-to-β, or meso-to-meso linkage topology, and the porphinato imaging agent being capable of emitting in the 700-to-1100 nm spectral regime.

106. The method of claim 105 wherein the phorphinato imaging agent is of the formula:

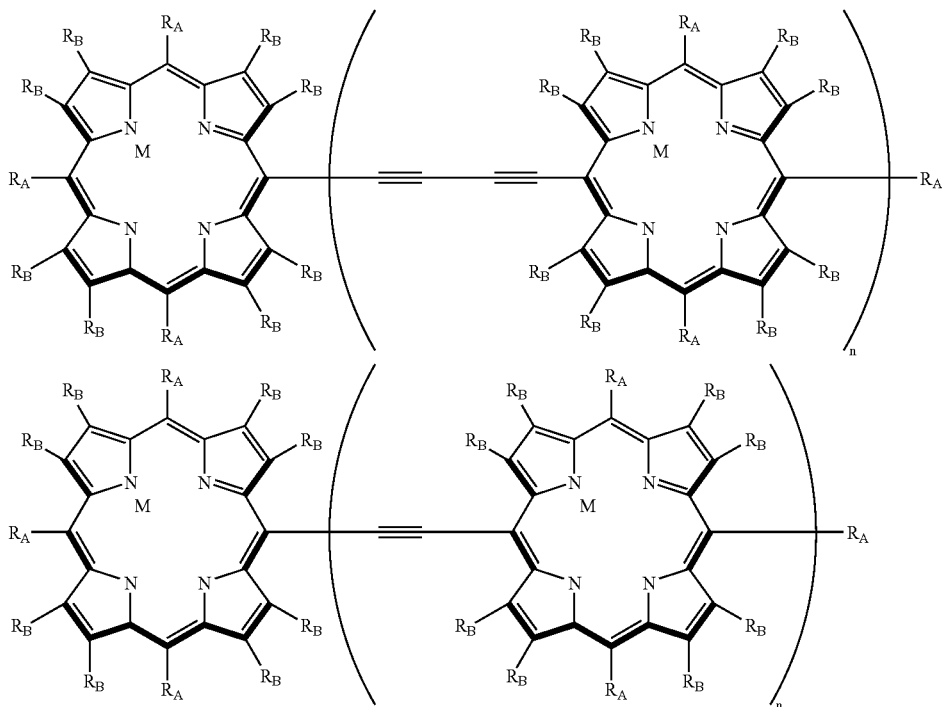

where M is a metal or $H_2$, where $H_2$ denotes the free ligand form of the macrocycle;

$R_A$ and $R_B$ are each, independently, H, alkyl or $C_1$-$C_{20}$ heteroalkyl, $C_6$-$C_{20}$ aryl or heteroaryl, $C(R_C)$=$C(R_D)$ $(R_E)$, C≡$C(R_D)$, or a chemical functional group comprising a peptide, nucleoside or saccharide where $R_C$, $R_D$ and $R_E$ are each independently, H, F, Cl, Br, I, $C_1$-$C_{20}$ alkyl or $C_4$-$C_{20}$ heteroalkyl, aryl or heteroaryl, $C_2$-$C_{20}$ alkenyl or heteroalkenyl, alkynyl or $C_2$-$C_{20}$ heteroalkynyl, trialkylsilyl, or porphyrinato;

and n is an integer from 1 to 10.

107. The method of claim 104 where at least one of the emissive agent is an emissive conjugated compound comprising at least two covalently bound moieties; whereby upon exposing said compound to an energy source for a time and under conditions effective to cause said compound to emit light at a wavelength between 700-1100 nm, is of an intensity that is greater than a sum of light emitted by either of covalently bound moieties individually.

108. The method of claim 104 wherein the targeting moiety comprises an antibody, antibody fragment, or substance specific for a given receptor binding site.

109. The method of claim 108 wherein the receptor binding site or substance comprises a receptor-specific peptide, carbohydrate, protein, lipid, nucleoside, peptide nucleic acid, or combinations thereof.

110. The method of claim 105 wherein the hydrophilic polymer comprises poly(ethylene oxide) or poly(ethylene glycol).

111. The method of claim 108 wherein the hydrophilic polymer comprises poly(ethylene oxide).

112. The method of claim 111 wherein the volume fraction of hydrophilic polymers in the plurality of amphiphilic block copolymers is less than or equal to 0.40.

113. The method of claim 110 wherein the hydrophobic polymer comprises polyethylethylene, poly(1,2-butadiene), poly(β-benzyl-L-aspartate), poly(lactic acid), poly(propylene oxide), poly(ε-caprolactam), oligo-methacrylate, or polystyrene.

114. The method of claim 113 wherein the hydrophobic polymer comprises polyethylethylene or poly(1,2-butadiene).

115. The method of claim 104 wherein the amphiphilic block copolymer is poly(ethylene oxide)-polyethylethylene, poly(ethylene oxide)-poly(butadiene), poly(ethylene oxide)-poly(ε-caprolactone) or poly(ethylene oxide)-poly(lactic acid).

116. The method of claim 104 additionally comprising at least one of a secondary emitter, a cytotoxic agent, a magnetic resonance imaging (MRI) agent, positron emission tomography (PET) agent, radiological imaging agent, radiological imaging agent or a photodynamic therapy (PDT) agent.

117. The method of claim 104 additionally comprising at least one of a secondary emitter, a cytotoxic agent, a magnetic resonance imaging (MRI) agent, positron emission tomography (PET) agent, radiological imaging agent or a photodynamic therapy (PDT) agent, where said emitter or agent is compartmentalized within the aqueous polymersome interior.

118. An in vivo method of diagnostics or imaging comprising:

contacting a polymersome with tissue within an organism, the polymersome comprising (a) a membrane comprising a plurality of amphiphilic copolymers comprising amphiphilic block copolymers that comprise at least one hydrophilic polymer bonded to at least one hydrophobic polymer; (b) at least one emissive agent that emits light at a wavelength between 700-1100 nm where said emissive agent is an emissive conjugated compound comprising at least two covalently bound moieties; whereby upon exposing said compound to an energy source for a time and under conditions effective to cause said compound to emit light that at a wavelength between 700-1100 nm, said compound exhibits an integral emission oscillator strength that is greater than the emission oscillator strength manifest by either one of the said moieties individually; wherein said emissive agent comprises at least two porphyrin moieties, said porphyrin moieties being linked by a hydrocarbon bridge comprising at least one unsaturated moiety; and (c) at least one targeting moiety associated with a surface of the polymersome;

providing an instrument optically coupled to a light source, a light detector, or both, and using the instrument to monitor the amount of the polymersome at a situs within the tissue.

119. The method of claim 118 wherein the said imaging agent is an ethynyl- or butadiynyl-bridged multi(porphyrin) compound that features a β-to-β, meso-to-β, or meso-to-meso linkage topology, and the porphinato imaging agent being capable of emitting in the 700-to-1100 nm spectral regime.

120. The method of claim 119 wherein the phorphinato imaging agent is of the formula:

121. The method of claim 118 wherein the targeting moiety comprises an antibody, antibody fragment, or substance specific for a given receptor binding site.

122. The method of claim 121 wherein the receptor binding site or substance comprises a receptor-specific peptide, carbohydrate, protein, lipid, nucleoside, peptide nucleic acid, or combinations thereof.

123. The method of claim 119 wherein the hydrophilic polymer comprises poly(ethylene oxide) or poly(ethylene glycol).

124. The method of claim 123 wherein the hydrophilic polymer comprises poly(ethylene oxide).

125. The method of claim 124 wherein the volume fraction of hydrophilic polymers in the plurality of amphiphilic block copolymers is less than or equal to 0.40.

126. The method of claim 123 wherein the hydrophobic polymer comprises polyethylethylene, poly(1,2-butadiene), poly(β-benzyl-L-aspartate), poly(lactic acid), poly(propylene oxide), poly(ε-caprolactam), oligo-methacrylate, or polystyrene.

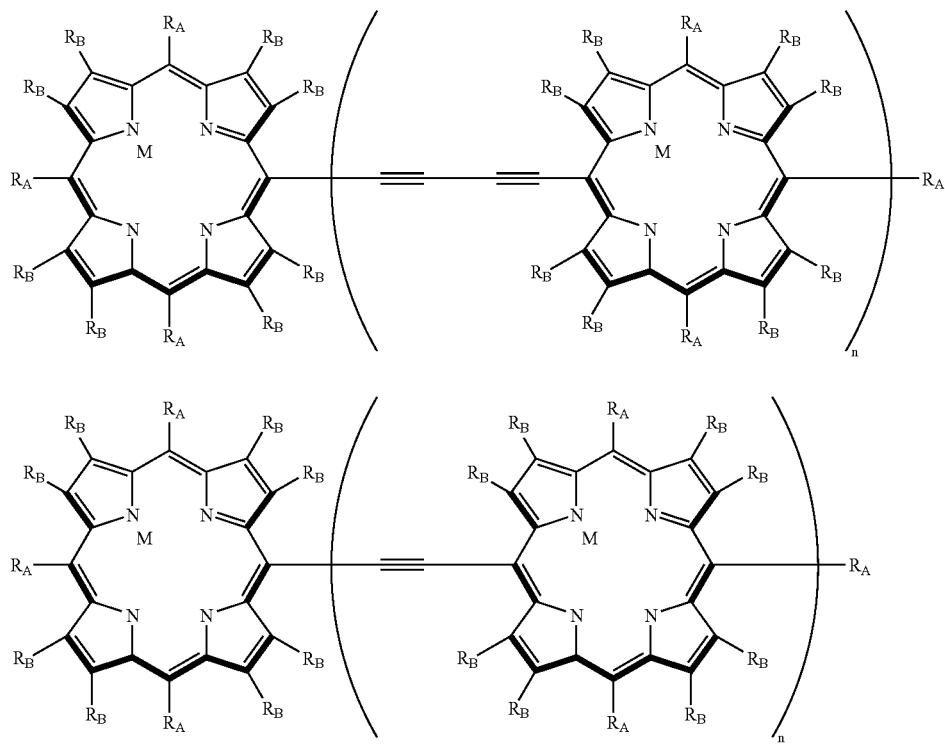

where M is a metal or $H_2$, where $H_2$ denotes the free ligand form of the macrocycle;

$R_A$ and $R_B$ are each, independently, H, alkyl or $C_1$-$C_{20}$ heteroalkyl, $C_6$-$C_{20}$ aryl or heteroaryl, $C(R_C)\!=\!C(R_D)$ $(R_E)$, $C\!\equiv\!C(R_D)$, or a chemical functional group comprising a peptide, nucleoside or saccharide where $R_C$, $R_D$ and $R_E$ are each independently, H, F, Cl, Br, I, $C_1$-$C_{20}$ alkyl or $C_4$-$C_{20}$ heteroalkyl, aryl or heteroaryl, $C_2$-$C_{20}$ alkenyl or heteroalkenyl, alkynyl or $C_2$-$C_{20}$ heteroalkynyl, trialkylsilyl, or porphyrinato;

and n is an integer from 1 to 10.

127. The method of claim 126 wherein the hydrophobic polymer comprises polyethylethylene or poly(1,2-butadiene).

128. The method of claim 118 wherein the amphiphilic block copolymer is poly(ethylene oxide)-polyethylethylene, poly(ethylene oxide)-poly(butadiene), poly(ethylene oxide)-poly(ε-caprolactone) or poly(ethylene oxide)-poly(lactic acid).

129. An in vitro diagnostic method comprising:

contacting a polymersome with isolated cells, mixtures of cells, or specific cell lines, with the polymersome comprising (a) a membrane comprising a plurality of amphiphilic copolymers comprising amphiphilic block copolymers that comprise at least one hydrophilic polymer bonded to at least one hydrophobic polymer; (b) at least one emissive agent that is dispersed within the polymersome membrane, at least one that emits light at a wavelength between 700-1100 nm where said emissive agent is an emissive conjugated compound comprising at least two covalently bound moieties; whereby upon exposing said compound to an energy source for a time and under conditions effective to cause said compound to emit light that at a wavelength between 700-1100 nm, said compound exhibits an integral emission oscillator strength that is greater than the emission oscillator strength manifest by either one of the said moieties individually; wherein said emissive agent comprises at least two porphyrin moieties, said porphyrin moieties being linked by a hydrocarbon bridge comprising at least one unsaturated moiety; and (c) at least one targeting moiety associated with a surface of the polymersome;

providing an instrument optically coupled to a light source, a light detector, or both, and using the instrument to monitor cell-surface-to-polymersome binding.

130. The method of claim 129 wherein the targeting moiety targets cancer cells allowing the method to be utilized for real-time cancer detection.

131. The method of claim 129 wherein more than one emissive agent is used, each emissive agent having a different emissive signature, and further comprising the step of creating a panoply of unique histological markers for multiple distinct biomarkers for in vitro diagnosis.

132. A method for histological labeling, molecular classification of cell surface markers, or guiding the development of novel directed therapeutic strategies, comprising contacting a polymersome with isolated cells, mixtures of cells, or specific cell lines, with the polymersome comprising (a) a membrane comprising a plurality of amphiphilic copolymers comprising amphiphilic block copolymers that comprise at least one hydrophilic polymer bonded to at least one hydrophobic polymer; (b) at least one emissive agent that is dispersed within the polymersome membrane, at least one that emits light at a wavelength between 700-1100 nm where said emissive agent is an emissive conjugated compound comprising at least two covalently bound moieties; whereby upon exposing said compound to an energy source for a time and under conditions effective to cause said compound to emit light that at a wavelength between 700-1100 nm, said compound exhibits an integral emission oscillator strength that is greater than the emission oscillator strength manifest by either one of the said moieties individually; wherein said emissive agent comprises at least two porphyrin moieties, said porphyrin moieties being linked by a hydrocarbon bridge comprising at least one unsaturated moiety; and (c) at least one targeting moiety associated with a surface of the polymersome;

providing an instrument optically coupled to a light source, a light detector, or both, and using the instrument to monitor cell-surface-to-polymersome binding.

133. A method of modulating the emission properties of a visible- or near infrared-emissive agent, wherein said emissive agent emits light in the 700-1100 nm spectral regime and wherein said emissive agent is an emissive conjugated compound comprising at least two covalently bound moieties; whereby upon exposing said compound to an energy source for a time and under conditions effective to cause said compound to emit light that at a wavelength between 700-1100 nm, and exhibits an integral emission oscillator strength that is greater than the emission oscillator strength manifest by either one of the said moieties individually; wherein said emissive agent comprises at least two porphyrin moieties, said porphyrin moieties being linked by a hydrocarbon bridge comprising at least one unsaturated moiety; said emissive agent being within a polymeric material, wherein at least one of the bound moieties comprises an ancillary substituent, the size and chemical constitution of said substituent being selected to provide said modulation.

134. The method of claim 133 wherein said modulation is of the steady state emission wavelength.

135. The method of claim 133 wherein said modulation is of the time-dependent emission dynamics of said emissive conjugated compound.

136. The method of claim 133, wherein the said emissive agent is a multi(porphyrin) imaging agent comprises a meso-to-meso ethyne- or butadiyne-bridged linkage topology, said imaging agent being capable of emitting in the 700-to-1100 nm spectral regime.

137. The method of claim 133 wherein the said emissive agent comprises at least two covalently bound moieties; whereby upon exposing said agent to an energy source for a time and under conditions effective to cause said compound to emit light at a wavelength between 700-1100 nm, is of an intensity that is greater than a sum of light emitted by either of covalently bound moieties individually.

138. The method of claim 133 wherein the covalently bound moieties that define the emissive species are linked by ethynyl, ethenyl, allenyl, butadiynyl, polyvinyl, thiophenyl, furanyl, pyrrolyl, or p-diethylylarenyl linkers or by a conjugated heterocycle that bears diethynyl, di(polyynynyl), divinyl, di(polyvinvyl), or di(thiophenyl) substituents.

139. The method of claim 133 wherein the polymeric material is a plurality of amphiphilic copolymers.

140. The method of claim 133 wherein the ancillary substituent on at least one of bound moieties comprising the emissive conjugated compound is alkyl, alkoxy, aryl, or ether.

141. The method of claim 133 wherein the ancillary substituent on at least one of bound moieties comprising the emissive conjugated compound is independently $C_1$-$C_{20}$ alkyl, $C_1$-$C_{20}$ alkoxy, —O—$(CH_2)_m CO_2 R'$, —O$(CH_2)$—(O$(CH_2))_x R$ or —O—$(CH_2)_p CROH$, where m and p are independently an integer from 1 to 10, x is an integer from 1 to 12, and R' is $C_1$-$C_{20}$ alkyl or $C_5$-$C_{20}$ aryl.

142. The method of claim 133 wherein the ancillary substituent on at least one of bound moieties comprising the emissive conjugated compound is aryl or substituted aryl.

* * * * *